US008212050B2

(12) United States Patent
Miyashita et al.

(10) Patent No.: US 8,212,050 B2
(45) Date of Patent: Jul. 3, 2012

(54) AMIDINE COMPOUNDS AND HERBICIDES

(75) Inventors: Yasuhiro Miyashita, Odawara (JP);
Koichi Kutose, Odawara (JP);
Kazuyuki Tomida, Odawara (JP);
Shigeo Yamada, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 1190 days.

(21) Appl. No.: 11/989,846

(22) PCT Filed: Aug. 2, 2006

(86) PCT No.: PCT/JP2006/315337
§ 371 (c)(1),
(2), (4) Date: Jan. 31, 2008

(87) PCT Pub. No.: WO2007/015533
PCT Pub. Date: Feb. 8, 2007

(65) Prior Publication Data
US 2011/0301355 A1    Dec. 8, 2011

(30) Foreign Application Priority Data

Aug. 2, 2005 (JP) ................. 2005-224452
May 2, 2006 (JP) ................. 2006-128341

(51) Int. Cl.
*C07D 263/34* (2006.01)
*C07D 207/12* (2006.01)
*C07C 257/10* (2006.01)
*A01P 13/00* (2006.01)
(52) U.S. Cl. .............. 548/236; 548/537; 564/245
(58) Field of Classification Search ............... None
See application file for complete search history.

(56) References Cited

U.S. PATENT DOCUMENTS 3,189,648 A    6/1965 Gerjovich

FOREIGN PATENT DOCUMENTS

| JP | 10-120658 | 5/1998 |
| WO | WO 97/12877 | 4/1997 |
| WO | WO 97/012877 | 4/1997 |

OTHER PUBLICATIONS

Lee et al., 1993, caplus an 1994:133989.*
Grundmann, von Christoph et al., "Die Umlagerung von Oxalodinitril-bis-aryliminen (Rearrangement of oxalodinitrilebisarylimines)," Justus Liebigs Annalen der Chemie, 744, 1971, p. 88-104.
Japanese Patent Office, International Search Report and Written Opinion dated May 23, 2006, from related International Patent Application No. PCT/JP2006/306487, filed Sep. 5, 2006 (in Japanese).
European Search Report dated Sep. 29, 2010, issued during prosecution of EP 06782206.4, 8 pages.
Oh, Kelm Chan, et al., "A Facile Synthesis of N-(p-Toluenesulfonyl)-N-Alkyl- and N,N-Dialkylcyanoformamidines and 1,3-Dialkyl-2-(p-Toluenesulfonyl)Guanidines", Tetrahedron Letters, 1992, vol. 33, No. 34, pp. 4963-4966.
Dickore, Karlfried, et al., "Benzoxazol-2-carbonsaure-Derivate aus 2.3-Dioxo-1.4-benzoxazinen (2-Benzoxazolecarboxylic acid derivatives from 2,3-dioxo-1,4-benzoxazines)", Liebigs Ann. Chem., 1970, vol. 733, pp. 70-87 (English abstract provided).
Iwakawa, Tseuno, et al., "New Synthesis of 5-Cyano-1,2,4-Thiadiazoles", Heterocycles, 1999, vol. 51, No. 4, pp. 811-819.
Lee, Hyunil, et al., "Novel Synthesis of 5-(Arylimino)-4-(dialkylamino)-5H-1,2,3-dithiazoles and the Mechanism of Their Formation", J. Org. Chem., 1994, vol. 59, pp. 6179-6183.
Hammam, A.S., et al., "Synthesis & Biological Activities of Some New Peptide Substituted Carbazoloquinones", Indian Journal of Chemistry, Apr. 1982, vol. 21B, pp. 348-351.
Mørkved, Eva H., et al., "Potential Acyl-transfer Agents. Reactions of N-Acyl-2-pyridinecarboxamides with Nucleophiles", Acta Chemica Scandinavica, 1982, vol. B 36, pp. 381-388.
Database Registry, Chemical Abstracts Service, Mar. 18, 2002, "1-Piperidineacetonitrile-(2-pyridinylimino", 1 page.
Database Registry, Chemical Abstracts Service, Oct. 12, 2000, "Benzenamine, N-(2-benzothiazoly1-3-oxazolidinylmethylene", 1 page.
Appel, Rolf et al., "Synthese and Reaktionen des 4,5-Dichlor-1,2,3-dithiazolium-chlorids," Chem. Ber. 118, pp. 1632-1643 (1985).
Lee, Hyunil et al., "Reactions of 5-(Arylimino)-4-chloro-5H-1,2,3-dithiazoles with Primary and Secondary Alkylamines: Novel Synthesis of (Arylimino)cyanomethyl Alkylamino Disulfides and Their Mechanisms of Formation," Journal of Organic Chemistry, 58, 1993, p. 7001-7008.

(Continued)

Primary Examiner — Sun Jae Loewe
(74) Attorney, Agent, or Firm — Kenyon & Kenyon LLP

(57) ABSTRACT

Novel amidine compounds which may be active ingredients in herbicides that are reliably effective at a lesser dose and highly safe, and herbicides containing these compounds as active ingredients are provided. Amidine compounds represented by a formula (1')

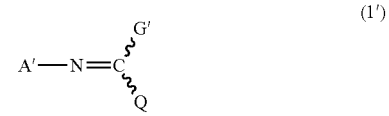

(1')

and herbicides containing at least one kind of these compounds as active ingredients, [wherein G is an optionally substituted nitrogen-containing heterocyclic group represented by a formula (2')

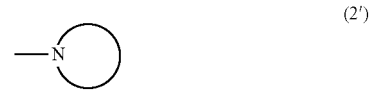

(2')

with a proviso that the number of carbons constituting the nitrogen-containing heterocycle of the nitrogen-containing heterocyclic group is 10 or less and that 2H-Indazole ring is excluded; Q' represents cyano or the like; and A' represents substituted phenyl or the like].

1 Claim, No Drawings

OTHER PUBLICATIONS

Katritzky, Alan et al., "Dibenzo[b,h][1,4,7]thiadiazonines: Examples of a Novel Ring System," Journal of Organic Chemistry, 66, 2001, p. 5601-5605.

Billert, Thomas et al., "New Heterocycles with Cycloamidine Substructure and their Ringtransformation Reactions with Acetylene Dicarboxylic Ester," Journal of Heterocyclic Chemistry, 38, 2001, p. 205-211.

Grundmann, von Christoph et al., "Die Umlagerung von Oxalodinitril-bis-aryliminen (Rearrangement of oxalodinitrilebisarylimines)," Justus Liebigs Annalen der Chemie, 744, 1971, p. 88-104. (w/English Abstract).

* cited by examiner

AMIDINE COMPOUNDS AND HERBICIDES

FIELD OF THE INVENTION

The present invention relates to novel amidine compounds and herbicides which contain these compounds.

Priority is claimed on Japanese Patent Applications No. 2005-224452 and 2006-128341, filed Aug. 2, 2005 and May 2, 2006, respectively, the content of which is incorporated herein by reference.

BACKGROUND ART

Many herbicides are being used for weed control, which has required intensive labor in the past when growing field and garden crops. However, the development of drugs which are reliably effective at a lesser dose and which are also possible to use safely is desired due to the occurrence of chemical damage to crops, environmental persistence of the drugs, and environmental pollution caused by the drugs.

Regarding the present invention, non-patent document 1 describes the production method of N-aryl-N' alkylcyanoformamidine similar to the compounds of the present invention.

However, this document does not describe that N-aryl-N' alkylcyanoformamidine has herbicidal activity.

[non-patent document 1] J. Org. Chem., Vol. 58, 7001 (1993)

DISCLOSURE OF THE INVENTION

[Problems to be Solved by the Invention]

An objective of the present invention is to provide novel amidine compounds which may be active ingredients of herbicides that are reliably effective when used in a low dose and are highly safe, and to provide herbicides which contain these compounds as active ingredients.

[Means for Solving the Problem]

As a result of intensive research in order to solve the above-mentioned problem, the present inventors discovered that amidine compounds represented by the below formula (1) have an excellent herbicide activity to complete the present invention. In other words, the present invention firstly provides herbicides characterized by containing at least one kind of amidine compound represented by a formula (1).

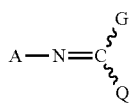

(1)

[In the formula, G is an optionally substituted nitrogen-containing heterocyclic group represented by a formula (2).

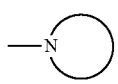

(2)

Q represents cyano, optionally substituted iminoalkyl, optionally substituted amide, optionally substituted thioam ide, or an optionally substituted nitrogen-containing heterocyclic group represented by a formula (3).

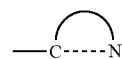

(3)

(In the formula, a dotted line represents a single or a double bond which connects carbon and nitrogen atoms), and A represents an optionally substituted aromatic group].

In the herbicides of the present invention, the formula (2) in the formula (1) is preferably a nitrogen-containing heterocyclic group which is 3 to 8-membered, saturated or unsaturated, and optionally substituted and more preferably an optionally substituted azetidine-1-yl group or an optionally substituted pyrrolidine-1-yl group.

In the herbicides of the present invention, in the formula (1), A is preferably a compound having an optionally substituted aromatic hydrocarbon group, and more preferably a compound having a group represented by a formula (4).

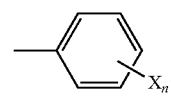

(4)

In the formula, X represents halogen, optionally substituted $C_{1-6}$ alkyl, optionally substituted $C_{2-6}$ alkenyl, optionally substituted $C_{2-6}$ alkynyl, optionally substituted aryl, optionally substituted $C_{1-6}$ alkyl carbonyl, optionally substituted $C_{2-6}$ alkenyl carbonyl, optionally substituted $C_{2-6}$ alkynyl carbonyl, optionally substituted aryl carbonyl, optionally substituted $C_{1-6}$ alkylthiocarbonyl, optionally substituted $C_{2-6}$ alkenylthiocarbonyl, optionally substituted $C_{2-6}$ alkynylthiocarbonyl, optionally substituted arylthiocarbonyl, cyano, substitutent represented by $X^{11}$, optionally substituted amino, nitro, hydroxyl, optionally substituted $C_{1-6}$ alkoxy, optionally substituted $C_{2-6}$ alkenyloxy, optionally substituted $C_{2-6}$ alkynyloxy, optionally substituted aryloxy, optionally substituted heteroyloxy, mercapto, optionally substituted $C_{1-6}$ alkylthio, optionally substituted $C_{2-6}$ alkenylthio, optionally substituted $C_{2-6}$ alkynylthio, optionally substituted arylthio, optionally substituted heteroylthio, optionally substituted alkyl sulfinyl, optionally substituted aryl sulfinyl, optionally substituted alkyl sulfonyl, optionally aryl sulfonyl, or optionally substituted heterocycle.

Moreover, substitutents which are in positions such that they are bondable to each other may bond together to form rings.

Here, the number of carbons present in the aforementioned substitutents with the phrase "optionally substituted" (i.e. $C_{1-6}$ alkyl, $C_{2-6}$ alkenyl, $C_{2-6}$ alkynyl, $C_{1-6}$ alkylcarbonyl, $C_{2-6}$ alkenylcarbonyl, $C_{2-6}$ alkynylcarbonyl, $C_{1-6}$ alkylthiocarbonyl, $C_{2-6}$ alkenylthiocarbonyl, $C_{2-6}$ alkynylthiocarbonyl, $C_{1-6}$ alkoxy, $C_{2-6}$ alkenyloxy, $C_{2-6}$ alkynyloxy, $C_{1-6}$ alkylthio, $C_{2-6}$ alkenylthio, and $C_{2-6}$ alkynylthio) refers to the number of carbons present in the groups without any substituents (i.e. alkyl, alkenyl, alkynyl, alkylcarbonyl, alkenylcarbonyl, alkynylcarbonyl, alkylthiocarbonyl, alkenylthiocarbonyl, alkynylthiocarbonyl, alkoxy, alkenyloxy, alkynyloxy, alkylthio, alkenylthio, and alkynylthio). Hereinafter, the same applies.

n is an integer of 0 to 5. When n is 2 or more, each X may be the same or different from each other.

$X^{11}$ is a substituent represented by a formula (5).

$$—A^1{}_{m^1}—\overset{O}{\underset{\|}{C}}—Z^1 \qquad (5)$$

wherein $m^1$ represents an integer of 0 to 3; $A^1$ represents an atom selected from carbon, nitrogen, oxygen, and sulfur, and which may be oxidized within a chemically acceptable range and which may be substituted; when $m^1$ is 2 or more, each $A^1$ may be the same or different from each other and combinations of each $A^1$ are within a chemically acceptable range and each $A^1$ may, within a chemically acceptable range of multiplicity, bond to each other.

When $A^1$ is carbon and one or more $A^1$ is substituted by two or more substitutents, the substituents which are in a bondable positional relationship may bond together to form a ring.

$Z^1$ represents a group represented by $—OR^{11}$ or $—NR^{12}R^{13}$.

$R^{11}$ represents hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, or a group represented by $X^{12}$.

$R^{12}$ and $R^{13}$ each independently represents hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, a group represented by $X^{12}$, hydroxyl, optionally substituted $C_{1-6}$ alkoxy, optionally substituted $C_{2-6}$ alkenyloxy, optionally substituted $C_{2-6}$ alkynyloxy, optionally substituted aryloxy, optionally substituted alkyl sulfinyl, optionally substituted aryl sulfinyl, optionally substituted alkyl sulfonyl, optionally substituted aryl sulfonyl, or optionally substituted amino.

Moreover, these groups may form covalent bonds or, within a chemically acceptable range, may form ionic bonds.

Furthermore, $R^{12}$ and $R^{13}$ may bond together to form a ring.

$X^{12}$ is a substituent represented by a formula (6).

$$—A^2{}_{m^2}—\overset{Y}{\underset{\|}{C}}—Z^2 \qquad (6)$$

[In the formula, $m^2$ is an integer of 1 to 3, $A^2$ represents optionally substituted carbon and may be substituted within a chemically acceptable range. When $m^2$ is 2 or more, each $A^2$ may bond to each other within a chemically acceptable range of multiplicity.

When one or more $A^2$ is substituted by two or more substituents, the substituents which are in a bondable positional relationship may bond together to form a ring.

Y represents oxygen or optionally substituted nitrogen.

$Z^2$ is a group represented by $—OR^{21}$ or $—NR^{22}R^{23}$ when Y is oxygen and $Z^2$ represents hydrogen or optionally substituted $C_{1-6}$ alkyl when Y is nitrogen.

$R^{21}$ represents hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, or a group represented by $X^{13}$.

$R^{22}$ and $R^{23}$ each independently represents hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, a group represented by $X^{13}$, optionally substituted $C_{1-6}$ alkoxy, optionally substituted $C_{2-6}$ alkenyloxy, optionally substituted $C_{2-6}$ alkynyloxy, optionally substituted aryloxy, optionally substituted alkyl sulfinyl, optionally substituted aryl sulfinyl, optionally substituted alkyl sulfonyl, or optionally substituted aryl sulfonyl.

Moreover, these groups may form covalent bonds or, within a chemically acceptable range, may form ionic bonds.

Furthermore, $R^{22}$ and $R^{23}$ may bond together to form a ring when neither is hydrogen.

$X^{13}$ is a substituent represented by a formula (7).

$$—A^3{}_{m^3}—\overset{O}{\underset{\|}{C}}—Z^3 \qquad (7)$$

(In the formula, $m^3$ is an integer of 1 to 3, $A^3$ represents optionally substituted carbon and may be substituted within a chemically acceptable range. When $m^3$ is 2 or more, each $A^3$ may bond to each other within a chemically acceptable range of multiplicity.

When one or more $A^3$ is substituted by two or more substituents, the substituents which are in a bondable positional relationship may bond together to form a ring.

$Z^3$ is a group represented by $—OR^{31}$ or $—NR^{32}R^{33}$.

$R^{31}$ represents hydrogen, optionally substituted $C_{1-6}$ alkyl, optionally substituted $C_{2-6}$ alkenyl, optionally substituted $C_{2-6}$ alkynyl, optionally substituted aryl, or optionally substituted heterocycle.

$R^{32}$ and $R^{33}$ each independently represents hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, optionally substituted $C_{1-6}$ alkoxy, optionally substituted $C_{2-6}$ alkenyloxy, optionally substituted $C_{2-6}$ alkynyloxy, optionally substituted aryloxy, optionally substituted alkyl sulfinyl, optionally substituted aryl sulfinyl, optionally substituted alkyl sulfonyl, or optionally substituted aryl sulfonyl.

Moreover, these groups may form covalent bonds or, within a chemically acceptable range, may form ionic bonds.

Furthermore, $R^{32}$ and $R^{33}$ may bond together to form a ring when neither is hydrogen.

Secondly, the present invention provides amidine compounds represented by a formula (1').

$$A'—N=C\genfrac{}{}{0pt}{}{G'}{Q'} \qquad (1')$$

{In the formula, G' represents an optionally substituted nitrogen-containing heterocyclic group represented by a formula (2')

$$—N\bigcirc \qquad (2')$$

with a proviso that the number of carbons constituting the nitrogen-containing heterocycle of the nitrogen-containing heterocyclic group is 10 or less and that 2H-Indazole ring is excluded.

Q' represents cyano, optionally substituted iminoalkyl, optionally substituted amide, optionally substituted thioamide, or optionally substituted and condensed 5-membered ring group represented by a formula (3').

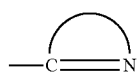
(3')

A' is a group represented by a formula (4').

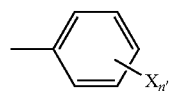
(4')

[In the formula, X represents halogen, optionally substituted $C_{1-6}$ alkyl, optionally substituted $C_{2-6}$ alkenyl, optionally substituted $C_{2-6}$ alkynyl, optionally substituted aryl, optionally substituted $C_{1-6}$ alkyl carbonyl, optionally substituted $C_{2-6}$ alkenyl carbonyl, optionally substituted $C_{2-6}$ alkynyl carbonyl, optionally substituted aryl carbonyl, optionally substituted $C_{1-6}$ alkylthiocarbonyl, optionally substituted $C_{2-6}$ alkenylthiocarbonyl, optionally substituted $C_{2-6}$ alkynylthiocarbonyl, optionally substituted arylthiocarbonyl, cyano, substitutent represented by $X^{11}$, optionally substituted amino, nitro, hydroxyl, optionally substituted $C_{1-6}$ alkoxy, optionally substituted $C_{2-6}$ alkenyloxy, optionally substituted $C_{2-6}$ alkynyloxy, optionally substituted aryloxy, optionally substituted heteroyloxy, mercapto, optionally substituted $C_{1-6}$ alkylthio, optionally substituted $C_{2-6}$ alkenylthio, optionally substituted $C_{2-6}$ alkynylthio, optionally substituted arylthio, optionally substituted heteroylthio, optionally substituted alkyl sulfinyl, optionally substituted aryl sulfinyl, optionally alkyl sulfonyl, optionally substituted aryl sulfonyl, or an optionally substituted heterocyclic group.

Moreover, substituents which are in positions such that they are bondable to each other may bond together to form rings.

n' is an integer of 2 to 5. Each X may be the same or different from each other.

$X^{11}$ is a substituent represented by a formula (5).

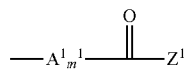
(5)

[In the formula, $m^1$ represents an integer of 0 to 3; $A^1$ represents an atom selected from carbon, nitrogen, oxygen, and sulfur, and which may be oxidized within a chemically acceptable range and which may be substituted; when $m^1$ is 2 or more, each $A^1$ may be the same or different from each other and combinations of each $A^1$ are within a chemically acceptable range and each $A^1$ may, within a chemically acceptable range of multiplicity, bond to each other.

When $A^1$ is carbon and one or more $A^1$ is substituted by two or more substituents, the substituents which are in a bondable positional relationship may bond together to form a ring.

$Z^1$ represents a group represented by $-OR^{11}$ or $-NR^{12}R^{13}$.

$R^{11}$ represents hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, or a group represented by $X^{12}$.

$R^{12}$ and $R^{13}$ each independently represents hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, a group represented by $X^{12}$, hydroxyl, optionally substituted $C_{1-6}$ alkoxy, optionally substituted $C_{2-6}$ alkenyloxy, optionally substituted $C_{2-6}$ alkynyloxy, optionally substituted aryloxy, optionally substituted alkyl sulfinyl, optionally substituted aryl sulfinyl, optionally substituted alkyl sulfonyl, optionally substituted aryl sulfonyl, or optionally substituted amino.

Moreover, $R^{12}$ and $R^{13}$ may bond together to form a ring.

$X^{12}$ is a substituent represented by a formula (6).

(6)

[In the formula, $m^2$ is an integer of 1 to 3, $A^2$ represents optionally substituted carbon and may be substituted within a chemically acceptable range. When $m^2$ is 2 or more, each $A^2$ may bond to each other within a chemically acceptable range of multiplicity. When one or more $A^2$ is substituted by two or more substituents, the substituents which are in a bondable positional relationship may bond together to form a ring.

Y represents oxygen or optionally substituted nitrogen.

$Z^2$ is a group represented by $-OR^{21}$ or $-NR^{22}R^{23}$ when Y is oxygen and $Z^2$ represents hydrogen or optionally substituted $C_{1-6}$ alkyl when Y is nitrogen.

$R^{21}$ represents hydrogen, optionally substituted $C_{1-6}$ allyl, optionally substituted $C_{2-6}$ alkenyl, optionally substituted $C_{2-6}$ alkynyl, optionally substituted aryl, optionally substituted heterocycle, or a group represented by $X^{13}$.

$R^{22}$ and $R^{23}$ each independently represent hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, a group represented by $X^{13}$, optionally substituted $C_{1-6}$ alkoxy, optionally substituted $C_{2-6}$ alkenyloxy, optionally substituted $C_{2-6}$ alkynyloxy, optionally substituted aryloxy, optionally substituted alkyl sulfinyl, optionally substituted aryl sulfinyl, optionally substituted alkyl sulfonyl, or optionally substituted aryl sulfonyl. Moreover, $R^{22}$ and $R^{23}$ may bond together to form a ring when neither is hydrogen.

$X^{13}$ is a substituent represented by a formula (7).

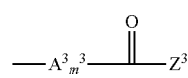
(7)

(In the formula, $m^3$ is an integer of 1 to 3, $A^3$ represents optionally substituted carbon and may be substituted within a chemically acceptable range. When $m^3$ is 2 or more, each $A^3$ may bond to each other within a chemically acceptable range of multiplicity.

When one or more $A^3$ is substituted by two or more substituents, the substituents which are in a bondable positional relationship may bond together to form a ring.

$Z^3$ is a group represented by $-OR^{31}$ or $-NR^{32}R^{33}$.

$R^{31}$ represents hydrogen, optionally substituted $C_{1-6}$ alkyl, optionally substituted $C_{2-6}$ alkenyl, optionally substituted $C_{2-6}$ alkynyl, optionally substituted aryl, or an optionally substituted heterocyclic group.

$R^{32}$ and $R^{33}$ each independently represents hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, optionally substituted $C_{1-6}$ alkoxy, optionally substituted $C_{2-6}$ alkenyloxy, optionally substituted $C_{2-6}$ alkynyloxy, optionally substituted aryloxy, optionally substituted allyl sulfinyl, optionally substituted aryl sulfinyl, optionally substituted alkyl sulfonyl, or optionally substituted aryl sulfonyl.

Moreover, $R^{32}$ and $R^{33}$ may bond together to form a ring when neither is hydrogen.)]]]}

In the amidine compounds of the present invention, formula (2') in the formula (1') is preferably a nitrogen-containing heterocycle which is 3 to 8-membered, saturated or unsaturated, and optionally substituted; and more preferably optionally substituted azetidine-1-yl group or optionally substituted pyrrolidine-1-yl group.

[Effects of the Invention]

According to the present invention, novel amidine compounds and herbicides containing these compounds as active ingredients are provided.

PREFERRED EMBODIMENTS OF THE INVENTION

The present invention will be described in detail below.

The present invention is a herbicide characterized by containing one or more amidine compounds represented by the formula (1) and the novel amidine compounds represented by the formula (1').

(1) Amidine Compounds Represented by Formulae (1) and (1')

In the amidine compounds represented by the formula (1) (hereinafter referred to as the "compound (1)" at times), G is a group represented by the formula (2) (hereinafter referred to as the "nitrogen-containing heterocyclic group (2)").

The nitrogen-containing heterocycle in the nitrogen-containing heterocyclic group (2) is a heterocycle having one or more nitrogen in the ring and which is saturated or non-saturated. The nitrogen-containing heterocycle may contain oxygen and/or sulfur in addition to nitrogen and may be monocyclic or may have a condensed ring structure or a crosslinked structure.

The total number of nitrogen, oxygen, and sulfur constituting the nitrogen-containing heterocycle is normally 1 to 4 and preferably 1 to 3.

Moreover, the number of carbons constituting the nitrogen-containing heterocycle of the nitrogen-containing heterocyclic group (2) is preferably 10 or less and more preferably 1 to 8.

Although specific examples of the nitrogen-containing heterocyclic group (2) include those shown in Table 1 below, it is not limited to them. Note that the substituents on nitrogen and on atoms constituting the ring are abbreviated and only the basic backbone is described here.

TABLE 1

 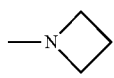

TABLE 1-continued

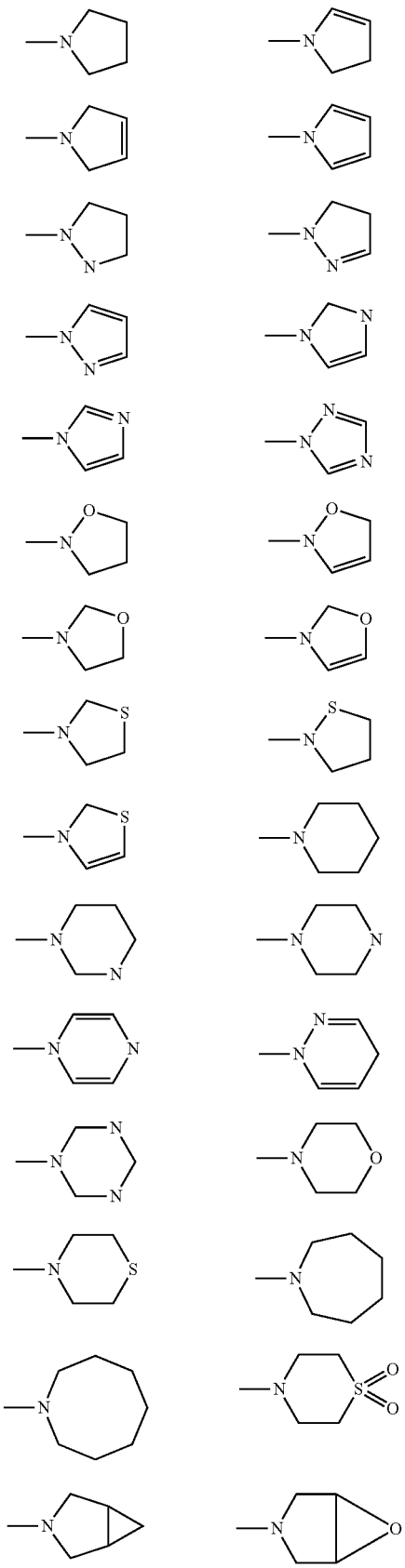

TABLE 1-continued

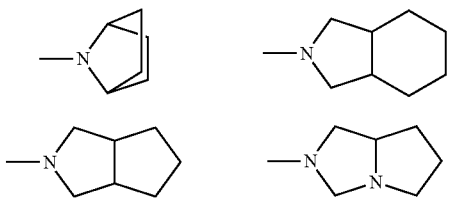

The substituents of the nitrogen-containing heterocyclic group (2) are not particularly limited.

For example, halogen such as fluorine, chlorine, and bromine; $C_{1-6}$ alkyl which may have a substituent such as methyl, ethyl, trifluoromethyl, and benzyl; $C_{2-6}$ alkenyl which may have a substituent such as aryl or 3-chloroaryl; $C_{2-6}$ alkynyl which may have a substituent such as propargyl; aryl which may have a substituent such as phenyl or 4-methylphenyl; formyl;

$C_{1-6}$ alkylcarbonyl which may have a substituent such as acetyl, or trifluoroacetyl; $C_{2-6}$ alkenylcarbonyl which may have a substituent such as cinnamyl; $C_{2-6}$ alkynylcarbonyl which may have a substituent such as propargylcarbonyl; aryl carbonyl which may have a substituent such as benzoyl or 4-chlorobenzoyl; $C_{1-6}$ alkylthiocarbonyl which may have a substituent such as thioacetyl; $C_{2-6}$ alkenylthiocarbonyl which may have a substituent such as allylthiocarbonyl; $C_{2-6}$ alkynylthiocarbonyl which may have a substituent such as propargylthiocarbonyl; arylthiocarbonyl which may have a substituent such as thiobenzoyl; carboxyl; $C_{1-6}$ alkoxycarbonyl which may have a substituent such as methoxycarbonyl or ethoxycarbonyl; $C_{2-6}$ alkenyloxycarbonyl which may have a substituent such as acryloyl or methacryloyl;

$C_{3-6}$ alkynyloxycarbonyl which may have a substituent such as propargyloxycarbonyl; aryloxycarbonyl which may have a substituent such as phenyoxycarbonyl or 2,4-dichlorophenoxycarbonyl; cyano; amino which may have a substituent such as amino, dimethylamino, or acetylamino; imino which may have a substituent such as imino or dimethylimino; nitro; hydroxyl; oxo; $C_{1-6}$ alkoxy which may have a substituent such as methoxy, ethoxy, t-butoxy; $C_{2-6}$ alkenyloxy which may have a substituent such as allyloxy or crotyloxy; $C_{2-6}$ alkynyloxy which may have a substituent such as propargyloxy; aryloxy which may have a substituent such as phenoxy or 4-methylphenoxy; heteroyloxy which may have a substituent; mercapto; $C_{1-6}$ alkylthio which may have a substituent such as methylthio or ethylthio; $C_{2-6}$ alkenylthio which may have a substituent such as allylthio or crotylthio; $C_{2-6}$ alkynylthio which may have a substituent such as propargylthio; arylthio which may have a substituent such as phenylthio; heteroylthio which may have a substituent; alkylsulfinyl which may have a substituent such as methylsulfinyl; arylsulfinyl which may have a substituent such as phenylsulfinyl; alkylsulfonyl which may have a substituent such as methylsulfonyl; arylsulfonyl which may have a substituent such as phenylsulfonyl; and a heterocyclic group which may have a substituent.

In addition, heterocycle of heteroyloxy group which may have a substituent, of heteroylthio group which may have a substituent, of a heterocycle group which may have a substituent includes cyclic compounds having at least one atom selected from nitrogen, oxygen and sulfur in the ring and which is saturated or unsaturated. Specific examples include aromatic heterocycles such as imidazole, pyrazole, pyridine, pyrimidine, pyrazine, pyridazine, triazole, triazine, indole, indazole, purine, thiadiazole, oxadiazole, quinoline, phthalazine, naphthyridine, quinoxaline, quinazoline, cinnoline, pteridine, acridine, phenanthroline, phenazine, tetrazole, thiazole, oxazole, benzoimidazole, benzoxazole, benzothiazole, indolenine, tetrazaindene, and furan; and non-aromatic heterocycles such as pyrrolidine, piperidine, morpholine, tetrahydrofuran, tetrahydropyran, aziridine, azetidine, oxazolidine, piperazine, thiazolidine, and trioxane.

Moreover, the nitrogen-containing heterocyclic group (2) may have a plurality of the same or different substituents at arbitrary positions.

Q represents cyano, iminoalkyl which may have a substituent, amide which may have a substituent, thioamide which may have a substituent, or a nitrogen-containing heterocyclic group represented by the formula (3) and which may have a substituent.

Examples of iminoalkyl which may have a substituent include $C_{1-6}$ iminoalkyl iminomethyl, iminoethyl, and iminopropyl.

Examples of iminoalkyl which may have a substituent include N-substituted iminomethyl where nitrogen is substituted by hydroxyl, by $C_{1-6}$ alkoxy which may have a substituent, by $C_{2-6}$ alkenyloxy which may have a substituent, by $C_{2-6}$ alkynyloxy which may have a substituent, by aryloxy which may have a substituent, or by heteroyloxy which may have a substituent.

Examples of amide which may have a substituent include aminocarbonyl where 0 to 2 nitrogens are substituted by the group such as $C_{1-6}$ alkyl which may have a substituent, $C_{2-6}$ alkenyl which may have a substituent, $C_{2-6}$ alkynyl which may have a substituent, aryl which may have a substituent, a heterocyclic group which may have a substituent, $C_{2-10}$ acyl which may have a substituent, $C_{2-6}$ alkenylcarbonyl which may have a substituent, $C_{2-6}$ alkynylcarbonyl which may have a substituent, arylcarbonyl which may have a substituent, and heteroylcarbonyl which may have a substituent. Additionally, when 2 nitrogens are substituted, the substituents on nitrogen may bond to foam a ring structure within a chemically acceptable range.

Specific examples of thioamide which may have a substituent include aminothiocarbonyl where 0 to 2 nitrogens are substituted by a group such as $C_{1-6}$ alkyl which may have a substituent, $C_{2-6}$ alkenyl which may have a substituent, $C_{2-6}$ alkynyl which may have a substituent, aryl which may have a substituent, a heterocyclic group which may have a substituent, $C_{2-10}$ acyl which may have a substituent, $C_{2-6}$ alkenylcarbonyl which may have a substituent, $C_{2-6}$ alkynylcarbonyl which may have a substituent, arylcarbonyl which may have a substituent, and heteroylcarbonyl which may have a substituent. Additionally, when 2 nitrogens are substituted, the substituents on nitrogen may bond to form a ring structure within a chemically acceptable range.

In the group represented by the formula (3) (hereinafter referred to as the "nitrogen-containing heterocyclic group (3)" at times), the dotted line represents a single or double bond linking carbon and nitrogen. In other words, the nitrogen-containing heterocyclic group (3) is one where the atom adjacent to the carbon having linkages is always nitrogen and these carbon and nitrogen link by a single or double bond, and also, having 1 to 4 nitrogens in the ring and which is saturated or unsaturated.

The nitrogen-containing heterocyclic group (3) may contain oxygen and/or sulfur in addition to nitrogen. The total number of nitrogen, oxygen, and sulfur constituting the heterocycle is normally 1 to 4 and preferably 1 to 3.

Moreover, although the number of members constituting the nitrogen-containing heterocycle of the nitrogen-containing heterocyclic group (3) is not particularly limited, it is normally 3 to 10 and preferably 3 to 8.

Although specific examples of the nitrogen-containing heterocyclic group (3) include imidazolyl, pyrazolyl, morpholynyl, triazolyl, indolyl, oxadiazolyl, quinolyl, oxazolyl, and those described in Table 2 below, it is not limited to them. Note that in Table 2 below, the substituents on nitrogen and on atoms constituting the ring are abbreviated and only the basic backbone is described.

[Table 2]

TABLE 2

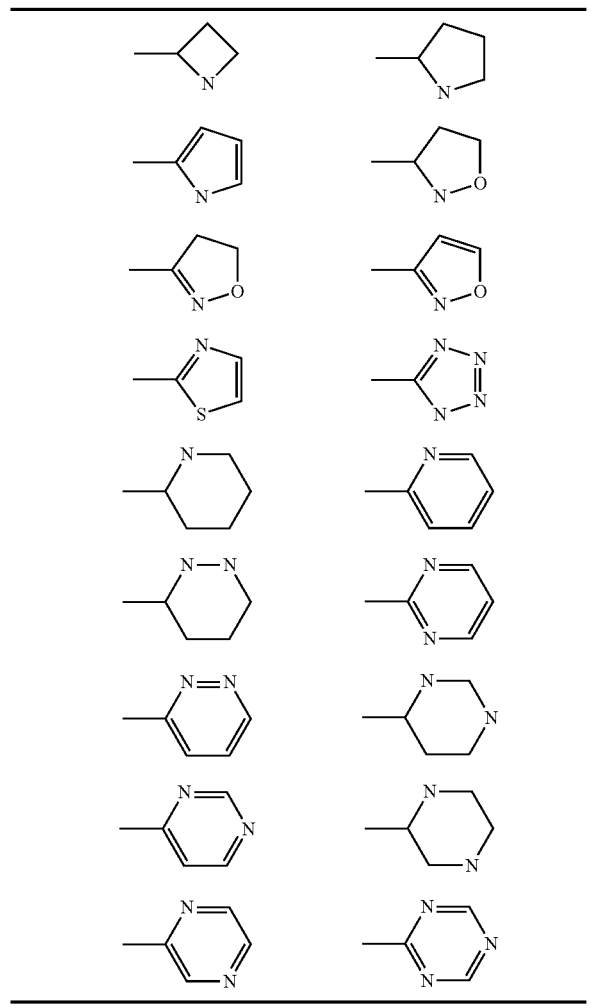

The substituent of the nitrogen-containing heterocyclic group (3) is not particularly limited and examples thereof include substituents similar to those shown as examples of the nitrogen-containing heterocyclic group (2).

Moreover, the nitrogen-containing heterocyclic group (3) may have a plurality of the same or different substituents at arbitrary positions.

A represents an aromatic group which may have a substituent.

Examples of the aromatic group of A include aromatic hydrocarbon groups such as phenyl, 1-naphthyl, or 2-naphthyl; and aromatic heterocyclic groups such as pyridyl, thiazole, or oxazole.

Among them, phenyl, which may have a substituent, is preferable as A and the group represented by a formula (4) is more preferable.

Specific examples of a formula (5), which is a substituent of the formula (4), include substituents shown below. The formula (5) below includes those containing formulae (6) and (7).

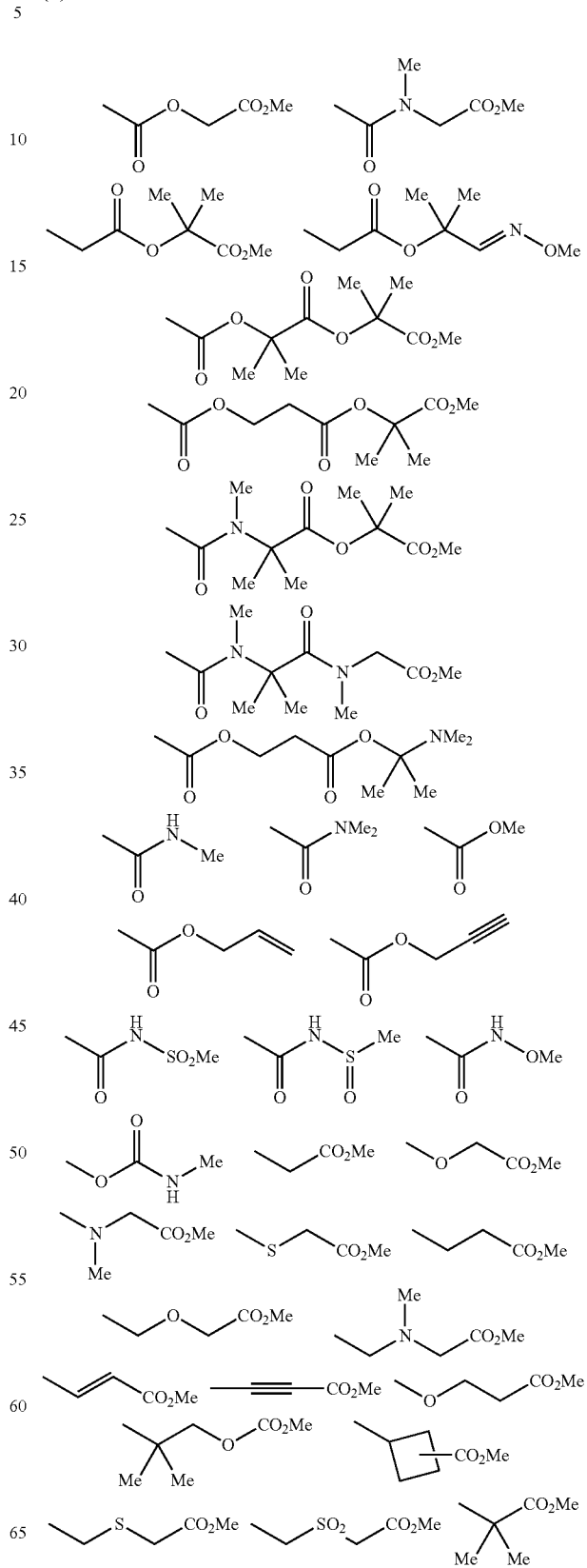

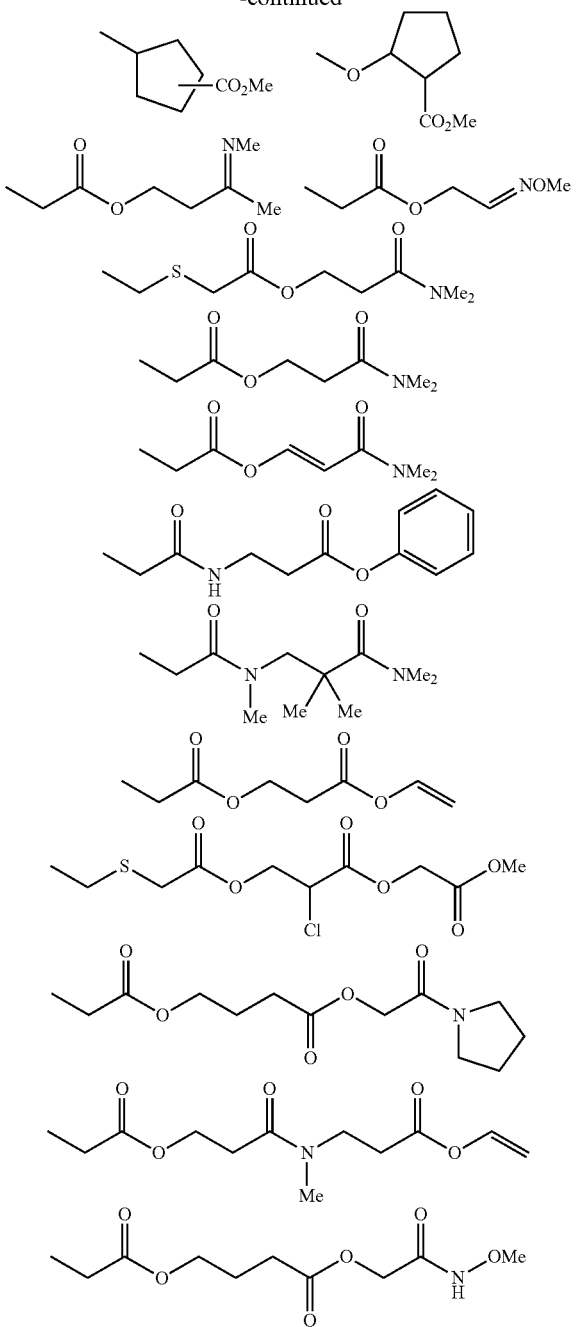

Moreover, examples of the substituent of the functional group in X of the formula (4) include substituents similar to those shown as specific examples of the nitrogen-containing heterocyclic group (2).

The substituent of $R^{11}$, $R^{12}$, and $R^{13}$ in $Z^1$ is not particularly limited and examples thereof include substituents similar to those shown as specific examples of the nitrogen-containing heterocyclic group (2).

In the formula (6), Y represents oxygen or optionally substituted nitrogen and specifically represents $NR^{101}$, $NNR^{102}R^{103}$, $NOR^{104}$, $NS(=O)R^{105}$, $NS(=O)_2R^{106}$, or the like.

$R^{101}$ to $R^{106}$ each independently represents hydrogen, optionally substituted $C_{1-6}$ alkyl, optionally substituted $C_{1-6}$ alkyl carbonyl, optionally substituted $C_{1-6}$ alkylthiocarbonyl, optionally substituted $C_{1-6}$ alkoxycarbonyl, optionally substituted $C_{2-6}$ alkenyl, optionally substituted $C_{2-6}$ alkenyl carbonyl, optionally substituted $C_{2-6}$ alkenylthiocarbonyl, optionally substituted $C_{2-6}$ alkenyloxycarbonyl, optionally substituted $C_{2-6}$ alkynyl, optionally substituted $C_{2-6}$ alkynyl carbonyl, optionally substituted $C_{2-6}$ alkynylthiocarbonyl, optionally substituted $C_{2-6}$ alkynyloxycarbonyl, optionally substituted aryl, optionally substituted aryl carbonyl, optionally substituted arylthiocarbonyl, optionally substituted aryloxycarbonyl, optionally substituted heterocycle, optionally substituted heteroylcarbonyl, optionally substituted heteroylthiocarbonyl, optionally substituted heteroyloxycarbonyl, and the substituent substituting these groups is not particularly limited and examples thereof include those similar to the substituent of nitrogen-containing heterocyclic group (2).

Among them, in the present invention, A is preferably the group represented by the formula (4) from the viewpoint of providing excellent herbicide activity, and more preferably 2,4-di-substituted phenyl, 4,5-disubstituted phenyl, or 2,4,5-trisubstituted phenyl, and most preferably 2,4,5-trisubstituted phenyl.

Additionally, although geometric isomerism in imino linkages is not particularly limited, the substituents A and G are preferably transisomers.

The compound (1) can be produced by the production method 1 to 7 shown below, for example. Note that unless particularly shown clearly in the figures below, reaction stereospecificity does not exist.

(Production Method 1)

The compound (1) can be produced by the method described in the literature below.

J. Org. Chem., Vol. 58, 7001 (1993), etc.

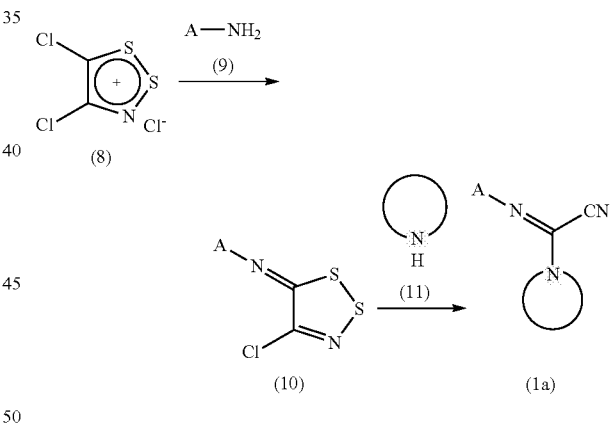

(In the formula, A is as defined above.)

A compound (8), which is a raw material for the production, can be produced by the method described in the literature (R. Appel et al., Chem. Ber., Vol. 118, 1632 (1985)).

(Production Method 2)

The compound (1a) can also be produced by the method shown below.

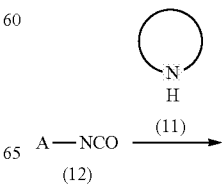

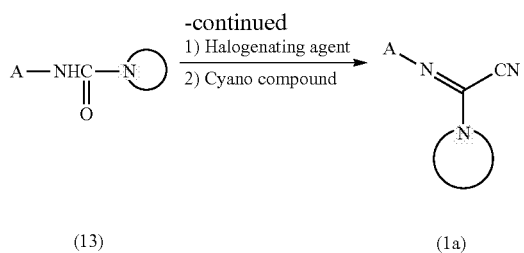

(In the formula, A is as defined above.)

Examples of halogenating agents used in the halogenating reaction of a compound (13) include $CCl_4$—$PPh_3$, $CBr_4$—$PPh_3$, phosphorus trichloride, phosphorus pentachloride, phosphorus oxychloride, thionyl chloride, sulfuryl chloride, chlorine, phosphorus oxybromide, thionyl bromide, and bromine.

The amount of halogenating agent is used normally 1 to 5 times that of the compound (13), which is the substrate, in terms of moles.

The reaction using such a halogenating agent can be carried out in an appropriate inert solvent.

The inert solvent to be used is not particularly limited as long as it is inert solvent in the reaction. Examples include, for instance, halogenated hydrocarbons such as dichloromethane, chloroform, carbon tetrachloride, and 1,2-dichloroethane; aromatic hydrocarbons such as benzene, toluene, and xylene; aliphatic hydrocarbons such as pentane, hexane, and octane; alicyclic hydrocarbons such as cyclopentane and cyclohexane; ethers such as diethylether and tetrahydrofuran; amides such as N,N-dimethylformamide and N-methylpyrolidone; sulfoxides such as dimethylsulfoxide; nitriles such as acetonitrile; and mixed solvents of two or more kinds thereof.

Although the reaction temperature is not particularly limited, the temperature range is normally from 0° C. to the boiling point of the solvent used.

After the completion of the reaction using a halogenating agent, it is preferable to react cyano compounds after removing the excess halogenating agent from the reaction system.

Examples of cyano compounds to be used include, for instance, metal cyanides such as cuprous cyanide, potassium cyanide, and sodium cyanide.

The amount of cyano compounds used is normally 1 to 5 times that of the compound (13), which is the substrate, in teens of mole.

The reaction using cyano compounds can be carried out in an appropriate inert solvent.

Examples of the inert solvent to be used include those similar to the abovementioned listed solvents which can be used in the reaction using a halogenating agent.

Although the reaction temperature is not particularly limited, the temperature range is normally from 0° C. to the boiling point of the solvent used.

(Production Method 3)

The compound (1a) can also be produced by the method shown below.

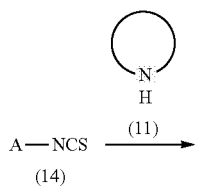

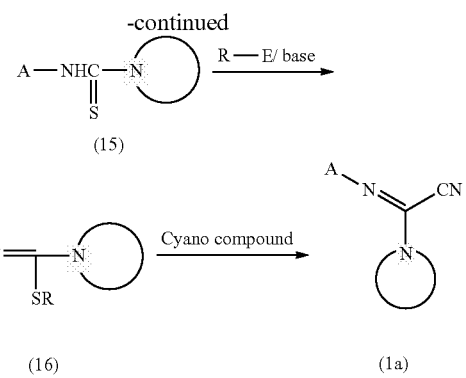

(In the formula, A is as defined above. R represents alkyl and E represents a leaving group.)

The compound represented by R-E to be reacted with the compound (15) is an alkylating agent, and examples thereof include, for instance, alkyl halides such as methyl iodide and dialkyl sulfates such as dimethyl sulfate.

Examples of the bases used here include metal hydroxides such as sodium hydroxide and potassium hydroxide; carbonates such as sodium carbonate and potassium carbonate; metal hydrides such as sodium hydride; metal alkoxides such as sodium methoxide and sodium ethoxide; and organic bases such as triethylamine and pyridine.

The reaction of the compound (15) with the compound represented by the formula R-E can be carried out in an appropriate inert solvent.

The inert solvent to be used is not particularly limited as long as it is an inert solvent in the reaction. Examples include, for instance, halogenated hydrocarbons such as dichloromethane, chloroform, carbon tetrachloride, and 1,2-dichloroethane; aromatic hydrocarbons such as benzene, toluene, and xylene; aliphatic hydrocarbons such as pentane, hexane, and octane; alicyclic hydrocarbons such as cyclopentane and cyclohexane; ethers such as diethylether and tetrahydrofuran; ketones such as acetone and methylethylketone; amides such as N,N-dimethylformamide; and mixed solvents of two or more kinds thereof.

Although the reaction temperature is not particularly limited, the temperature range is normally from 0° C. to the boiling point of the solvent used.

Examples of the cyano compounds to be reacted with the compound (16) include those similar to the cyano compounds listed in the Production method 2 which can be suitably used. In addition, the usage of the cyano compounds, solvents, or the like to be used are also similar to those in the Production method 2.

(Production Method 4)

The compound (1a) can also be produced by the method shown below.

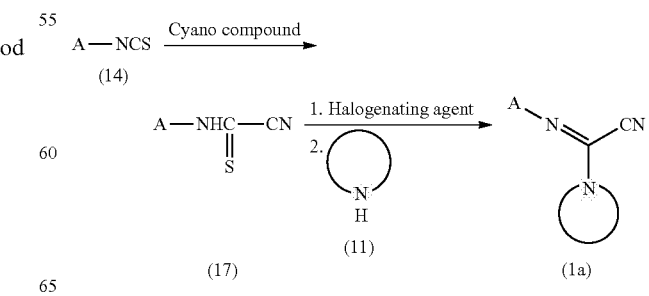

(In the formula, A is as defined above.)

Examples of cyano compounds, halogenating agents, and the compound (11) which can be used here include ones similar to those listed in the Production method 2. Moreover, the cyano compounds, halogenating agents and the usage of the compound (11), and solvents to be used, or the like, are also similar to those in the Production method 2.

(Production Method 5)

A compound (1b) whose Q is amide (CONH$_2$) in the formula (1) (hereinafter referred to as the "compound (1b)") and a compound (1c) whose Q is a substituted amide (CONr$_1$r$_2$) in the formula (1) (hereinafter referred to as the "compound (1c)") can be produced by the method shown below.

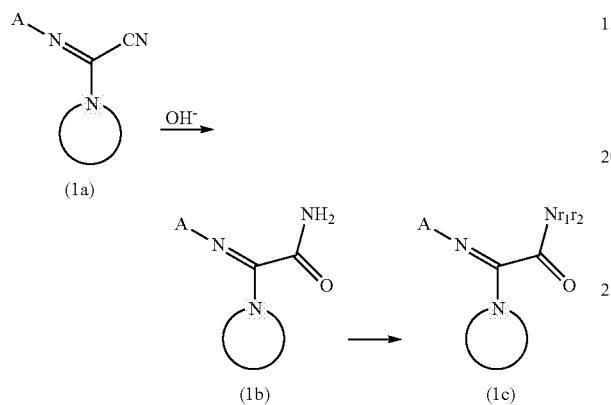

(In the formula, A is as defined above r$_1$ and r$_2$ each independently represents hydrogen, alkyl, aryl, or acyl with a proviso that r$_1$ and r$_2$ are not hydrogen.)

The reaction to obtain the compound (1b) by hydrolyzing the compound (1a) can be carried out similarly to a known reaction method to obtain amides by hydrolyzing cyanos.

Examples of the reaction method to obtain the compound (1c) from the compound (1b) include, for instance, a method of applying alkylating agents such as methyl iodide and dimethyl sulfate to the compound (1b) in the presence of a base; or a method of applying acylating agents such as acetylchloride and benzoylchloride to the compound (1b) in the presence of a base.

(Production Method 6)

A compound (1d) whose Q is thioamide in the formula (1) and a compound (1e) whose Q is a substituted thioamide in the formula (1) can be produced by the method shown below.

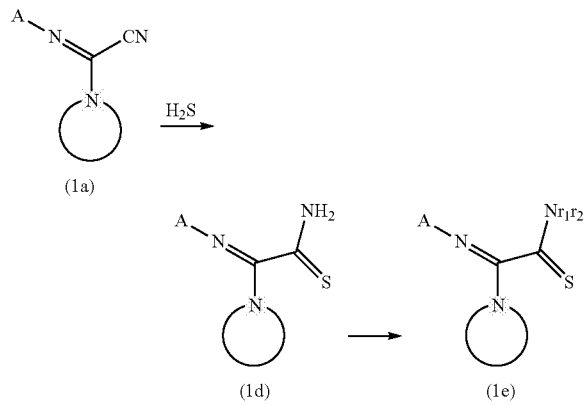

(In the formula, A, r$_1$ and r$_2$ are defined as above.)

The reaction to obtain the compound (1d) from the compound (1a) can be carried out similarly to a known reaction method which converts cyanos to thioamides by applying hydrogen sulfide.

Moreover, the reaction to obtain the compound (1e) from the compound (1d) can be carried out similarly to the method to obtain the compound (1c) from the compound (1b) in the Production method 5.

(Production Method 7)

A compound (1f) can also be produced by the method shown below.

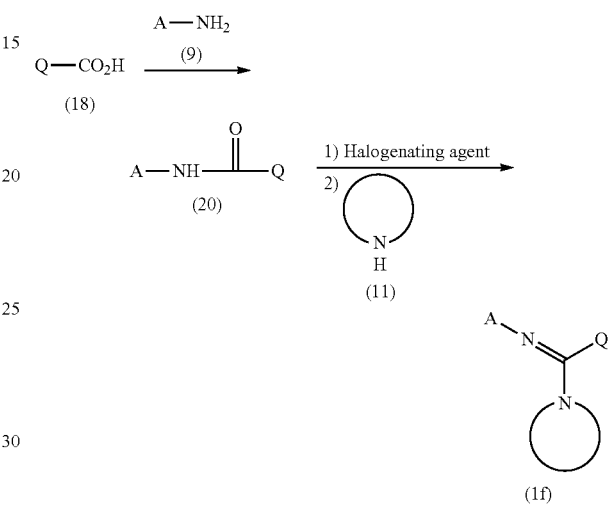

(In the formula, Q and A are defined as above.)

Specific examples of halogenating agents and the compound (11) used here, the usages thereof, reaction conditions, or the like, are similar to those described above in Production method 2.

Examples of salts of the compound (1) include the salts obtained from the compound (1) and acids.

Specific examples of the salts of the compound (1) include salts of inorganic acids such as hydrochlorides, nitrates, sulfates, and phosphates; and salts of organic acids such as acetates, lactates, benzoates, and salicylates.

The production method of salts of the compound (1) is not particularly limited and examples thereof include a conventionally known production method such as the method of mixing/stirring the compound (1) with a predetermined amount of acid in an appropriate solvent.

In all cases, targeted compounds can be isolated in high yield after completing the reaction by an after-treatment operation, purification operation, or the like following common procedures in synthetic organic chemistry Structures of targeted compounds can be identified by measurements of IR spectra, NMR spectra, and mass spectra, elemental analysis, or the like.

Note that although geometric isomers, or the like, may exist in the compound (1) due to the double bond between carbon and nitrogen, these isomers are all within the scope of the present invention.

The compound (1) obtained as described above has an excellent herbicidal activity, as described later, and is useful as an active ingredient of herbicides.

(2) Herbicide

Herbicides of the present invention are characterized by containing at least one kind of the compound (1) or salts thereof (hereinafter referred to as the "compound of the present invention"),as an active ingredient.

The compounds of the present invention exhibit high herbicidal activity in either soil treatment or foliar treatment under upland farming conditions; are effective on various upland weeds such as crabgrass, giant foxtail, velvetleaf, and pigweed; and also include compounds which exhibit selectivity toward crops such as corn.

Moreover, the compounds of the present invention include compounds which exhibit plant growth-regulating activity such as retarding and defoliant toward useful plants such as agricultural crops, ornamental plants, and fruit trees.

Additionally, the compounds of the present invention include compounds which have excellent exhibit herbicidal activity on various lowland weeds and which exhibit selectivity toward rice.

Furthermore, the compounds of the present invention can also be applied for controlling weeds in such places as fruit farms, lawns, railway track margins, and vacant lands.

The compounds of the present invention can be used in pure form without adding any other components when applied practically, and also can be used, with an objective to use as agrochemicals, in the form which general agrochemicals may adopt, that is, wettable powder, granules, dusting powder, emulsifiable concentrates, water-soluble powder, suspending agent, flowable, or the like.

As additives and carriers, vegetable powders such as soy flour and wheat flour; fine mineral powder such as diatomaceous earth, apatite, gypsum, talc, bentonite, pyrophyllite, and clay; and organic and inorganic compounds such as sodium benzoate, urea, and sodium sulfate are used when solid formulation is required.

When a liquid formulation is required, petroleum fractions such as kerosene, xylene, and solvent naphtha, and cyclohexane, cyclohexanone, dimethylformamide, dimethyl sulfoxide, alcohol, acetone, trichloroethylene, methyl isobutyl ketone, mineral oil, vegetable oil, water, or the like, are used as a solvent.

Additionally, in order to achieve homogenous and stable foams in these formulations, it is also possible to add surfactants if necessary.

Although surfactants are not particularly limited, examples thereof include, for instance, nonionic surfactants such as alkylphenyl ether where polyoxyethylene is added, alkyl ether where polyoxyethylene is added, higher fatty acid ester where polyoxyethylene is added, sorbitan higher fatty acid ester where polyoxyethylene is added, and tristyryl phenyl ether where polyoxyethylene is added; sulfate ester of alkyl phenyl ether where polyoxyethylene is added, alkyl naphthalene sulfonate, polycarboxylate, lignin sulfonate, formaldehyde condensate of alkyl naphthalene sulfonate, and isobutylene-maleic anhydride copolymer.

Although concentrations of active ingredients in herbicides of the present invention vary depending on the aforementioned forms of formulation, in wettable powder for instance, the concentration of 5 to 90 weight % (hereinafter written simply as "%") and preferably 10 to 85% is used; 3 to 70% and preferably 5 to 60% is used in emulsion; and 0.01 to 50% and preferably 0.05 to 40% is used in granules.

Wettable powder and emulsifiable concentrate obtained in this way, which are diluted to predetermined concentrations by water, are sprayed or mixed in soil as emulsion solution or suspension solution before or after the weed germination. When herbicides of the present invention are practically used, an adequate amount of active ingredients, which is 0.1 g or more per 1 hectare, is applied.

Herbicides of the present invention can also be used by mixing with known fungicides, insecticides, acaricides, other herbicides, plant growth regulators, fertilizers, or the like. In addition, not only labor saving but also a further higher effect can be expected due to synergism with mixed chemicals. In this case, combined use with a two or more of known herbicides is also possible.

Chemicals suitable to be mixed and used with the herbicides of the present invention include anilide herbicides such as diflufenican, picolinafen, and propanil; chloroacetanilide herbicides such as alachlor and pretilachlor; aryloxyalkanoic acid herbicides such as 2,4-D and 2,4-DB; aryloxyphenoxyalkanoic acid herbicides such as diclofop-methyl and fenoxaprop-ethyl; cyclohexanedione herbicides such as sethoxydim and tralkoxydim; carboxylic acid herbicides such as dicamba and picloram; imidazolinone herbicides such as imazaquin and imazethapyr; urea herbicides such as diuron and isoproturon; carbamate herbicides such as chlorpropham and phenmedipham; thiocarbamate herbicides such as thiobencarb and EPTC; dinitroaniline herbicides such as trifluralin and pendimethalin; diphenyl ether herbicides such as acifluorfen and fomesafen; sulfonylurea herbicides such as bensulfuron-methyl and nicosulfuron; pyrimidinyl carboxy herbicides such as pyrithiobac and bispyribac; triazinone herbicides such as metribuzin and metamitron; triazine herbicides such as atrazine and cyanazine; uracil herbicides such as bromacil and lenacil; triazolopyrimidine herbicides such as flumetsulam and penoxsulam; nitrile herbicides such as bromoxynil and dichlobenil; phosphate herbicides such as glyphosate and glufosinate; bipyridilium herbicides such as paraquat and diquat; cyclic imide herbicides such as flumioxazin, flumiclorac-pentyl, and fluthiacet-methyl; benzoylaminopropionate herbicides such as benzoylprop ethyl and furamprop ethyl;

other herbicides such as MSMA, asulam, chloridazon, norflurazon, flurtamone, fluorochloridone, flucarbazone-sodium, propoxycarbazone-sodium, amicarbazone, isoxaben, flupoxam, quinclorac, quinmerac, diflufenzopyr-sodium, oxadiazon, oxadiargyl, piperophos, daimuron, bentazone, benfuresate, ethofumesate, difenzoquat, naproanilide, triazofenamide, clomazone, sulcotrione, mesotrione, pyrasulfotole, isoxaflutole, isoxachlortole, topramezone, dithiopyr, thiazopyr, amitrole, pyrazoxyfen, pylazolynate, benzobicyclon, pyridate, pyridafol, azafenidin, carfentrazone-ethyl, sulfentrazone, pentoxazone, pyraflufen-ethyl, fluazolate, flufenpyr-ethyl, butafenacil, pyraclonil, bencarbazone, cinmethylin, oxaziclomefone, dimethenamide, fentrazamide, indanofan, cafenstrole, pyributycarb, pyrimisulfan, pinoxaden, and KIH-485 (test name).

Moreover, it is also possible to add additives such as vegetable oils and oil concentrates to the composition, which are combined with the above herbicides.

EXAMPLE

Although the present invention will be described further in detail next by use of examples, the scope of the present invention is not limited in any way by the examples below. It should be noted that compound number described below is corresponding to the chemical number in Table 3 below.

Example 1

Production of N'-(2,4-dichlorophenyl)-N,N-(butane-1,4-di-yl)cyanoformamidine (Compound 1-1: Compound Number 178)

4,5-Dichloro-1,2,3-dithiazolium chloride was synthesized by the method described in the literature (Appel, R. et al., Chem. Ber., Vol. 118, 1632 (1985)). By reacting 13.40 g of the obtained 4,5-dichloro-1,2,3-dithiazolium chloride with 10.43 g of 2,4-dichloroaniline with the method described in the above literature, 13.66 g of 4-chloro-5-[(2,4-dichlorophenyl)imino]-5H-1,2,3-dithiazol was obtained (yield 71%).

By reacting 0.50 g of this 4-chloro-5-[(2,4-dichlorophenyl)imino]-5H-1,2,3-dithiazol with 0.37 g of pyrrolidine following the method described in the literature (J. Org. Chem., Vol. 58, 7001 (1993)), 0.20 g of N'-(2,4-dichlorophenyl)-N,N-(butane-1,4-di-yl)cyanoformamidine (1-1) was obtained (yield: 44%).

$\eta_D^{20.7}$ 1.6158

Example 2

Production of N'-(2,4-dichlorophenyl)-N,N-(butane-1,4-di-yl)cyanoformamidine (Compound 1-1: Compound Number 178)

3.76 g of 2,4-dichlorophenyl isocyanate was dissolved in 100 ml of benzene and 1.44 g of pyrrolidine was added to this resulting solution and reacted for 8 hours at room temperature. After completing the reaction, benzene was evaporated under reduced pressure to obtain 5.19 g of N-(2,4-dichlorophenyl)pyrrolidine-1-carboxamide. 0.50 g of the obtained N-(2,4-dichlorophenyl)pyrrolidine-1-carboxamide was dissolved in the mixed solvent composed of 10 ml of acetonitrile and 0.4 ml of carbon tetrachloride and 0.69 g of triphenylphosphine was then added to this resulting solution and the entire mixture was stirred for 1 hour at room temperature. 0.55 g of cuprous cyanide was added to this reaction solution and the entire mixture was refluxed for 2.5 hours. After cooling the reaction solution, insolubles were removed by filtration and the concentrate obtained by evaporating the filtrate under reduced pressure was purified by silica gel column chromatography to obtain 0.39 g of N'-(2,4-dichlorophenyl)-N,N-(butane-1,4-di-yl)cyanoformamidine (1-1) (yield: 72%).

Example 3

Production of N'-(4-chloro-2-fluoro-5-propargyloxyphenyl)-N,N-(butane-1,4-di-yl)cyanoformamidine (Compound 1-2: Compound Number 141)

0.30 g of 4-chloro-2-fluoro-5-propargyloxyphenyl isothiocyanate was dissolved in 5 ml of acetonitrile and 0.09 g of pyrrolidine was then added to this and stirred for 0.5 hours at room temperature. 0.17 g of potassium carbonate and subsequently 0.19 g of methyl iodide were added to this resulting solution and refluxed for 1 hour. After cooling, insolubles were separated by filtration and the resulting filtrate was evaporated under reduced pressure to obtain 0.38 g of N'-(4-chloro-2-fluoro-5-propargyloxyphenyl)-N,N-(butane-1,4-di-yl)methylthioformamide. 0.05 g of N'-(4-chloro-2-fluoro-5-propargyloxyphenyl)-N,N-(butane-1,4-di-yl)methylthioformamide was dissolved in 1 ml of dimethylformamide and 0.02 g of potassium cyanide was then added to the resulting solution and reacted for 5 hours at 60 to 80° C. The resultant solution was purified by preparative thin layer chromatography (PTLC) to obtain 0.02 g of N'-(4-chloro-2-fluoro-5-propargyloxyphenyl)-N,N-(butane-1,4-di-yl)cyanoformamidine (1-2). Yield was 47%. m.p. 88-89° C.

Example 4

Production of N'-(2,4-dichlorophenyl)-N,N-(butane-1,4-di-yl)cyanoformamidine (Compound 1-1: Compound Number 178)

40 ml of acetonitrile solution containing 6.44 g of 2,4-dichlorophenyl isothiocyanate was added dropwise to 40 ml of aqueous solution containing 2.28 g of potassium cyanide at 0° C. over 1 hour. After 3 hours of reaction at room temperature, the reaction solution was poured into a mixed solution of 50 ml of 1N hydrochloric acid and ice. Deposited crystals were separated by filtration and were dried under reduced pressure to obtain 7.14 g of N-(2,4-dichlorophenyl)cyanothioformamide (yield: 97%).

0.50 g of N-(2,4-dichlorophenyl)cyanothioformamide was dissolved in 25 ml of benzene and after adding 0.51 g of phosphorus pentachloride, the resultant solution was refluxed for 2 hours. The reaction solution was vacuum-concentrated and the concentrate was dissolved in 30 ml of acetonitrile, and after the addition of 0.63 g of pyrrolidine at 0° C., reacted for 1.5 hours at room temperature. The concentrate obtained by vacuum concentration of the resulting reaction solution was purified by silica gel column chromatography to obtain 0.08 g of N'-(2,4-dichlorophenyl)-N,N-(butane-1,4-di-yl)cyanoformamidine (1-1) (yield: 13%).

Example 5

Production of 2-[2,4-dichloro-5-(1-ethoxycarbonylethoxy)phenylimino]-2-(pyrrolidine-1-yl)acetamide (Compound 1-3: Compound Number 293)

Apart from the use of 2,4-dichloro-5-hydroxyaniline instead of 2,4-dichloroaniline, N'-(2,4-dichloro-5-hydroxyphenyl)-N,N-(butane-1,4-di-yl)cyanoformamidine was obtained by the same manner to that in Example 1. 3.22 g of N'-(2,4-dichloro-5-hydroxyphenyl)-N,N-(butane-1,4-di-yl)cyanoformamidine was dissolved in 30 ml of diethyl ether and 30 ml of 10% sodium hydroxide solution was then added and the resulting solution was stirred for 1 hour at room temperature. The aqueous layer was separated and after adding concentrated hydrochloric acid thereto with cooling by ice-water, benzene was added resulting in the deposition of white solid matter. By removing crystals by filtration, 2.53 g of 2-(2,4-dichloro-5-hydroxyphenylimino)-2-(pyrrolidine-1-yl)acetamide was obtained (yield 83%).

0.5 g of the obtained 2-(2,4-dichloro-5-hydroxyphenylimino)-2-(pyrrolidine-1-yl)acetamide was dissolved in 50 ml of acetonitrile and 0.25 g of potassium carbonate was then added and the entire mixture was heated to reflux for 1 hour. 0.37 g of ethyl 2-bromopropionate was added to the resulting reaction solution and further heated to reflux for 1 hour. Insolubles were removed from the resultant reaction solution by filtration and the concentrate obtained by evaporating solvents from the filtrate by evaporation under reduced pressure was purified by silica gel column chromatography to obtain 0.37 g of 2-[2,4-dichloro-5-(1-ethoxycarbonylethoxy)phenylimino]-2-(pyrrolidine-1-yl)acetamide (1-3) (yield 55%). m.p. 160-163° C.

Example 6

Production of 1-ethoxy-2-methyl-1-oxopropane-2-yl-5-(2-acetamide-1-(pyrrolidine-1-yl)-2-thioxoethylideneamino)-2-chloro-4-fluorobenzoate (Compound 1-4: Compound Number 201)

Apart from the use of 2-fluoro-4-chloro-5-(1-ethoxycarbonyl-1-methylethoxycarbonyl)aniline instead of 2,4-dichloroaniline, 1-ethoxy-2-methyl-1-oxopropane-2-yl-2-chloro-5-[cyano(pyrrolidine-1-yl)methyleneamino]-4-fluorobenzoate was obtained by the same manner to that in Example 1. 1.95 g of 1-ethoxy-2-methyl-1-oxopropane-2-yl-2-chloro-5-[cyano(pyrrolidine-1-yl)methyleneamino]-4-fluorobenzoate was dissolved in a mixture of 3 ml of pyridine and 0.48 g of triethylamine and hydrogen sulfide was then introduced to the resulting solution at room temperature. After verifying the completion of the reaction by thin layer chromatography, the reaction solution was poured into ice-cold water and extracted with ethyl acetate. The organic layer was washed with saturated saline and dried with anhydrous magnesium sulfate. 2.06 g of a crude product of 1-ethoxy-2-methyl-1-oxopropane-2-yl-5-(2-amino-1-(pyrrolidine-1-yl)-2-thioxoethylideneamino)-2-chloro-4-fluorobenzoate was obtained by evaporating solvents under reduced pressure.

0.23 g of the obtained 1-ethoxy-2-methyl-1-oxopropane-2-yl-5-(2-amino-1-(pyrrolidine-1-yl)-2-thioxoethylideneamino)-2-chloro-4-fluorobenzoate was dissolved in 10 ml of acetone and after the addition of 0.09 g of pyridine, a solution of 5 ml of acetone containing 0.09 g of acetylchloride was added dropwise thereto at room temperature over 20 minutes. After refluxing the reaction solution for 2 hours, the resulting solution was poured into ice-cold water and extracted with chloroform. The organic layer was washed with saturated saline, dried with anhydrous magnesium sulfate, and filtered. The concentrate obtained by evaporating solvents from the filtrate under reduced pressure was purified by silica gel column chromatography to obtain 0.06 g of 1-ethoxy-2-methyl-1-oxopropane-2-yl-5-(2-acetamide-1-(pyrrolidine-1-yl)-2-thioxoethylideneamino)-2-chloro-4-fluorobenzoate (1-4) (yield 23%). Amorphous.

Example 7

Production of 2-(4-chloro-2-fluoro-5-propargyloxyphenylimino)-2-(pyrrolidine-1-yl)acetaldehyde O-methyloxime (Compound 1-5: Compound Number 190)

6 ml of aqueous solution containing 4.19 g of O-methylhydroxylamine hydrochloride was added to 6 ml of aqueous solution containing 4.67 g of glyoxylic acid monohydrate. 5 ml of aqueous solution containing 2.0 g of sodium hydroxide was added dropwise to the obtained solution under ice-cooling and after the addition, the resulting solution was stirred at room temperature for 1.5 hours. The resultant reacting solution was extracted by the addition of ethyl acetate. After washing with saturated saline, the organic layer was dried with anhydrous magnesium sulfate and filtered. 4.62 g of 2-(methoxyimino)acetate was obtained by evaporating solvents from the filtrate under reduced pressure (yield 89%).

0.58 g of the obtained 2-(methoxyimino)acetate was dissolved in 30 ml of xylene and 1.00 g of 4-chloro-2-fluoro-5-propargyloxyaniline was added thereto. 0.17 ml of phosphorus trichloride was then added to the resulting solution and the entire mixture was heated to reflux for 1 hour. After cooling the resulting reaction solution, sodium bicarbonate water was added thereto and the resultant solution was then extracted with ethyl acetate. After washing with saturated saline, the organic layer was dried with anhydrous magnesium sulfate and filtered. The concentrate obtained by evaporating solvents from the filtrate under reduced pressure was washed with a mixed solvent of ether-normal hexane to obtain 0.70 g of N-(4-chloro-2-fluoro-5-propargyloxyphenyl)-2-(methoxyimino)acetamide (yield 49%).

0.42 g of the obtained N-(4-chloro-2-fluoro-5-propargyloxyphenyl)-2-(methoxyimino)acetamide was dissolved in 30 ml of benzene and after the addition of 0.36 g of phosphorus pentachloride, the resulting solution was refluxed for 4 hours. The concentrate obtained by concentrating the resulting reaction solution under reduced pressure was dissolved in 20 ml of dichloromethane and 0.32 g of pyrrolidine was added dropwise thereto at room temperature and the resultant solution was stirred at room temperature for 1 hour. The concentrate obtained by evaporating solvents from the resulting reaction solution under reduced pressure was purified by silica gel column chromatography to obtain 0.32 g of 2-(4-chloro-2-fluoro-5-propargyloxyphenylimino)-2-(pyrrolidine-1-yl)acetaldehyde O-methyloxime (1-5) (yield 64%). m.p. 73-75° C.

Example 8

Production of N'-(4-chloro-2-fluoro-5-propargyloxyphenyl)-N,N-(butane-1,4-di-yl)-4,5-dihydroisooxazole-3-carboxyamidine (Compound 1-6: Compound Number 207)

0.63 g of 4,5-dihydroisooxazole-3-carboxylic acid was dissolved in 40 ml of dichloromethane and then 0.66 ml of oxalyl chloride and subsequently a catalytic amount of N,N-dimethylformamide were added thereto at room temperature and the entire mixture was stirred at room temperature for 45 minutes. 0.77 g of 4,5-dihydroisooxazole-3-carboxylic acid chloride was obtained by evaporating solvents from the resulting reaction solution under reduced pressure.

On the other hand, 1.00 g of 4-chloro-2-fluoro-5-propargyloxyaniline was dissolved in 30 ml of dichloromethane and 0.53 g of pyridine was added thereto. 20 ml of dichloromethane solution containing 0.77 g of 4,5-dihydroisooxazole-3-carboxylic acid chloride, which was obtained beforehand, was then added dropwise to the resulting solution with ice-cooling over 10 minutes and after the addition was completed, the resultant solution was stirred at room temperature for 2 hours. The organic layer was separated from the resulting reaction solution, sequentially washed with 1N hydrochloric acid, 10% sodium bicarbonate water, and saturated saline, dried with anhydrous magnesium sulfate, and then filtered. The concentrate obtained by evaporating solvents from the filtrate under reduced pressure was washed with a mixed solvent of ether-normal hexane to obtain 1.43 g of N-(4-chloro-2-fluoro-5-propargyloxyphenyl)-4,5-dihydroisooxazole-3-carboxyamide (yield 88%).

1.27 g of the obtained N-(4-chloro-2-fluoro-5-propargyloxyphenyl)-4,5-dihydroisooxazole-3-carboxyamide was reacted with phosphorus pentachloride and subsequently with pyrrolidine in the same manner as that in Example 7 to obtain 1.42 g of N'-(4-chloro-2-fluoro-5-propargyloxyphenyl)-N,N-(butane-1,4-di-yl)-4,5-dihydroisooxazole-3-carboxyamidine (1-6) (yield 94%). m.p. 79-81° C.

Specific examples of the compound (1) produced as described so far are shown in Table 3 below.

In Table 3, when there is a description in the section of physical constant "132-133", for example, it shows that the melting temperature (° C.) is between 132° C. and 133° C. Likewise, "22.4° C. 1.5928" shows a refractive index at 22.4° C., "amorphous" shows an amorphous state, and "viscous oil" shows a viscous-oil state.

In addition, abbreviations of substituents used in Table 3 are those as shown in Tables below showing examples of chemical formulae and substituents.

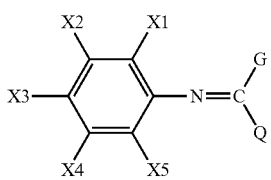

| Substituent (N, O, S, heterocycle) | |
|---|---|
| No. | Structural formula |
| N001 | ※—NH—CH₂—C≡CH |
| N002 | ※—NH—COCF₃ |
| N003 | ※—NH—SO₂CH₃ |
| N004 | ※—N(CH₃)—SO₂CH₃ |
| N005 | ※—N=C(CN)-pyrrolidinyl |
| N006 | ※—N=C(CF₃)(CN) |
| N007 | ※—N(C(=O)NHCH₃) |
| S001 | ※—S—CH(CH₃)₂ |
| S002 | ※—S—C≡C—CH₃ |
| S003 | ※—S—CH(CH₃)—C≡CH |
| S004 | ※—S—COCH₃ |
| S005 | ※—S(=O)—CH(CH₃)₂ |

-continued

| Substituent (N, O, S, heterocycle) | |
|---|---|
| No. | Structural formula |
| S006 | ※—S(=O)₂—NH—CH₂—CH=CH₂ |
| S007 | ※—S(=O)₂—CH(CH₃)₂ |
| S008 | ※—S—CH₂—C≡CH |
| S009 | ※—S(=O)₂—CH₂—C≡CH |
| T001 | ※—O—CH(CH₃)₂ |
| T002 | ※—O—CH₂CH=CH₂ |
| T003 | ※—O—CH₂—C≡CH |
| T004 | ※—O—CH₂—CBr=CH₂ |
| T005 | ※—O—CH₂—C(CH₃)=CH₂ |
| T006 | ※—O—CH(CH₃)—C≡CH |
| T007 | ※—O—CF=CF—CH=CH₂ |
| T008 | ※—O—CH₂—C₆H₅ |
| T009 | ※—O—CH₂-(6-chloropyridin-3-yl) |
| T010 | ※—O—cyclopentyl |
| T011 | ※—O—C₆H₄—NO₂ (para) |
| T012 | ※—O—C₆H₄—NH—S(=O)₂CH₃ (ortho) |

| No. | Structural formula |
|---|---|
| T013 | ※—O—C₆H₄—O—C(=O)—O—CH₃ (2-methoxycarbonyloxyphenoxy) |
| T014 | ※—O—C₆H₄—O—CH₂—C₆H₅ (2-benzyloxyphenoxy) |
| T015 | ※—O—C₆H₄—O—CH₂—C(=O)—N(CH₃)₂ |
| T016 | ※—O—(2-pyrimidinyl) |
| T017 | ※—O—(3-nitro-2-pyridyl) |
| T018 | ※—O—CH₂—O—CH₃ |
| T019 | ※—O—CH₂—C≡C—CH₃ |
| T020 | ※—O—C(CH₃)₂—C≡CH |
| T021 | ※—O—CH₂—C≡N |
| T022 | ※—O—CH₂CH₃ |
| T023 | ※—O—CH₂CH₂CH₃ |
| T024 | ※—O—CH₂CH₂CH₂CH₃ |
| T025 | ※—O—CH₂—O—CH₂CH₂CH₃ |
| T026 | ※—O—CH₂—C≡C—Si(CH₃)₃ |
| T027 | ※—O—CH₂—CH(CH₃)—O—CH₃ |
| T028 | ※—O—C₆H₄—O—CH₂—C(=O)—O—CH₃ |
| T029 | ※—O—C₆H₄—O—CH₂—C≡CH |
| T030 | ※—O—CH(CH₃)—CN |
| T031 | ※—O—CH₂—O—CH₂—O—CH₃ |
| T032 | ※—O—CH₂—O—C₆H₄—Cl |
| T033 | ※—O—CH₂—O—CH₂—C₆H₅ |
| T034 | ※—O—CH₂CH₂—OCH₃ |
| T035 | ※—O—CH₂CH₂—OC₆H₅ |
| T036 | ※—O—CH₂CH₂—O—CH₂—C₆H₅ |
| T037 | ※—O—CH₂—OC₂H₅ |
| T038 | ※—O—CH₂—CH=CH—Cl (cis) |
| T039 | ※—O—CH₂—CH=CH—Cl (trans) |
| T040 | ※—O—CH₂-(3-furyl) |
| T041 | ※—O—CH₂-(2-furyl) |
| T042 | ※—O—CH₂-(4,5-dihydroisoxazol-3-yl) |
| T043 | ※—O—CH₂—C≡C—CN |
| T044 | ※—O—CH₂—O—CH₃ |
| T045 | ※—O—CH₃ |
| T046 | ※—O—CH₂—CF₃ |
| T047 | ※—O—CH₂CH₂—CH=CF₂ |

| No. | Structural formula |
|---|---|
| T048 | 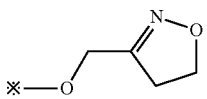 |
| T049 | 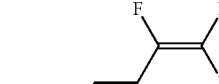 |
| T050 | 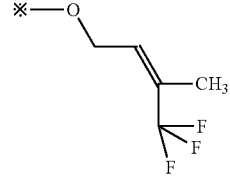 |
| T051 | 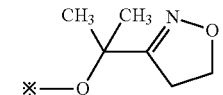 |
| T052 | 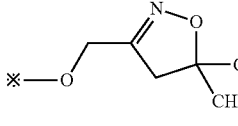 |
| T053 | 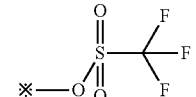 |
| T054 | 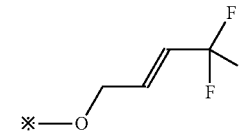 |
| T055 | 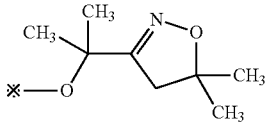 |
| T056 | 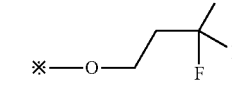 |
| T057 | 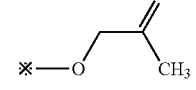 |
| T058 | 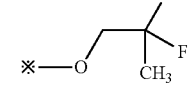 |
| T059 | 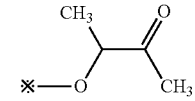 |
| T060 | 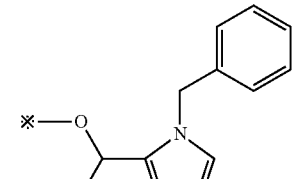 |
| T061 | 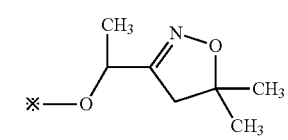 |
| T062 | 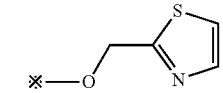 |
| T063 | 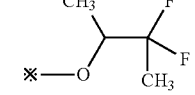 |
| T064 | 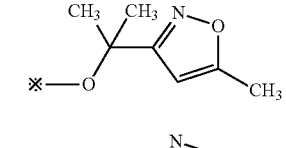 |
| T065 | 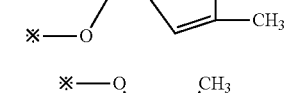 |
| T066 | 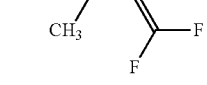 |
| T067 | 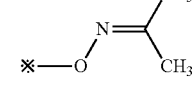 |
| T068 | 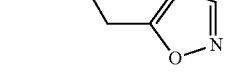 |
| T069 | 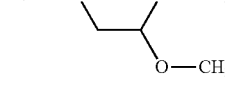 |
| T070 |  |

-continued
| No. | Structural formula |
|---|---|
| T071 | 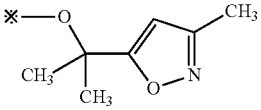 |
| T072 | 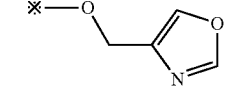 |
| T073 | 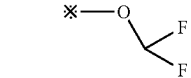 |
| T074 | 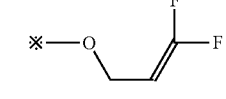 |
| T075 | 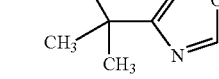 |
| T076 | 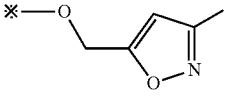 |
| T077 | 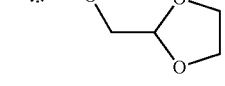 |
| T078 | 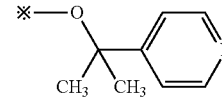 |
| T079 | 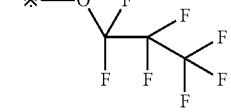 |
| T080 | 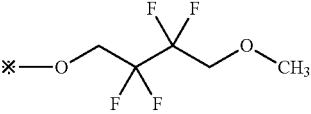 |
| H001 | 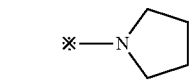 |
| H002 | 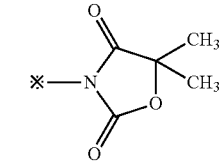 |
-continued
| No. | Structural formula |
|---|---|
| H003 | 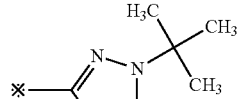 |
| H004 | 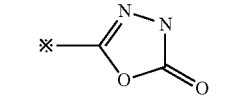 |
| H005 | 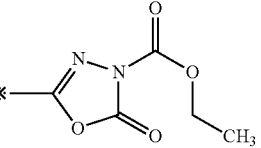 |
| H006 | 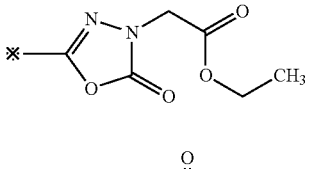 |
| H007 | 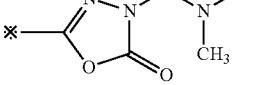 |
| H008 | 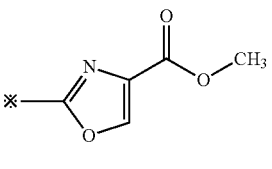 |
| H009 | 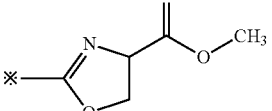 |
| H010 | 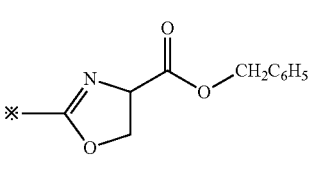 |
| H011 | 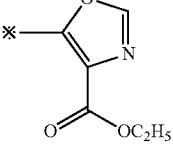 |

| Substituent (N, O, S, heterocycle) | |
|---|---|
| No. | Structural formula |
| H012 | ※—[5-substituted-1,2,4-oxadiazol-3-yl]—C(O)OC₂H₅ |
| H013 | ※—[2-substituted-oxazol-4-yl]—C(O)OH |
| H014 | ※—[2-substituted-4,5-dihydrooxazol-4-yl]—C(O)NHC₂H₅ |
| H015 | ※—[2-substituted-oxazol-4-yl]—C(O)NHC₂H₅ |
| H016 | ※—[2-substituted-oxazol-4-yl]—C(O)N(CH₃)₂ |
| H017 | ※—[2-substituted-oxazol-4-yl]—C(O)OC₂H₅ |
| H018 | ※—[2-substituted-oxazol-4-yl]—C(O)OCH₂C₆H₅ |
| C001 | ※—C(O)—CH—(C(O)OC₂H₅)₂ |
| C002 | ※—C(O)—S—C(CH₃)(H)—C(O)OC₂H₅ |
| C003 | ※—C(O)—O—N=C(NH₂)—C(O)OC₂H₅ |

| | | Substituent (X11) | | | | | | |
|---|---|---|---|---|---|---|---|---|
| | | ※—A1$_{m1}$—C(=O)—Z1 | | X12 ※—A2$_{m2}$—Y(—Z2) | | | X13 ※—A3$_{m3}$—C(=O)—Z3 | |
| No. | (A1)$_{m1}$ | Z1 | (A2)$_{m2}$ | Y | Z2 | (A3)$_{m3}$ | Z3 |
| X101 | m1 = 0 | ※—OH | — | — | — | — | — |
| X102 | m1 = 0 | ※—OCH$_3$ | — | — | — | — | — |
| X103 | m1 = 0 | ※—OC$_2$H$_5$ | — | — | — | — | — |
| X104 | m1 = 0 | ※—O—CH(CH$_3$)(CH$_3$) | — | — | — | — | — |
| X105 | m1 = 0 | ※—OCH$_2$—CH=CH$_2$ | — | — | — | — | — |
| X106 | m1 = 0 | ※—O—C(CH$_3$)(CH$_3$)(CN) | — | — | — | — | — |
| X107 | m1 = 0 | ※—O—C(CH$_3$)(CH$_3$)(CH$_2$OH) | — | — | — | — | — |
| X108 | m1 = 0 | ※—O—C(CH$_3$)(CH$_3$)(CF$_3$) | — | — | — | — | — |
| X109 | m1 = 0 | ※—O—C(CH$_3$)(OC$_2$H$_5$)—C(CH$_3$)(OC$_2$H$_5$) | — | — | — | — | — |
| X110 | m1 = 0 | ※—OCH$_2$—C(CH$_3$)(CH$_3$)(OH) | — | — | — | — | — |

-continued

| No. | Substituent (X11) | | | | | | | |
|---|---|---|---|---|---|---|---|---|
| | (A1)$_{m1}$ | Z1 | X12 [∗—A2$_{m2}$]Y—Z2 | | | X13 [∗—A3$_{m3}$]—C(=O)—Z3 | | |
| | | | (A2)$_{m2}$ | Y | Z2 | (A3)$_{m3}$ | | Z3 |

| No. | (A1)$_{m1}$ | Z1 | (A2)$_{m2}$ | Y | Z2 | (A3)$_{m3}$ | Z3 |
|---|---|---|---|---|---|---|---|
| X111 | m1 = 0 | ∗—O—C(CH$_3$)$_2$—CH(OH)CH$_3$ | — | — | — | — | — |
| X112 | m1 = 0 | ∗—O—CH$_2$—C$_6$H$_5$ | — | — | — | — | — |
| X113 | m1 = 0 | ∗—O—C(CH$_3$)$_2$-(4,5-dihydroisoxazol-3-yl) | — | — | — | — | — |
| X114 | m1 = 0 | ∗—O—C(CH$_3$)$_2$-(4,5-dihydrooxazol-2-yl) | — | — | — | — | — |
| X115 | m1 = 0 | ∗—O—C(CH$_3$)$_2$-(oxazol-5-yl with 4-tolylsulfonyl) | — | — | — | — | — |
| X116 | m1 = 0 | ∗—NH—CH(CH$_3$)$_2$ | — | — | — | — | — |

| No. | (A1)$_{m1}$ | Z1 | (A2)$_{m2}$ | Y | Z2 | (A3)$_{m3}$ | Z3 |
|---|---|---|---|---|---|---|---|
| X117 | m1 = 0 | 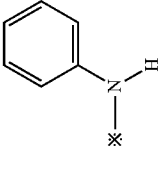 | — | — | — | — | — |
| X118 | m1 = 0 | 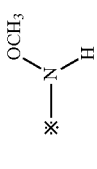 | — | — | — | — | — |
| X119 | m1 = 0 | 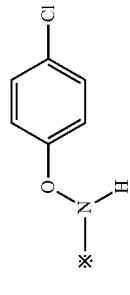 | — | — | — | — | — |
| X120 | m1 = 0 | 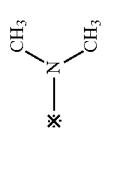 | — | — | — | — | — |
| X121 | m1 = 0 | 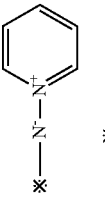 | — | — | — | — | — |
| X122 | ※—CH$_2$—CHCl— | ※—OC$_2$H$_5$ | — | — | — | — | — |
| X123 | ※—CH—CCl— | ※—OC$_2$H$_5$ | — | — | — | — | — |
| X124 | ※—CH$_2$—O—CH(CH$_3$)— | ※—OC$_2$H$_5$ | — | — | — | — | — |
| X125 | ※—NH— | 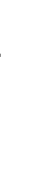 | — | — | — | — | — |

-continued

| No. | (A1)$_{m1}$ | Z1 | Substituent (X11)<br>(A2)$_{m2}$ | Y | Z2 | (A3)$_{m3}$ | Z3 |
|---|---|---|---|---|---|---|---|
| X126 | ✳—NH— | pyrrolidinyl | — | — | — | — | — |
| X127 | ✳—N(CH$_2$—C≡CH)— | —C(CH$_3$)$_2$—O—✳ | — | — | — | — | — |
| X128 | ✳—NH—CH$_2$— | ✳—OC$_2$H$_5$ | — | — | — | — | — |
| X129 | ✳—O—CH$_2$— | ✳—OH | — | — | — | — | — |
| X130 | ✳—O—CH$_2$— | ✳—OC$_2$H$_5$ | — | — | — | — | — |
| X131 | ✳—O—CH$_2$— | ✳—OCH(CH$_3$)$_2$ | — | — | — | — | — |
| X132 | ✳—O—CH$_2$— | ✳—OCH$_2$—C≡CH | — | — | — | — | — |
| X133 | ✳—O—CH$_2$— | ✳—O-cyclopentyl | — | — | — | — | — |
| X134 | ✳—O—CH$_2$— | ✳—CH(CH$_3$)—NH— | — | — | — | — | — |
| X135 | ✳—O—CH(CH$_3$)— | ✳—OCH$_3$ | — | — | — | — | — |
| X136 | ✳—O—CH(CH$_3$)— | ✳—OC$_2$H$_5$ | — | — | — | — | — |

-continued

| No. | Substituent (X11) | | | | | | | |
|---|---|---|---|---|---|---|---|---|
| | $(A1)_{m1}$ | X12 $\left[\begin{array}{c}\text{O}\\\text{*}—A1_{m1}—\end{array}\right]$ Z1 | $(A2)_{m2}$ | X12 $\left[\begin{array}{c}\text{*}—A2_{m2}—\end{array}\right]$ Y | Y $\begin{array}{c}\text{Y}\\|\\\text{Z2}\end{array}$ | Z2 | X13 $\left[\begin{array}{c}\text{O}\\\text{*}—A3_{m3}—\end{array}\right]$ Z3 $(A3)_{m3}$ | Z3 |
| X137 | *—O—C(CH₃)₂—CH₃ | *—OH | — | — | — | — | — | — |
| X138 | *—O—C(CH₃)₂—CH₃ | *—OC₂H₅ | — | — | — | — | — | — |
| X139 | *—O—C(CH₃)₂—CH₃ | *—O—C(CH₃)₂—CH₃ | — | — | — | — | — | — |
| X140 | *—O—C(CH₃)₂—CH₃ | *—N(CH₃)₂ | — | — | — | — | — | — |
| X141 | *—O—CH(CH₂)CH₂ (cyclopropyl) | *—OCH₃ | — | — | — | — | — | — |
| X142 | *—S—CH₂— | *—OC₂H₅ | — | — | — | — | — | — |
| X143 | *—S—CH₂— | *—O—CH(CH₃)CH₃ | — | — | — | — | — | — |
| X144 | *—S—CH₂— | *—OCH₂—CH=CH₂ | — | — | — | — | — | — |
| X145 | *—S—CH(CH₃)—* | *—OCH₃ | — | — | — | — | — | — |

-continued
| No. | Substituent (X11) | | | | | | | |
|---|---|---|---|---|---|---|---|---|
| | X12 $\left[ * \!\!- A1_{m1} \overset{\displaystyle O}{-}\!\! Z1 \right]$ | | X12 $\left[ * \!\!- A2_{m2} \overset{\displaystyle Y}{-}\!\! Z2 \right]$ | | | X13 $\left[ * \!\!- A3_{m3} \overset{\displaystyle O}{-}\!\! Z3 \right]$ | | |
| | $(A1)_{m1}$ | Z1 | $(A2)_{m2}$ | Y | Z2 | $(A3)_{m3}$ | Z3 | |
| X146 |  |  | — | — | — | — | — | |
| X147 |  | | — | — | — | — | — | |
| X148 | m1 = 0 |  | — | — | — | — | — | |
| X149 | m1 = 0 |  | — | — | — | — | — | |
| X150 | m1 = 0 | | — | — | — | — | — | |
| X151 | m1 = 0 | | — | — | — | — | — | |
| X152 | m1 = 0 | | — | — | — | — | — | |
| X153 | m1 = 0 | | — | — | — | — | — | |
| X201 | m1 = 0 |  |  | O |  | — | — | |
| X202 | m1 = 0 | 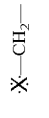 | 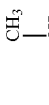 | O | 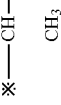 | — | — | |
| X203 | m1 = 0 | |  | O | 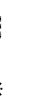 | — | — | |
| X204 | m1 = 0 | 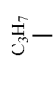 |  | O | 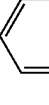 | — | — | |
| X205 | m1 = 0 | 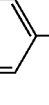 | 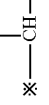 | O |  | — | — | |

-continued

| No. | (A1)$_{m1}$ | Z1 | (A2)$_{m2}$ | Y | Z2 | (A3)$_{m3}$ | Z3 |
|---|---|---|---|---|---|---|---|
| X206 | m1 = 0 | ✳—OX12 | ✳—CH(CH$_3$)$_2$ | O | ✳—OH | — | — |
| X207 | m1 = 0 | ✳—O—X12 | ✳—CH(CH$_3$)$_2$ | O | ✳—OCH$_3$ | — | — |
| X208 | m1 = 0 | ✳—OX12 | ✳—C(CH$_3$)$_3$ | O | ✳—OC$_2$H$_5$ | — | — |
| X209 | m1 = 0 | ✳—OX12 | ✳—C(CH$_3$)$_3$ | O | ✳—OCH(CH$_3$)$_2$ | — | — |
| X210 | m1 = 0 | ✳—OX12 | ✳—C(CH$_3$)$_3$ | O | ✳—OCH$_2$—CH=CH$_2$ | — | — |
| X211 | m1 = 0 | ✳—NHX12 | ✳—C(CH$_3$)$_3$ | O | ✳—OC$_2$H$_5$ | — | — |
| X212 | m1 = 0 | ✳—OX12 | ✳—C(CH$_3$)$_3$ | O | ✳—NH$_2$ | — | — |

-continued

| No. | Substituent (X11) | | | | | | |
|---|---|---|---|---|---|---|---|
| | $(A1)_{m1}$ | Z1 | $(A2)_{m2}$ | Y | Z2 | $(A3)_{m3}$ | Z3 |
| | ※—A1—$\overset{\displaystyle O}{\underset{\displaystyle \|}{C}}$—Z1 $_{m1}$ | | X12 $\left[\text{※—A2}_{m2}\overset{Y}{-}\text{Z2}\right]$ | | | X13 $\left[\text{※—A3}_{m3}\overset{\displaystyle O}{\underset{\displaystyle \|}{C}}\text{—Z3}\right]$ | |
| X213 | m1 = 0 | ※—OX12 | ※—C(CH₃)(CH₃)(CH₃) | O | ※—CH(CH₃)(H) | — | — |
| X214 | m1 = 0 | ※—OX12 | ※—C(CH₃)(CH₃)(CH₃) | O | ※—CH(C₂H₅)(H) | — | — |
| X215 | m1 = 0 | ※—OX12 | ※—C(CH₃)(CH₃)(CH₃) | O | ※—N(CH₂CH₂Cl)(H) | — | — |
| X216 | m1 = 0 | ※—OX12 | ※—C(CH₃)(CH₃)(CH₃) | O | ※—N(C₃H₇)(H) | — | — |
| X217 | m1 = 0 | ※—OX12 | ※—C(CH₃)(CH₃)(CH₃) | O | ※—N(CH(CH₃)(H₃C))(H) | — | — |
| X218 | m1 = 0 | ※—OX12 | ※—C(CH₃)(CH₃)(CH₃) | O | ※—N(CH₂—CH=CH₂)(H) | — | — |
| X219 | m1 = 0 | ※—OX12 | ※—C(CH₃)(CH₃)(CH₃) | O | ※—N(CH₂—C≡CH)(H) | — | — |

-continued
| | Substituent (X11) | | | | | |
|---|---|---|---|---|---|---|
| No. | (A1)$_{m1}$  | Z1 | (A2)$_{m2}$  | Y | Z2 | (A3)$_{m3}$  | Z3 |
| X220 | m1 = 0 | ✻—OX12 |  | O |  | — | — |
| X221 | m1 = 0 | ✻—OX12 |  | O |  CH$_2$CH$_2$OC$_2$H$_5$ | — | — |
| X222 | m1 = 0 | ✻—OX12 |  | O |  | — | — |
| X223 | m1 = 0 | ✻—OX12 |  | O |  | — | — |
| X224 | m1 = 0 | ✻—OX12 |  | O |  OCH$_3$ | — | — |
| X225 | m1 = 0 | ✻—OX12 |  | O |  | — | — |

| No. | (A1)$_{m1}$ | Z1 | (A2)$_{m2}$ | Y | Z2 | (A3)$_{m3}$ | Z3 |
|---|---|---|---|---|---|---|---|
| X226 | m1 = 0 | ✱—OX12 | ✱—C(CH₃)₂—CH₃ | O | ✱—N(CH₃)CH₃ | — | — |
| X227 | m1 = 0 | ✱—OX12 | ✱—C(CH₃)₂—CH₃ | O | ✱—N(C₂H₅)C₂H₅ | — | — |
| X228 | m1 = 0 | ✱—OX12 | ✱—C(CH₃)₂—CH₃ | O | ✱—N(C₃H₇)CH₃ | — | — |
| X229 | m1 = 0 | ✱—OX12 | ✱—C(CH₃)₂—CH₃ | O | ✱—N(CH₂—CH=CH₂)CH₃ | — | — |
| X230 | m1 = 0 | ✱—OX12 | ✱—C(CH₃)₂—CH₃ | O | ✱—N(CH₂—C≡CH)CH₃ | — | — |
| X231 | m1 = 0 | ✱—OX12 | ✱—C(CH₃)₂—CH₃ | O | ✱—N(CH₂CN)CH₃ | — | — |
| X232 | m1 = 0 | ✱—OX12 | ✱—C(CH₃)₂—CH₃ | O | ✱—N(pyrrolidinyl) | — | — |

| No. | (A1)$_{m1}$ | Z1 | (A2)$_{m2}$ | Y | Z2 | (A3)$_{m3}$ | Z3 |
|---|---|---|---|---|---|---|---|
| X233 | m1 = 0 | ※—OX12 | C(CH$_3$)$_2$ | O | N-morpholinyl | — | — |
| X234 | m1 = 0 | ※—OX12 | C(CH$_3$)$_2$ | O | ※—H | — | — |
| X235 | m1 = 0 | ※—OX12 | C(CH$_3$)$_2$ | O | ※—CH$_3$ | — | — |
| X236 | m1 = 0 | ※—OX12 | C(CH$_3$)$_2$ | O | ※—C$_2$H$_5$ | — | — |
| X237 | m1 = 0 | ※—OX12 | C(CH$_3$)$_2$ | O | ※—CH$_2$SCH$_3$ | — | — |
| X238 | m1 = 0 | ※—OX12 | C(CH$_3$)$_2$ | O | ※—CH$_2$S—C(=NH)—CH$_3$ | — | — |
| X239 | m1 = 0 | ※—OX12 | C(CH$_3$)$_2$ | NOH | ※—H | — | — |

-continued

| | | Substituent (X11) | | | | | |
|---|---|---|---|---|---|---|---|
| No. | $(A1)_{m1}$ | Z1 $\begin{bmatrix} * \!-\! A1_{m1} \!-\! \overset{O}{\underset{\|}{C}} \!-\! Z1 \end{bmatrix}$ | $(A2)_{m2}$ | Y | Z2 $X12 \begin{bmatrix} * \!-\! A2_{m2} \!-\! \overset{Y}{\underset{\|}{C}} \!-\! Z2 \end{bmatrix}$ | $(A3)_{m3}$ | Z3 $X13 \begin{bmatrix} * \!-\! A3_{m3} \!-\! \overset{O}{\underset{\|}{C}} \!-\! Z3 \end{bmatrix}$ |
| X240 | m1 = 0 | *—OX12 | $\underset{*}{\overset{CH_3}{\underset{CH_3}{|}}}\!\!\!C\!\!\!-$ | $NOCH_3$ | *—H | — | — |
| X241 | m1 = 0 | *—OX12 | $\underset{*}{\overset{CH_3}{\underset{CH_3}{|}}}\!\!\!C\!\!\!-$ | $NOC_2H_5$ | *—$CH_3$ | — | — |
| X242 | m1 = 0 | *—OX12 | $\underset{*}{\overset{CH_3}{\underset{CH_3}{|}}}\!\!\!C\!\!\!-$ | $NOCH_2\!-\!CH\!=\!CHCl$ | *—H | — | — |
| X243 | m1 = 0 | *—OX12 | $\underset{*}{\overset{CH_3}{\underset{CH_3}{|}}}\!\!\!C\!\!\!-$ | $NNHCOOC_2H_5$ | *—H | — | — |
| X244 | m1 = 0 | *—OX12 | $\underset{*}{\overset{H_2C\!-\!CH_2}{\diagdown\!\!\diagup}}\!\!C\!\!\!-$ | O | *—OH | — | — |
| X245 | m1 = 0 | *—OX12 | $\underset{*}{\overset{H_2C\!-\!CH_2}{\diagdown\!\!\diagup}}\!\!C\!\!\!-$ | O | *—$OC_2H_5$ | — | — |
| X246 | m1 = 0 | *—OX12 | $\underset{*}{\overset{H_2C\!-\!CH_2}{\diagdown\!\!\diagup}}\!\!C\!\!\!-$ | O | $\underset{*}{N}\!\!\diagup\!\!\!\overset{C_2H_5}{\diagdown\! H}$ | — | — |
| X247 | m1 = 0 | *—OX12 | $\underset{*}{\overset{H_2C\!-\!CH_2}{\diagdown\!\!\diagup}}\!\!C\!\!\!-$ | O | $\underset{*}{N}\!\!\diagup\!\!\!\overset{CH_3}{\diagdown\! CH_3}$ | — | — |

-continued

| No. | Substituent (X11) | | | | | | |
|---|---|---|---|---|---|---|---|
| | $(A1)_{m1}$ | X12 [✻—A1$_{m1}$—C(=O)—Z1] Z1 | $(A2)_{m2}$ | Y | Z2 | $(A3)_{m3}$ | X13 [✻—A3$_{m3}$—C(=O)—Z3] Z3 |
| X248 | m1 = 0 | ✻—OX12 | ✻—C(CF$_3$)(CH$_3$)— | O | ✻—OH | — | — |
| X249 | m1 = 0 | ✻—OX12 | ✻—C(CF$_3$)(CH$_3$)— | O | ✻—OC$_2$H$_5$ | — | — |
| X250 | m1 = 0 | ✻—OX12 | ✻—C(CF$_3$)(CH$_3$)— | O | ✻—N(C$_2$H$_5$)(CH$_3$) | — | — |
| X251 | m1 = 0 | ✻—OX12 | ✻—C(CF$_3$)(CH$_3$)— | O | ✻—N(CH$_3$)(CH$_3$) | — | — |
| X252 | m1 = 0 | ✻—OX12 | ✻—C(C$_2$H$_5$)(CH$_3$)— | O | ✻—OH | — | — |
| X253 | m1 = 0 | ✻—OX12 | ✻—C(C$_2$H$_5$)(CH$_3$)— | O | ✻—OC$_2$H$_5$ | — | — |
| X254 | m1 = 0 | ✻—OX12 | ✻—C(C$_2$H$_5$)(CH$_3$)— | O | ✻—N(C$_2$H$_5$)(H) | — | — |

-continued

| No. | Substituent (X11) | | | | | | | |
|---|---|---|---|---|---|---|---|---|
| | $X12\left[\ast-A1_{m1}-\overset{\overset{O}{\|}}{C}-Z1\right]$ | | $X12\left[\ast-A2_{m2}-\overset{Y}{\overset{\|}{C}}-Z2\right]$ | | $X13\left[\ast-A3_{m3}-\overset{\overset{O}{\|}}{C}-Z3\right]$ | | | |
| | $(A1)_{m1}$ | Z1 | $(A2)_{m2}$ | Y | Z2 | $(A3)_{m3}$ | Z3 |
| X255 | m1 = 0 | ✻—OX12 | ✻—C(C₂H₅)(CH₃)(C₂H₅) | O | ✻—N(CH₃)(CH₃) | — | — |
| X256 | m1 = 0 | ✻—OX12 | ✻—C(C₂H₅)(C₂H₅)(C₂H₅) | O | ✻—OH | — | — |
| X257 | m1 = 0 | ✻—OX12 | ✻—C(C₂H₅)(C₂H₅)(C₂H₅) | O | ✻—OC₂H₅ | — | — |
| X258 | m1 = 0 | ✻—OX12 | ✻—C(C₂H₅)(C₂H₅)(C₂H₅) | O | ✻—N(C₂H₅)(H) | — | — |
| X259 | m1 = 0 | ✻—OX12 | ✻—C(C₂H₅)(C₂H₅)(C₂H₅) | O | ✻—N(CH₃)(CH₃) | — | — |
| X260 | m1 = 0 | ✻—OX12 | ✻—C(CH₃)(CH₂—)(CH₃) | O | ✻—OH | — | — |
| X261 | m1 = 0 | ✻—OX12 | ✻—C(CH₃)(CH=CH—✻)(CH₃) | O | ✻—OC₂H₅ | — | — |

-continued

| | | Substituent (X11) | | | | | |
|---|---|---|---|---|---|---|---|
| No. | $(A1)_{m1}$ ※—A1$_{m1}$—C(=O)—Z1 | Z1 | $(A2)_{m2}$ ※—A2$_{m2}$—Y=Z2 X12 | Y | Z2 | $(A3)_{m3}$ ※—A3$_{m3}$—C(=O)—Z3 X13 | Z3 |
| X262 | m1 = 0 | ※—NHX12 | ※—CH(CH$_2$OH)— | O | ※—OCH$_3$ | — | — |
| X263 | m1 = 0 | ※—NHX12 | ※—C(=CH$_2$)— | O | ※—OCH$_3$ | — | — |
| X264 | m1 = 0 | ※—NHX12 | ※—CH(CH$_2$OH)— | O | ※—OCH$_2$C$_6$H$_5$ | — | — |
| X265 | m1 = 0 | ※—OX12 | ※—C(CH$_3$)$_2$— | O | ※—OCH$_2$C$_2$F$_5$ | — | — |
| X266 | m1 = 0 | ※—OX12 | ※—C(CH$_3$)$_2$— | O | ※—OCH(CF$_3$)$_2$ | — | — |
| X267 | m1 = 0 | ※—OX12 | ※—C(CH$_3$)$_2$— | O | ※—OCH$_2$CF$_3$ | — | — |
| X268 | m1 = 0 | ※—OX12 | ※—C(CH$_3$)$_2$— | O | ※—NHCH$_2$CF$_3$ | — | — |
| X302 | m1 = 0 | ※—OX12 | ※—C(CH$_3$)$_2$— | | ※—N(X13)(H) | ※—CH$_2$— | ※—OC$_2$H$_5$ |

-continued
| No. | Substituent (X11) | | | | | | | |
|---|---|---|---|---|---|---|---|---|
| | (A1)$_{m1}$ | Z1 | (A2)$_{m2}$ | Y | Z2 | (A3)$_{m3}$ | Z3 | |
| | ※—A1$_{m1}$—C(=O)—Z1 | | X12[※—A2$_{m2}$—Y—Z2] | | | X13[※—A3$_{m3}$—C(=O)—Z3] | | |
| X303 | 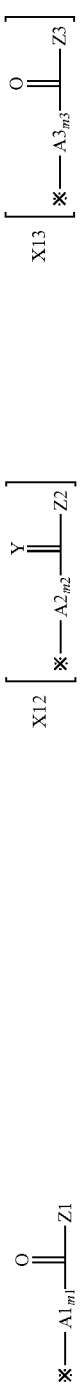 |  | — | — | — | — | — | |
| X304 |  |  | — | — | — | — | — | |
| X305 | m = 0 | ※—OX12 |  | O |  | — | — | |
| X306 | m = 0 |  | — | — | — | — | — | |
| X307 | m = 0 | ※—OX12 |  | O |  | — | — | |
| X308 | m = 0 |  | — | — | — | — | — | |

-continued

| No. | Substituent (X11) | | | | | | | |
|---|---|---|---|---|---|---|---|---|
| | $(A1)_{m1}$ | Z1 | $X12\left[\text{*}-A2_{m2}\right]\overset{Y}{\underset{}{\left.\right]}}-Z2$ | | | $X13\left[\text{*}-A3_{m3}\right]\overset{O}{\underset{}{\left.\right]}}-Z3$ | | |
| | | | $(A2)_{m2}$ | Y | Z2 | $(A3)_{m3}$ | Z3 | |
| X309 | m = 0 | cyclohexyl-N(*)-C(=O)-NH-cyclohexyl | — | — | — | — | — | |
| X310 | m = 0 | *—OX12 | (CH₃)₂C(*)— | O | *—NH—NH—C(=O)—CH₃ | — | — | |
| X311 | m = 0 | 5-methyl-1,3,4-oxadiazol-2-yl-C(CH₃)₂-O-* | — | — | — | — | — | |
| X312 | m = 0 | CF₃CH₂-N(CH₃)-C(=O)-C(CH₃)₂-O-* | — | — | — | — | — | |
| X313 | m = 0 | 5,5-dimethyl-4,5-dihydroisoxazol-3-yl-C(CH₃)₂-O-* | — | — | — | — | — | |

| No. | Substituent (X11) | | | | | | | | |
|---|---|---|---|---|---|---|---|---|---|
| | $(A1)_{m1}$ | Z1 | $(A2)_{m2}$ | Y | Z2 | $(A3)_{m3}$ | Z3 | | |
| X314 | m = 0 | [isoxazole-C(CH₃)₂-O-*, 5-methylisoxazol-3-yl] | — | — | — | — | — | | |
| X315 | m = 0 | [4,4-dimethyl-4,5-dihydroisoxazol-3-yl-CH(CH₃)-O-*] | — | — | — | — | — | | |
| X316 | m = 0 | [H₂N-NH-C(=O)-C(CH₃)₂-O-*] | — | — | — | — | — | | |
| X317 | m = 0 | [oxazol-4-yl-C(CH₃)₂-O-*] | — | — | — | — | — | | |
| X318 | m = 0 | [Cl-CH₂CH₂-O-*] | — | — | — | — | — | | |
| X319 | m = 0 | [3-methylisoxazol-5-yl-C(CH₃)₂-O-*] | — | — | — | — | — | | |

-continued
| No. | (A1)$_{m1}$ | Substituent (X11) X12 [ ※—A2$_{m2}$ ]—Y—Z2 | | | X13 [ ※—A3$_{m3}$ ]—Z3 | |
|---|---|---|---|---|---|---|
| | | Z1 | (A2)$_{m2}$ | Y | Z2 | (A3)$_{m3}$ | Z3 |
| No. | (A1)$_{m1}$ | Z1 | (A2)$_{m2}$ | Y | Z2 | (A3)$_{m3}$ | Z3 |
|---|---|---|---|---|---|---|---|
| X320 | m = 0 |  |  | O |  | — | — |
| X321 | m = 0 |  | — | — | — | — | — |
| X322 | m = 0 |  | — | — | — | — | — |
| X323 | m = 0 |  | — | — | — | — | — |
| X324 | m = 0 |  | — | — | — | — | — |

TABLE 3
| No. | G | Q | X1 | X2 | X3 | X4 | X5 | Physical constant |
|---|---|---|---|---|---|---|---|---|
| 1 | 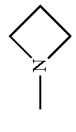 | —CN | —F | —H | —Cl | X208 | —H | 20.5° C. 1.5346 |
| 2 | 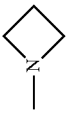 | —CN | —F | —H | —Cl | X210 | —H | 20.3° C. 1.5468 |
| 3 | 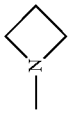 | —CN | —F | —H | —Cl | T003 | —H | 99-100 |
| 4 | 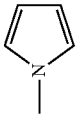 | —CN | —F | —H | —Cl | T003 | —H | 132-133 |
| 5 |  | —CN | —F | —H | —CN | T003 | —H | 101-103 |
| 6 |  | —CN | —H | —H | —CN | X112 | —H | 22.4° C. 1.5928 |
| 7 |  | —CN | —H | —H | —Cl | X226 | —H | 22.1° C. 1.5525 |
| 8 |  | —CN | —H | —H | —Cl | X123 | —H | 22.5° C. 1.577 |
| 9 |  | —CN | —H | —H | —Cl | X210 | —H | 22.5° C. 1.5506 |
| 10 | 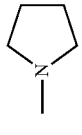 | —CN | —H | —H | —Cl | X102 | —H | 20.6° C. 1.6026 |

TABLE 3-continued
| No. | G | Q | X1 | X2 | X3 | X4 | X5 | Physical constant |
|---|---|---|---|---|---|---|---|---|
| 11 |  | —CN | —F | —H | —CN | X208 | —H | 126-128 |
| 12 |  | —CN | —F | —H | —CN | X226 | —H | AMORPHOUS |
| 13 |  | —CN | —F | —H | —Cl | N001 | —H | 118-120 |
| 14 |  | —CN | —F | —H | —CN | T003 | —H | 113-115 |
| 15 |  | —CN | —F | —H | —OCHF$_2$ | —H | —H | 22.4° C. 1.5376 |
| 16 |  | —CN | —F | —H | —OCHF$_2$ | X226 | —H | 22.1° C. 1.5329 |
| 17 |  | —CN | —F | —H | —OCHF$_2$ | X208 | —H | 22.3° C. 1.5055 |
| 18 |  | —CN | —F | —H | T008 | —H | —H | 108-110 |
| 19 |  | —CN | —F | —H | T009 | —H | —H | 81-83 |
| 20 |  | —CN | —F | —H | —Cl | —H | —H | 20.6° C. 1.5959 |
| 21 |  | —CN | —F | —H | —Cl | —CH2OH | —H | 23° C. 1.5786 |

TABLE 3-continued
| No. | G | Q | X1 | X2 | X3 | X4 | X5 | Physical constant |
|---|---|---|---|---|---|---|---|---|
| 22 | 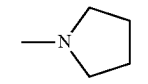 | —CN | —F | —H | —Cl | X101 | —H | 166-169 |
| 23 | 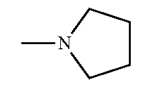 | —CN | —F | —H | —Cl | X103 | —H | 22.8° C. 1.5426 |
| 24 |  | —CN | —F | —H | —Cl | X104 | —H | 20.8° C. 1.571 |
| 25 |  | —CN | —F | —H | —Cl | X105 | —H | 22.5° C. 1.5631 |
| 26 | 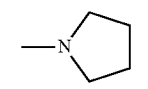 | —CN | —F | —H | —Cl | X106 | —H | 23.1° C. 1.565 |
| 27 | 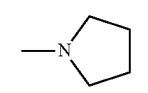 | —CN | —F | —H | —Cl | X107 | —H | 24.9° C. 1.5692 |
| 28 | 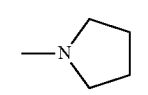 | —CN | —F | —H | —Cl | X108 | —H | 22.2° C. 1.5353 |
| 29 |  | —CN | —F | —H | —Cl | X109 | —H | 22.9° C. 1.5233 |
| 30 |  | —CN | —F | —H | —Cl | X110 | —H | 25.1° C. 1.5678 |
| 31 |  | —CN | —F | —H | —Cl | X111 | —H | 23.3° C. 1.5686 |
| 32 | 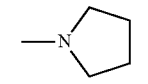 | —CN | —F | —H | —Cl | X112 | —H | 87-89 |

TABLE 3-continued
| No. | G | Q | X1 | X2 | X3 | X4 | X5 | Physical constant |
|---|---|---|---|---|---|---|---|---|
| 33 | 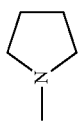 | —CN | —F | —H | —Cl | X113 | —H | 109-110 |
| 34 | 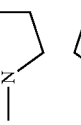 | —CN | —F | —H | —Cl | X114 | —H | 24.3° C. 1.5369 |
| 35 |  | —CN | —F | —H | —Cl | X115 | —H | 142-145 |
| 36 | 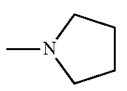 | —CN | —F | —H | —Cl | X116 | —H | 132-135 |
| 37 | 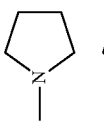 | —CN | —F | —H | —Cl | X117 | —H | 150-152 |
| 38 | 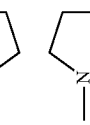 | —CN | —F | —H | —Cl | X118 | —H | 147-150 |
| 39 | 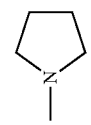 | —CN | —F | —H | —Cl | X119 | —H | 168-170 |
| 40 | 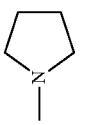 | —CN | —F | —H | —Cl | X120 | —H | AMORPHOUS |
| 41 | 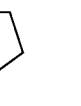 | —CN | —F | —H | —Cl | X121 | —H | 173-174 |
| 42 |  | —CN | —F | —H | —Cl | X122 | —H | 22.2° C. 1.5402 |
| 43 |  | —CN | —F | —H | —Cl | X123 | —H | 103-105 |

TABLE 3-continued

| No. | G | Q | X1 | X2 | X3 | X4 | X5 | Physical constant |
|---|---|---|---|---|---|---|---|---|
| 44 | N-pyrrolidinyl | —CN | —F | —H | —Cl | X124 | —H | 23.1° C. 1.5426 |
| 45 | N-pyrrolidinyl | —CN | —F | —H | —Cl | X125 | —H | 108-112 |
| 46 | N-pyrrolidinyl | —CN | —F | —H | —Cl | X127 | —H | AMORPHOUS |
| 47 | N-pyrrolidinyl | —CN | —F | —H | —Cl | X128 | —H | 22° C. 1.5528 |
| 48 | N-pyrrolidinyl | —CN | —F | —H | —Cl | X129 | —H | 164-166 |
| 49 | N-pyrrolidinyl | —CN | —F | —H | —Cl | X130 | —H | 22.4° C. 1.5641 |
| 50 | N-pyrrolidinyl | —CN | —F | —H | —Cl | X130 | —Cl | 22.6° C. 1.5542 |
| 51 | N-pyrrolidinyl | —CN | —F | —H | —Cl | X131 | —H | 90-92 |
| 52 | N-pyrrolidinyl | —CN | —F | —H | —Cl | X132 | —H | 99-100 |
| 53 | N-pyrrolidinyl | —CN | —F | —H | —Cl | X133 | —H | 22.3° C. 1.5599 |

TABLE 3-continued
| No. | G | Q | X1 | X2 | X3 | X4 | X5 | Physical constant |
|---|---|---|---|---|---|---|---|---|
| 54 | 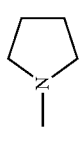 | —CN | —F | —H | —Cl | X134 | —H | 101-103 |
| 55 | 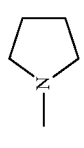 | —CN | —F | —H | —Cl | X135 | —H | 22.9° C. 1.5492 |
| 56 | 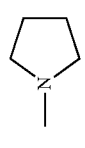 | —CN | —F | —H | —Cl | X136 | —H | 22.4° C. 1.5318 |
| 57 | 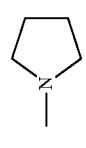 | —CN | —F | —H | —Cl | X137 | —H | AMORPHOUS |
| 58 | 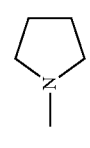 | —CN | —F | —H | —Cl | X138 | —H | 22.5° C. 1.5478 |
| 59 | 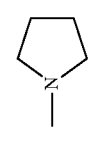 | —CN | —F | —H | —Cl | X139 | —H | 22.5° C. 1.5187 |
| 60 | 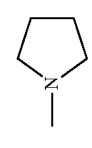 | —CN | —F | —H | —Cl | X140 | —H | 140-143 |
| 61 | 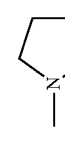 | —CN | —F | —H | —Cl | X141 | —H | 123-126 |
| 62 | 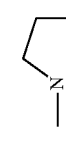 | —CN | —F | —H | —Cl | X142 | —H | 22.3° C. 1.5768 |
| 63 | 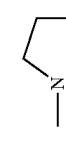 | —CN | —F | —H | —Cl | X143 | —H | 21.9° C. 1.576 |
| 64 | 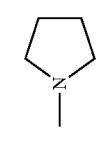 | —CN | —F | —H | —Cl | X144 | —H | 22° C. 1.5936 |

TABLE 3-continued
| No. | G | Q | X1 | X2 | X3 | X4 | X5 | Physical constant |
|---|---|---|---|---|---|---|---|---|
| 65 | 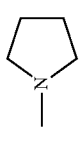 | —CN | —F | —H | —Cl | X145 | —H | 22.8° C. 1.586 |
| 66 |  | —CN | —F | —H | —Cl | X146 | —H | 22.6° C. 1.5772 |
| 67 | 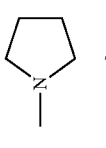 | —CN | —F | —H | —Cl | X201 | —H | 22.5° C. 1.5598 |
| 68 | 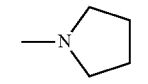 | —CN | —F | —H | —Cl | X202 | —H | 22° C. 1.5388 |
| 69 | 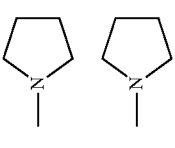 | —CN | —F | —H | —Cl | X203 | —H | 154-159 |
| 70 | 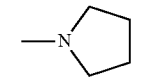 | —CN | —F | —H | —Cl | X204 | —H | 23.2° C. 1.5358 |
| 71 | 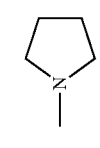 | —CN | —F | —H | —Cl | X205 | —H | VISCOUS OIL |
| 72 | 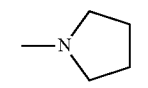 | —CN | —F | —H | —Cl | X206 | —H | AMORPHOUS |
| 73 | 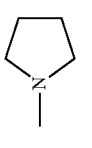 | —CN | —F | —H | —Cl | X207 | —H | 92-94 |
| 74 | 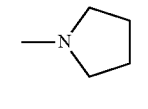 | —CN | —F | —H | —Cl | X208 | —H | 46-48 |
| 75 |  | —CN | —F | —H | —Cl | X209 | —H | 20.4° C. 1.53 |

TABLE 3-continued

| No. | G | Q | X1 | X2 | X3 | X4 | X5 | Physical constant |
|---|---|---|---|---|---|---|---|---|
| 76 | pyrrolidinyl | —CN | —F | —H | —Cl | X210 | —H | 22.2° C. 1.5414 |
| 77 | pyrrolidinyl | —CN | —F | —H | —Cl | X211 | —H | 104-106 |
| 78 | pyrrolidinyl | —CN | —F | —H | —Cl | X212 | —H | VISCOUS OIL |
| 79 | pyrrolidinyl | —CN | —F | —H | —Cl | X213 | —H | 22.8° C. 1.5467 |
| 80 | pyrrolidinyl | —CN | —F | —H | —Cl | X214 | —H | VISCOUS OIL |
| 81 | pyrrolidinyl | —CN | —F | —H | —Cl | X215 | —H | 24.9° C. 1.5454 |
| 82 | pyrrolidinyl | —CN | —F | —H | —Cl | X216 | —H | 22.5° C. 1.5379 |
| 83 | pyrrolidinyl | —CN | —F | —H | —Cl | X217 | —H | 117-119 |
| 84 | pyrrolidinyl | —CN | —F | —H | —Cl | X218 | —H | 25.5° C. 1.5389 |
| 85 | pyrrolidinyl | —CN | —F | —H | —Cl | X219 | —H | 23.3° C. 1.5526 |
| 86 | pyrrolidinyl | —CN | —F | —H | —Cl | X220 | —H | VISCOUS OIL |

TABLE 3-continued
| No. | G | Q | X1 | X2 | X3 | X4 | X5 | Physical constant |
|---|---|---|---|---|---|---|---|---|
| 87 | 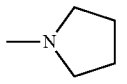 | —CN | —F | —H | —Cl | X221 | —H | 22.4° C. 1.5349 |
| 88 | 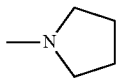 | —CN | —F | —H | —Cl | X222 | —H | AMORPHOUS |
| 89 | 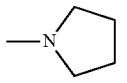 | —CN | —F | —H | —Cl | X223 | —H | AMORPHOUS |
| 90 | 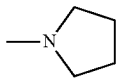 | —CN | —F | —H | —Cl | X224 | —H | VISCOUS OIL |
| 91 | 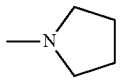 | —CN | —F | —H | —Cl | X225 | —H | 133-136 |
| 92 | 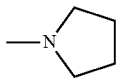 | —CN | —F | —H | —Cl | X226 | —H | VISCOUS OIL |
| 93 | 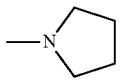 | —CN | —F | —H | —Cl | X227 | —H | 23.7° C. 1.5342 |
| 94 | 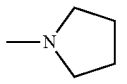 | —CN | —F | —H | —Cl | X228 | —H | 22.1° C. 1.5396 |
| 95 | 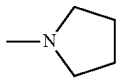 | —CN | —F | —H | —Cl | X229 | —H | 22.5° C. 1.555 |
| 96 | 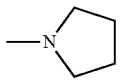 | —CN | —F | —H | —Cl | X230 | —H | 22.3° C. 1.5423 |
| 97 | 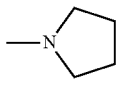 | —CN | —F | —H |  | X231 | —H | VISCOUS OIL |

TABLE 3-continued

| No. | G | Q | X1 | X2 | X3 | X4 | X5 | Physical constant |
|---|---|---|---|---|---|---|---|---|
| 98 | ⟨N-pyrrolidine⟩ | —CN | —F | —H | —Cl | X232 | —H | 126-128 |
| 99 | ⟨N-pyrrolidine⟩ | —CN | —F | —H | —Cl | X233 | —H | 187-190 |
| 100 | ⟨N-pyrrolidine⟩ | —CN | —F | —H | —Cl | X234 | —H | 22.8° C. 1.5649 |
| 101 | ⟨N-pyrrolidine⟩ | —CN | —F | —H | —Cl | X235 | —H | 118-119 |
| 102 | ⟨N-pyrrolidine⟩ | —CN | —F | —H | —Cl | X236 | —H | 22.2° C. 1.5543 |
| 103 | ⟨N-pyrrolidine⟩ | —CN | —F | —H | —Cl | X237 | —H | 22.5° C. 1.5618 |
| 104 | ⟨N-pyrrolidine⟩ | —CN | —F | —H | —Cl | X238 | —H | 158-161 |
| 105 | ⟨N-pyrrolidine⟩ | —CN | —F | —H | —Cl | X239 | —H | 111-112 |
| 106 | ⟨N-pyrrolidine⟩ | —CN | —F | —H | —Cl | X240 | —H | 22.9° C. 1.5615 |
| 107 | ⟨N-pyrrolidine⟩ | —CN | —F | —H | —Cl | X241 | —H | 23.3° C. 1.5491 |
| 108 | ⟨N-pyrrolidine⟩ | —CN | —F | —H | —Cl | X242 | —H | 57-59 |

TABLE 3-continued
| No. | G | Q | X1 | X2 | X3 | X4 | X5 | Physical constant |
|---|---|---|---|---|---|---|---|---|
| 109 | 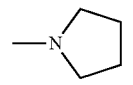 | —CN | —F | —H | —Cl | X243 | —H | AMORPHOUS |
| 110 |  | —CN | —F | —H | —Cl | X244 | —H | AMORPHOUS |
| 111 | 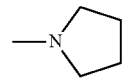 | —CN | —F | —H | —Cl | X245 | —H | 22.4° C. 1.5555 |
| 112 | 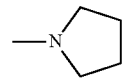 | —CN | —F | —H | —Cl | X246 | —H | 163-167 |
| 113 | 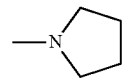 | —CN | —F | —H | —Cl | X247 | —H | 25.1° C. 1.5818 |
| 114 | 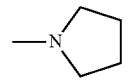 | —CN | —F | —H | —Cl | X248 | —H | 21.9° C. 1.5211 |
| 115 | 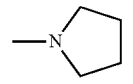 | —CN | —F | —H | —Cl | X249 | —H | AMORPHOUS |
| 116 | 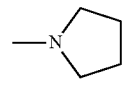 | —CN | —F | —H | —Cl | X250 | —H | VISCOUS OIL |
| 117 | 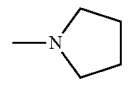 | —CN | —F | —H | —Cl | X251 | —H | AMORPHOUS |
| 118 | 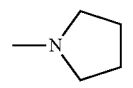 | —CN | —F | —H | —Cl | X252 | —H | AMORPHOUS |

TABLE 3-continued
| No. | G | Q | X1 | X2 | X3 | X4 | X5 | Physical constant |
|---|---|---|---|---|---|---|---|---|
| 119 | 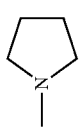 | —CN | —F | —H | —Cl | X253 | —H | 23.6° C. 1.5483 |
| 120 | 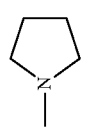 | —CN | —F | —H | —Cl | X254 | —H | 24.4° C. 1.5548 |
| 121 | 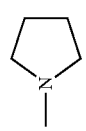 | —CN | —F | —H | —Cl | X255 | —H | 24.3° C. 1.5535 |
| 122 | 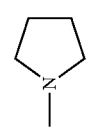 | —CN | —F | —H | —Cl | X256 | —H | AMORPHOUS |
| 123 | 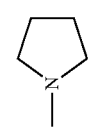 | —CN | —F | —H | —Cl | X257 | —H | 22.8° C. 1.5352 |
| 124 | 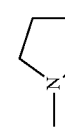 | —CN | —F | —H | —Cl | X258 | —H | 22.2° C. 1.545 |
| 125 | 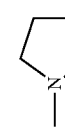 | —CN | —F | —H | —Cl | X259 | —H | 25.1° C. 1.5606 |
| 126 | 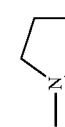 | —CN | —F | —H | —Cl | X260 | —H | 24.8° C. 1.539 |
| 127 | 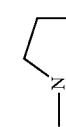 | —CN | —F | —H | —Cl | X261 | —H | 24.5° C. 1.5428 |
| 128 | 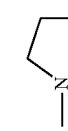 | —CN | —F | —H | —Cl | X301 | —H | 23.8° C. 1.5161 |
| 129 | 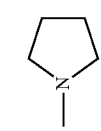 | —CN | —F | —H | —Cl | X302 | —H | 24.6° C. 1.5261 |

TABLE 3-continued
| No. | G | Q | X1 | X2 | X3 | X4 | X5 | Physical constant |
|---|---|---|---|---|---|---|---|---|
| 130 | 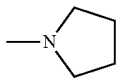 | —CN | —F | —H | —Cl | —F | —H | 22.7° C. 1.5733 |
| 131 | 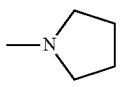 | —CN | —F | —H | —Cl | —NH2 | —H | 83-85 |
| 132 |  | —CN | —F | —H | —Cl | —NO2 | —H | 20.3° C. 1.5982 |
| 133 | 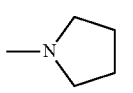 | —CN | —F | —H | —Cl | N002 | —H | 116-118 |
| 134 | 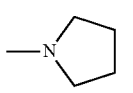 | —CN | —F | —H | —Cl | N003 | —H | 135-137 |
| 135 | 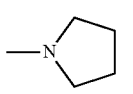 | —CN | —F | —H | —Cl | N004 | —H | 134-137 |
| 136 | 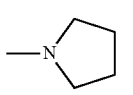 | —CN | —F | —H | —Cl | N006 | —H | 22.4° C. 1.5425 |
| 137 | 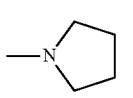 | —CN | —F | —H | —Cl | —OH | —H | 165-167 |
| 138 |  | —CN | —F | —H | —Cl | T045 | —H | 22.3° C. 1.5956 |
| 139 |  | —CN | —F | —H | —Cl | T001 | —H | 65-67 |
| 140 | 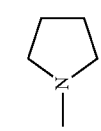 | —CN | —F | —H | —Cl | T002 | —H | 22.4° C. 1.5776 |

TABLE 3-continued
| No. | G | Q | X1 | X2 | X3 | X4 | X5 | Physical constant |
|---|---|---|---|---|---|---|---|---|
| 141 |  | —CN | —F | —H | —Cl | T003 | —H | 88-89 |
| 142 |  | —CN | —F | —H | —Cl | T003 | —CH$_2$CH=CH$_2$ | 63-64 |
| 143 |  | —CN | —F | —H | —Cl | T003 | —Cl | 22.6° C. 1.5861 |
| 144 |  | —CN | —F | —H | —Cl | T003 | —NO2 | VISCOUS OIL |
| 145 |  | —CN | —F | —H | —Cl | T005 | —H | 71-75 |
| 146 |  | —CN | —F | —H | —Cl | T006 | —H | 22.8° C. 1.5719 |
| 147 |  | —CN | —F | —H | —Cl | T007 | —H | 22.2° C. 1.56 |
| 148 |  | —CN | —F | —H | —Cl | T008 | —H | 75-78 |
| 149 |  | —CN | —F | —H | —Cl | T011 | —H | 110-113 |
| 150 |  | —CN | —F | —H | —Cl | T012 | —H | 55-58 |
| 151 |  | —CN | —F | —H | —Cl | T013 | —H | 22.4° C. 1.5745 |

TABLE 3-continued
| No. | G | Q | X1 | X2 | X3 | X4 | X5 | Physical constant |
|---|---|---|---|---|---|---|---|---|
| 152 | 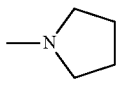 | —CN | —F | —H | —Cl | T014 | —H | 22.2° C. 1.6089 |
| 153 |  | —CN | —F | —H | —Cl | T015 | —H | 110-113 |
| 154 | 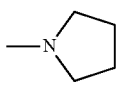 | —CN | —F | —H | —Cl | T016 | —H | 156-158 |
| 155 |  | —CN | —F | —H | —Cl | T017 | —H | 151-153 |
| 156 | 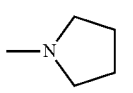 | —CN | —F | —H | —Cl | S001 | —H | 61-64 |
| 157 |  | —CN | —F | —H | —Cl | S002 | —H | 22.4° C. 1.62 |
| 158 | 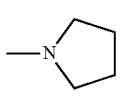 | —CN | —F | —H | —Cl | S003 | —H | 22.5° C. 1.6018 |
| 159 |  | —CN | —F | —H | —Cl | S004 | —H | 22.6° C. 1.5868 |
| 160 | 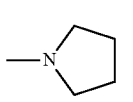 | —CN | —F | —H | —Cl | S005 | —H | 86-90 |
| 161 |  | —CN | —F | —H | —Cl | S006 | —H | 151-153 |
| 162 | 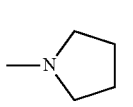 | —CN | —F | —H | —Cl | S007 | —H | 113-114 |

TABLE 3-continued

| No. | G | Q | X1 | X2 | X3 | X4 | X5 | Physical constant |
|---|---|---|---|---|---|---|---|---|
| 163 | pyrrolidin-1-yl | —CN | —F | —H | —Cl | T010 | —H | 103-105 |
| 164 | pyrrolidin-1-yl | —CN | —F | —H | —Cl | H002 | —H | 128-131 |
| 165 | pyrrolidin-1-yl | —CN | —F | —H | —Cl | —O—C(CH₃)(CH₃)—N═ | | 145-147 |
| 166 | pyrrolidin-1-yl | —CN | —F | —H | —Cl | —O—C(C₂H₅)—N═ | | 99-100 |
| 167 | pyrrolidin-1-yl | —CN | —F | —H | —Cl | —N═C(CH₃)—S— | | 145-147 |
| 168 | pyrrolidin-1-yl | —CN | —F | —H | —Cl | —O—C(CH₃)(CH₂CH₃) | | VISCOUS OIL |
| 169 | pyrrolidin-1-yl | —CN | —F | —H | —Br | X208 | —H | 20.2° C. 1.5553 |
| 170 | pyrrolidin-1-yl | —CN | —F | —H | —Br | T003 | —H | 83-85 |
| 171 | pyrrolidin-1-yl | —CN | —F | | | —O—CH₂—C(═O)—N(CH₂—C≡CH) | —H | 153-157 |

TABLE 3-continued
| No. | G | Q | X1 | X2 | X3 | X4 | X5 | Physical constant |
|---|---|---|---|---|---|---|---|---|
| 172 | 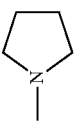 | —CN | —F | —H | | NC—C≡C—CH₂—O—CH₂—C(=O)—N— | —H | 231-234 |
| 173 | 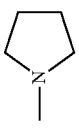 | —CN | —F | —H | | O=C(—CH₂—C≡CH)—S—N— | —H | 142-144 |
| 174 | 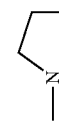 | —CN | —F | —H | —Cl | | | 130-132 |
| 175 | 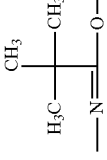 | —CN | —CH3 | —H | —CH3 | (CH₃)(CH₃)(H₃C)C—O—N= | —CH3 | 78-83 |
| 176 | 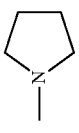 | —CN | —CH3 | —H | —Br | | —H | 58-60 |
| 177 | 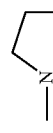 | —CN | —CH3 | —H | —Br | —H | —CH3 | 118-120 |
| 178 | 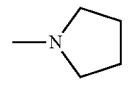 | —CN | —Cl | —H | —Cl | —H | —H | 20.7° C. 1.6158 |
| 179 |  | —CN | —Cl | —H | —Cl | X101 | —H | 163-165 |
| 180 | 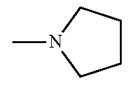 | —CN | —Cl | —H | —Cl | X112 | —H | 104-106 |
| 181 | 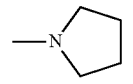 | —CN | —Cl | —H | —Cl | X126 | —H | 156-158 |

TABLE 3-continued

| No. | G | Q | X1 | X2 | X3 | X4 | X5 | Physical constant |
|---|---|---|---|---|---|---|---|---|
| 182 | pyrrolidinyl | —CN | —Cl | —H | —Cl | X136 | —H | 84-86 |
| 183 | pyrrolidinyl | —CN | —Cl | —H | —Cl | X208 | —H | 22° C. 1.551 |
| 184 | pyrrolidinyl | —CN | —Cl | —H | —Cl | T003 | —H | VISCOUS OIL |
| 185 | pyrrolidinyl | —CN | —Cl | —H | —Cl | T010 | —H | 79-81 |
| 186 | pyrrolidinyl | —CN | —Cl | —H | —Cl | —NO2 | —H | 101-104 |
| 187 | pyrrolidinyl | —CN | —Cl | —H | —Cl | N005 | —H | AMORPHOUS |
| 188 | pyrrolidinyl | —CN | H001 | —H | —Cl | S006 | —H | AMORPHOUS |
| 189 | pyrrolidinyl | —CH=NOH | —F | —H | —Cl | —OC3H7 | —H | 150-154 |
| 190 | pyrrolidinyl | —CH=NOCH₃ | —F | —H | —Cl | T003 | —H | 73-75 |
| 191 | pyrrolidinyl | —CH=NOC₂H₅ | —F | —H | —Cl | T003 | —H | 22.4° C. 1.5796 |
| 192 | pyrrolidinyl | —CH=NOCH₂Ph | —F | —H | —Cl | —OH | —H | AMORPHOUS |

TABLE 3-continued

| No. | G | Q | X1 | X2 | X3 | X4 | X5 | Physical constant |
|---|---|---|---|---|---|---|---|---|
| 193 |  | —CH=NOCH₂Ph | —F | —H | —Cl | —OC₃H₇ | —H | 20.6° C. 1.5922 |
| 194 |  | —CH=NOCH₂Ph | —F | —H | —Cl | T003 | —H | 58-62 |
| 195 |  | —CH=NOCH₂Ph | —F | —H | —Cl | T004 | —H | 20.2° C. 1.609 |
| 196 |  | —CH=NOCH₂CH=CH₂ | —F | —H | —Cl | T003 | —H | 22.6° C. 1.5852 |
| 197 |  | —CH=NOCH₂CH=CHCl | —F | —H | —Cl | T003 | —H | 20.6° C. 1.5862 |
| 198 |  | $\underset{O}{\overset{NH_2}{\|}}$ | —F | —H | —Cl | T003 | —H | 186-188 |
| 199 |  | $\underset{O}{\overset{N(CH_3)_2}{\|}}$ | —F | —H | —Cl | T003 | —H | AMORPHOUS |
| 200 |  | $\underset{S}{\overset{NH_2}{\|}}$ | —F | —H | —Cl | X208 | —H | 147-150 |
| 201 |  | $\underset{S}{\overset{NHCOCH_3}{\|}}$ | —F | —H | —Cl | X208 | —H | AMORPHOUS |
| 202 |  | $\underset{S}{\overset{N(CH_3)_2}{\|}}$ | —F | —H | —Cl | X208 | —H | 20.5° C. 1.558 |

TABLE 3-continued

| No. | G | Q | X1 | X2 | X3 | X4 | X5 | Physical constant |
|---|---|---|---|---|---|---|---|---|
| 203 | pyrrolidin-1-yl | —C(=S)N(CH₃)CH₃ | —F | —H | —Cl | T003 | —H | 20.5° C. 1.584 |
| 204 | pyrrolidin-1-yl | —C(=S)N(CH₃)(CH₂Ph) | —F | —H | —Cl | X208 | —H | AMORPHOUS |
| 205 | pyrrolidin-1-yl | —C(=S)-pyrrolidin-1-yl | —F | —H | —Cl | T003 | —H | AMORPHOUS |
| 206 | pyrrolidin-1-yl | —C(=S)-morpholin-4-yl | —F | —H | —Cl | T003 | —H | 143-146 |
| 207 | pyrrolidin-1-yl | 3-methyl-4,5-dihydroisoxazol-5-yl | —F | —H | —Cl | T003 | —H | 79-81 |
| 208 | pyrrolidin-1-yl | 3,5-dimethylisoxazol-4-yl | —F | —H | —Cl | T003 | —H | AMORPHOUS |
| 209 | pyrrolidin-1-yl | thiazol-2-yl | —F | —H | —Cl | T003 | —H | AMORPHOUS |
| 210 | pyrrolidin-1-yl | pyridin-2-yl | —F | —H | —Cl | T003 | —H | AMORPHOUS |
| 211 | 2-methylpyrrolidin-1-yl | —CN | —F | —H | —Cl | T003 | —H | 20.5° C. 1.5805 |

TABLE 3-continued

| No. | G | Q | X1 | X2 | X3 | X4 | X5 | Physical constant |
|---|---|---|---|---|---|---|---|---|
| 212 | 2-methyl-1-methylpyrrolidinyl | —CN | —Cl | —H | —Cl | —H | —H | 22° C. 1.5825 |
| 213 | 3-fluoro-1-methylpyrrolidinyl | —CN | —F | —H | —Cl | T003 | —H | 20.5° C. 1.5636 |
| 214 | 3,3-difluoro-1-methylpyrrolidinyl | —CN | —F | —H | —Cl | T003 | —H | 80-83 |
| 215 | 3-(N,N-dimethylamino)-1-methylpyrrolidinyl | —CN | —Cl | —H | —Cl | —H | —H | 21.4° C. 1.5927 |
| 216 | 1-methyl-2-oxopyrrolidinyl | —CN | —F | —H | —Cl | T003 | —H | 129-132 |
| 217 | 3-chloro-1-methylpyrrolidinyl | —CN | —F | —H | —Cl | T003 | —H | 20.6° C. 1.5475 |
| 218 | 3-bromo-1-methylpyrrolidinyl | —CN | —F | —H | —Cl | T003 | —H | 20.6° C. 1.5739 |
| 219 | 1-methylpyrazolyl | —CN | —F | —H | —Cl | T003 | —H | 107-108 |

TABLE 3-continued
| No. | G | Q | X1 | X2 | X3 | X4 | X5 | Physical constant |
|-----|---|---|----|----|----|----|----|--------------------|
| 220 | 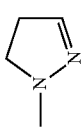 | —CN | —F | —H | —Cl | T003 | —H | 117-120 |
| 221 | 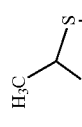 | —CN | —F | —H | —Cl | T003 | —H | 20.4° C. 1.5972 |
| 222 | 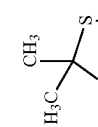 | —CN | —F | —H | —Cl | T003 | —H | 20.3° C. 1.5926 |
| 223 | 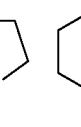 | —CN | —H | —H | —NO2 | —H | —H | 113-115 |
| 224 | 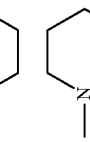 | —CN | —H | —H | —Cl | X102 | —H | 20.6° C. 1.5957 |
| 225 | 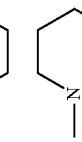 | —CN | —F | —H | —Cl | —H | —H | 20.5° C. 1.5882 |
| 226 | 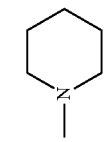 | —CN | —F | —H | —Cl | T003 | —H | 19.7° C. 1.5673 |
| 227 | 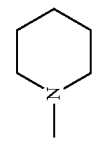 | —CN | —Cl | —H | —Cl | —H | —H | 20.6° C. 1.6045 |
| 228 | 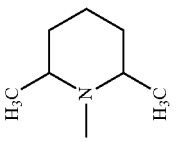 | —CN | —F | —H | —Cl | T003 | —H | 20° C. 1.5545 |

TABLE 3-continued

| No. | G | Q | X1 | X2 | X3 | X4 | X5 | Physical constant |
|---|---|---|---|---|---|---|---|---|
| 229 | 3,5-dimethylpiperidin-1-yl | —CN | —F | —H | —Cl | T003 | —H | 21.2° C. 1.5542 |
| 230 | 3,5-dimethylpiperidin-1-yl | —CN | —F | —H | —Cl | T003 | —H | 19.5° C. 1.556 |
| 231 | 4-phenylpiperazin-1-yl | —CN | —Cl | —H | —Cl | —H | —H | 149-151 |
| 232 | morpholin-4-yl | —CN | —H | —H | —CN | X112 | —H | 100-102 |
| 233 | morpholin-4-yl | —CN | —H | —H | —CN | X226 | —H | 23° C. 1.5497 |
| 234 | morpholin-4-yl | —CN | —H | —H | T045 | —H | —H | 68-70 |
| 235 | morpholin-4-yl | —CN | —H | —H | —OPh | —H | —H | 114-117 |
| 236 | morpholin-4-yl | —CN | —H | —Cl | —Cl | —H | —H | 110-112 |

TABLE 3-continued
| No. | G | Q | X1 | X2 | X3 | X4 | X5 | Physical constant |
|---|---|---|---|---|---|---|---|---|
| 237 |  | —CN | —F | —H | —Cl | X101 | —H | 190-193 |
| 238 |  | —CN | —F | —H | —Cl | X112 | —H | 68-71 |
| 239 |  | —CN | —F | —H | —Cl | X206 | —H | 22.7° C. 1.5421 |
| 240 |  | —CN | —F | —H | —Cl | X208 | —H | 22.4° C. 1.5385 |
| 241 |  | —CN | —F | —H | —Cl | X217 | —H | 22.9° C. 1.5449 |
| 242 |  | —CN | —F | —H | —Cl | X226 | —H | 23.3° C. 1.5585 |
| 243 |  | —CN | —Cl | —H | —Cl | T003 | —H | 114-117 |
| 244 |  | —CN | —F | —H | —Cl | —H | —H | 121-122 |
| 245 |  | —CH=NOCH₂CH=CHCl | —F | —H | —Cl | T003 | —H | 20.5° C. 1.5809 |
| 246 |  | (tetrazole) | —Cl | —H | —Cl | —H | —H | 235-236.5 |

TABLE 3-continued

| No. | G | Q | X1 | X2 | X3 | X4 | X5 | Physical constant |
|---|---|---|---|---|---|---|---|---|
| 247 | N-thiomorpholine | —CN | —Cl | —H | —Cl | —H | —H | 22.2° C. 1.637 |
| 248 | N-thiomorpholine dioxide | —CN | —Cl | —H | —Cl | —H | —H | 130-134 |
| 249 | N-azepane | —CN | —F | —H | —Cl | T003 | —H | 19.8° C. 1.5853 |
| 250 | 3,3-difluoropyrrolidine | —CN | —F | —H | —Cl | T003 | —H | 20.6° C. 1.5372 |
| 251 | 2-CF3-pyrrolidine | —CN | —F | —H | —Cl | T003 | —H | 20.6° C. 1.5311 |
| 252 | morpholine | —CN | —F | —H | —Cl | H003 | —H | AMORPHOUS |
| 253 | pyrrolidine | —CN | —F | —H | —Cl | —O—C(=O)—NH— | —H | 212-214 |
| 254 | pyrrolidine | —CN | —F | —H | —Cl | —O—C(=O)—N(CH3)— | —H | 194-195 |
| 255 | pyrrolidine | —CN | —F | —H | —Cl | —O—C(=O)—N(CH2C≡CH)— | —H | 147-149 |
| 256 | pyrrolidine | —CN | —F | —H | —Cl | —O—CH2—C(=O)—NH— | —H | 204-205 |

TABLE 3-continued

| No. | G | Q | X1 | X2 | X3 | X4 | X5 | Physical constant |
|---|---|---|---|---|---|---|---|---|
| 257 | 3,3,4,4-tetrafluoropyrrolidin-1-yl | —CN | T008 | —H | —Cl | X112 | —H | 112-113 |
| 258 | 3,3,4,4-tetrafluoropyrrolidin-1-yl | —CN | —F | —H | —Cl | X214 | —H | AMORPHOUS |
| 259 | 3,3,4,4-tetrafluoropyrrolidin-1-yl | —CN | —F | —H | —Cl | X211 | —H | 20.6° C. 1.4914 |
| 260 | morpholin-4-yl | —CN | —F | —H | —Cl | X148 | —H | 167-170 |
| 261 | pyrrolidin-1-yl | —CN | —F | —H | —Cl | —CH₂C(CH₃)₂OCH₃ | —H | 22° C. 1.564 |
| 262 | 6-azabicyclo[3.1.0] epoxide | —CN | —F | —H | —Cl | T003 | —H | 127-129 |
| 263 | 3,3,4,4-tetrafluoropyrrolidin-1-yl | —CN | —F | —H | —Cl | X130 | —H | 20.6° C. 1.5077 |
| 264 | morpholin-4-yl | —CN | —F | —H | —Cl | X214 | —H | VISCOUS OIL |

TABLE 3-continued

| No. | G | Q | X1 | X2 | X3 | X4 | X5 | Physical constant |
|-----|---|---|----|----|----|----|----|-------------------|
| 265 | 3,3,4,4-tetrafluoropyrrolidine | —CN | —F | —H | —Cl | X147 | —H | 123-126 |
| 266 | pyrrolidine | —CN | —F | —H | —Cl | X147 | —H | 91-92 |
| 267 | 3,4-difluoropyrrolidine | —CN | —F | —H | —Cl | T003 | —H | VISCOUS OIL |
| 268 | 3,4-difluoropyrrolidine | —CN | —F | —H | —Cl | T003 | —H | VISCOUS OIL |
| 269 | pyrrolidine | —CN | —F | —H | —Cl | —C(O)CH₃ | —H | 22° C. 1.5689 |
| 270 | pyrrolidine | —CN | —F | —H | —Cl | X201 | —H | 22° C. 1.52 |
| 271 | bicyclic azetidine | —CN | —F | —H | —Cl | T003 | —H | 20.6° C. 1.5958 |
| 272 | 3,3,4,4-tetrafluoropyrrolidine | —CN | —Cl | | | —H | | 79-81 |

TABLE 3-continued

| No. | G | Q | X1 | X2 | X3 | X4 | X5 | Physical constant |
|---|---|---|---|---|---|---|---|---|
| 273 | 3,3,4,4-tetrafluoropyrrolidinyl (N-methyl) | —CN | —F | —H | —Cl | T045 | —H | 142-144 |
| 274 | 3,3,4,4-tetrafluoropyrrolidinyl (N-methyl) | —CN | —F | —H | —O—CH₂—C(=O)—N(H)—C≡CH | | —H | 147-149 |
| 275 | 3,3,4,4-tetrafluoropyrrolidinyl (N-methyl) | —CN | —F | —H | —Cl | —H | —H | 20.6° C. 1.526 |
| 276 | 3,3,4,4-tetrafluoropyrrolidinyl (N-methyl) | —CN | —F | —H | —Cl | —NO2 | —H | 115-117 |
| 277 | 3,3,4,4-tetrafluoropyrrolidinyl (N-methyl) | —CN | —F | —H | —Cl | —NH2 | —H | 99-102 |
| 278 | 3,3,4,4-tetrafluoropyrrolidinyl (N-methyl) | —CN | —F | —H | —Cl | S008 | —H | 67-70 |
| 279 | pyrrolidinyl (N-methyl) | —CN | —F | —H | —Cl | S008 | —H | 20.4° C. 1.6283 |

TABLE 3-continued

| No. | G | Q | X1 | X2 | X3 | X4 | X5 | Physical constant |
|---|---|---|---|---|---|---|---|---|
| 280 | 3,3,4,4-tetrafluoropyrrolidin-1-yl | —CN | —F | —H | —Cl | —OH | —H | 92-95 |
| 281 | 3,3,4,4-tetrafluoropyrrolidin-1-yl | —CN | —F | —H | —Cl | T006 | —H | 20.5° C. 1.522 |
| 282 | 3,3,4,4-tetrafluoropyrrolidin-1-yl | —CN | —F | —H | —Cl | T008 | —H | 72-74 |
| 283 | 3,3,4,4-tetrafluoropyrrolidin-1-yl | —CN | —F | —H | —Cl | S009 | —H | 169-170 |
| 284 | pyrrolidin-1-yl | —CN | —F | —H | —Cl | X148 | —H | AMORPHOUS |
| 285 | pyrrolidin-1-yl | —CN | —F | —H | —Cl | H004 | —H | AMORPHOUS |
| 286 | 3,3,4,4-tetrafluoropyrrolidin-1-yl | —CN | —F | —H | —Cl | N003 | —H | 181-184 |

TABLE 3-continued
| No. | G | Q | X1 | X2 | X3 | X4 | X5 | Physical constant |
|---|---|---|---|---|---|---|---|---|
| 287 | 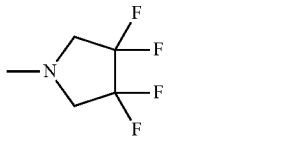 | —CN | —F | —H | —Cl | T018 | —H | 73-75 |
| 288 | 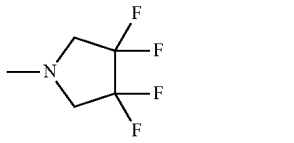 | —CN | —F | —H | —Cl | T019 | —H | 84-87 |
| 289 | 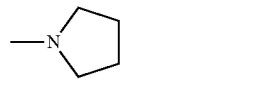 | —CN | —F | —H | —Cl | H005 | —H | 102-105 |
| 290 |  | —CN | —F | —H | —Cl | N007 | —H | 150-155 |
| 291 | 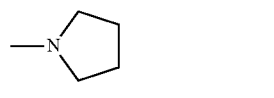 | —CN | —F | —H | —Cl | H006 | —H | 118-120 |
| 292 |  | —CN | —F | —H | —Cl | H007 | —H | AMORPHOUS |
| 293 |  | —C(O)NH$_2$ | —Cl | —H | —Cl | X136 | —H | 160-163 |
| 294 |  | —C(O)NH$_2$ | —Cl | —H | —Cl | T010 | —H | 173-175 |
| 295 |  | —CN | —F | —H | | T020 | —H | 50-53 |

TABLE 3-continued
| No. | G | Q | X1 | X2 | X3 | X4 | X5 | Physical constant |
|---|---|---|---|---|---|---|---|---|
| 296 | 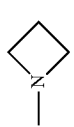 | —CN | —Cl | —H | —Cl | —H | —H | VISCOUS OIL |
| 297 |  | —CN | —F | —H | —Cl | T002 | —H | 92-95 |
| 298 |  | —CN | —F | —H | —Cl | T021 | —H | 88-90 |
| 299 | 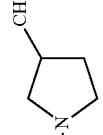 | —CN | —F | —H | —Cl | T003 | —H | 20.5° C. 1.5845 |
| 300 | 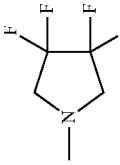 | —CN | —F | —H | —Cl | X125 | —H | 126-128 |
| 301 | 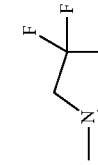 | —CN | —F | —H | —Cl | T022 | —H | 93-95 |
| 302 | 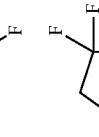 | —CN | —F | —H | —Cl | N001 | —H | VISCOUS OIL |
| 303 | 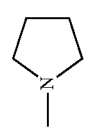 | —CN | —F | —H | —Cl | X262 | —H | AMORPHOUS |

TABLE 3-continued

| No. | G | Q | X1 | X2 | X3 | X4 | X5 | Physical constant |
|---|---|---|---|---|---|---|---|---|
| 304 | N-methylpyrrolidine | —CN | —F | —H | —Cl | X263 | —H | 118-120 |
| 305 | N-methylpyrrolidine | —CN | —F | —H | —Cl | H008 | —H | 20.6° C. 1.5799 |
| 306 | N-methylpyrrolidine | —CN | —F | —H | —Cl | X264 | —H | AMORPHOUS |
| 307 | N-methylpyrrolidine | —CN | —F | —H | —Cl | H009 | —H | 20.4° C. 1.5698 |
| 308 | tetrafluoro-N-methylpyrrolidine | —CN | —F | —H | —Cl | T023 | —H | 96-98 |
| 309 | tetrafluoro-N-methylpyrrolidine | —CN | —F | —H | —Cl | T001 | —H | 79-81 |
| 310 | tetrafluoro-N-methylpyrrolidine | —CN | —F | —H | —Cl | T024 | —H | 58-59 |
| 311 | N-methylpyrrolidine | —CN | —F | —H | —Cl | H010 | —H | AMORPHOUS |

TABLE 3-continued
| No. | G | Q | X1 | X2 | X3 | X4 | X5 | Physical constant |
|---|---|---|---|---|---|---|---|---|
| 312 |  | —CN | —F | —H | —Cl | T025 | —H | 20.5° C. 1.5155 |
| 313 |  | —CN | —F | —H | —Cl | T026 | —H | 62-64 |
| 314 |  | —CN | —F | —H | —Cl | H011 | —H | AMORPHOUS |
| 315 |  | —CN | —F | —H | —Cl | C003 | —H | 143-145 |
| 316 |  | —CN | —F | —H | —Cl | H012 | —H | 77-79 |
| 317 |  | —CN | —F | —H | —Cl | T027 | —H | 69-71 |
| 318 |  | —CN | —F | —H | —Cl | H018 | —H | AMORPHOUS |
| 319 |  | —CN | —F | —H | —Cl | H013 | —H | 196-201 |
| 320 |  | —CN | —F | —H | —Cl | T003 | —H | 20.6° C. 1.5705 |

TABLE 3-continued

| No. | G | Q | X1 | X2 | X3 | X4 | X5 | Physical constant |
|---|---|---|---|---|---|---|---|---|
| 321 | N-methylpyrrolidin-2-yl | —CN | —F | —H | —Cl | H014 | —H | VISCOUS OIL |
| 322 | N-methylpyrrolidin-2-yl | —CN | —F | —H | —Cl | H015 | —H | 20.6° C. 1.5884 |
| 323 | N-methylpyrrolidin-2-yl | —CN | —F | —H | —Cl | H016 | —H | 136-140 |
| 324 | N-methylpyrrolidin-2-yl | —CN | —F | —H | —Cl | H017 | —H | 20.7° C. 1.5786 |
| 325 | 1-methyl-2-phenylpyrazolidin-3-yl | —CN | —F | —H | —Cl | T003 | —H | AMORPHOUS |
| 326 | 1,3-dimethyl-2-oxopyrrolidin-3-yl | —CN | —F | —H | —Cl | T003 | —H | 109-112 |
| 327 | 1-methyl-2-phenyl-5-oxopyrazolidin-3-yl | —CN | —F | —H | —Cl | T003 | —H | VISCOUS OIL |
| 328 | 1-methyl-2-(trifluoromethyl)pyrrolidin-2-yl | —CN | —H | —CF₃ | —H | —CF₃ | —H | 20.7° C. 1.4608 |

TABLE 3-continued
| No. | G | Q | X1 | X2 | X3 | X4 | X5 | Physical constant |
|---|---|---|---|---|---|---|---|---|
| 329 | 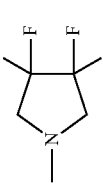 | —CN | —F | —H | —Cl | X112 | —H | 94-96 |
| 330 | 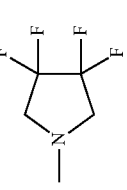 | —CN | —F | —H | —Cl | X101 | —H | 155-159 |
| 331 | 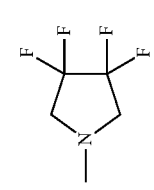 | —CN | —F | —H | —Cl | X149 | —H | 112-116 |
| 332 | 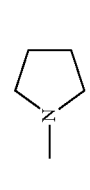 | —CN | —F | —H | —Cl | C002 | —H | 21.3° C. 1.5840 |
| 333 | 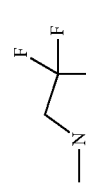 | —CN | —F | —H | —Cl | X103 | —H | 93-96 |
| 334 | 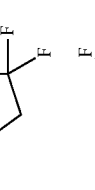 | —CN | —F | —H | —Cl | X151 | —H | AMORPHOUS |
| 335 | 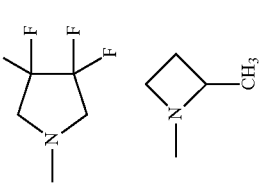 | —CN | —F | —H |  | T003 | —H | 21.0° C. 1.5793 |

TABLE 3-continued

| No. | G | Q | X1 | X2 | X3 | X4 | X5 | Physical constant |
|---|---|---|---|---|---|---|---|---|
| 336 | tetrafluoropyrrolidinyl | —CN | —F | —H | —Cl | H005 | —H | AMORPHOUS |
| 337 | tetrafluoropyrrolidinyl | —CN | —F | —H | —Cl | H007 | —H | AMORPHOUS |
| 338 | tetrafluoropyrrolidinyl | —CN | —F | —H | —S(=O)(=N—)—CH₂C≡CH | | —H | 127-129 |
| 339 | tetrafluoropyrrolidinyl | —CN | —F | —H | —Cl | T014 | —H | AMORPHOUS |
| 340 | tetrafluoropyrrolidinyl | —CN | —F | —H | —Cl | T028 | —H | 20.7° C. 1.5342 |
| 341 | tetrafluoropyrrolidinyl | —CN | —F | —H | —Cl | T029 | —H | 20.9° C. 1.5523 |
| 342 | tetrafluoropyrrolidinyl | —CN | —H | —H | —Cl | —OCH₃ | —H | 136-139 |

TABLE 3-continued
| No. | G | Q | X1 | X2 | X3 | X4 | X5 | Physical constant |
|---|---|---|---|---|---|---|---|---|
| 343 | 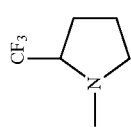 | —CN | —H | —H | —CF₃ | —H | —H | 94-96 |
| 344 | 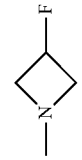 | —CN | —F | —H | —Cl | T003 | —H | 94-96 |
| 345 | 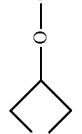 | —CN | —F | —H | —Cl | T003 | —H | 95-97 |
| 346 | 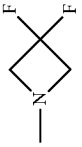 | —CN | —F | —H | —Cl | T003 | —H | 20.7° C. 1.5569 |
| 347 | 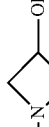 | —CN | —F | —H | —Cl | T003 | —H | 121-124 |
| 348 | 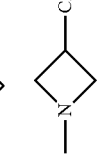 | —CN | —F | —H | —Cl | T003 | —H | 22° C. 1.5920 |
| 349 | 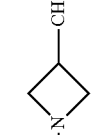 | —CN | —F | —H | —Cl | T003 | —H | 22.8° C. 1.5783 |
| 350 | 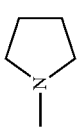 | —CN | —F | —H | —Cl | 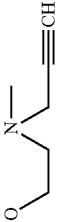 | —H | 102-105 |
| 351 | 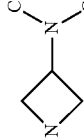 | —CN | —F | —H | —Cl | T003 | —H | 98-101 |
| 352 | 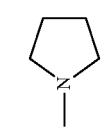 | —CN | —F | —H | —Cl | T021 | —H | 84-86 |

TABLE 3-continued

| No. | G | Q | X1 | X2 | X3 | X4 | X5 | Physical constant |
|---|---|---|---|---|---|---|---|---|
| 353 | 1-methylpyrrolidin-2-yl | —CN | —F | —H | —Cl | T030 | —H | 20.8° C. 1.5609 |
| 354 | 1-methylpyrrolidin-2-yl | —CN | —F | —H | —Cl | —OCH$_2$C$_2$F$_5$ | —H | 62-65 |
| 355 | 1-methylpyrrolidin-2-yl | —CN | —F | —H | —Cl | X150 | —H | 17.1° C. 1.5221 |
| 356 | 1-methylpyrrolidin-2-yl | —CN | —F | —H | —Cl | X152 | —H | 22.5° C. 1.5235 |
| 357 | 1-methylpyrrolidin-2-yl | —CN | —F | —H | —Cl | X153 | —H | 71-74 |
| 358 | 3,3,4,4-tetrafluoro-1-methylpyrrolidin-2-yl | —CN | —H | —H | —H | T003 | —H | 23.4° C. 1.5208 |
| 359 | 2-phenyl-1-methylazetidin-2-yl | —CN | —F | —H | —Cl | T003 | —H | 20.5° C. 1.6050 |
| 360 | 2,2-dimethyl-1-methylazetidin-3-yl | —CN | —F | —H | —Cl | T003 | —H | 20.5° C. 1.5700 |
| 361 | 1-methylpyrrolidin-2-yl | —CN | —F | —H | —Cl | X265 | —H | 20.7° C. 1.4995 |
| 362 | 1-methylpyrrolidin-2-yl | —CN | —F | —H | —Cl | X266 | —H | 86-88 |

TABLE 3-continued
| No. | G | Q | X1 | X2 | X3 | X4 | X5 | Physical constant |
|---|---|---|---|---|---|---|---|---|
| 363 |  | —CN | —F | —H | —Cl | X267 | —H | 20.5° C. 1.5228 |
| 364 |  | —CN | —F | —H | —Cl | X268 | —H | 106-108 |
| 365 | 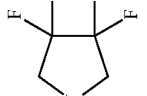 | —CN | —F | —H | —Cl | T031 | —H | 20.6° C. 1.5035 |
| 366 | 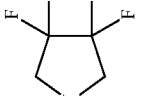 | —CN | —F | —H | —Cl | T032 | —H | 111-113 |
| 367 | 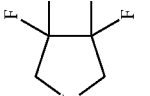 | —CN | —F | —H | —Cl | T033 | —H | 20.7° C. 1.5452 |
| 368 | 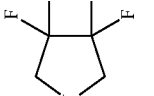 | —CN | —F | —H | —Cl | T034 | —H | 82-85 |
| 369 | 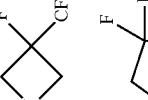 | —CN | —F | —H | —Cl | T003 | —H | 21° C. 1.5268 |
| 370 |  | —CN | —F | —H | —Cl | T035 | —H | 101-103 |

TABLE 3-continued
| No. | G | Q | X1 | X2 | X3 | X4 | X5 | Physical constant |
|---|---|---|---|---|---|---|---|---|
| 371 | 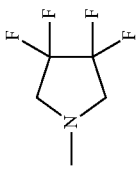 | —CN | —F | —H | —Cl | T036 | —H | 20.6° C. 1.5510 |
| 372 | 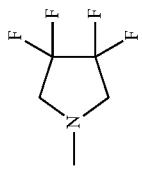 | —CN | —F | —H | —Cl | T037 | —H | 20.5° C. 1.5128 |
| 373 | 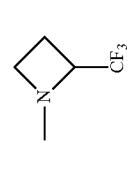 | —CN | —F | —H | —Cl | T003 | —H | 20.2° C. 1.5418 |
| 374 | 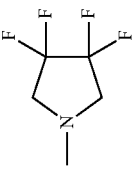 | —CN | —F | —H | —Cl | T038 | —H | 89-91 |
| 375 | 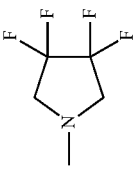 | —CN | —F | —H | —Cl | T039 | —H | 77-80 |
| 376 | 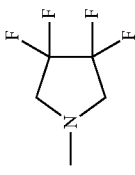 | —CN | —F | —H | —Cl | T040 | —H | 20.5° C. 1.5383 |
| 377 | 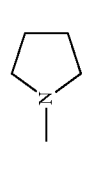 | —CN | —F | —H | —Cl | T040 | —H | 20.4° C. 1.5913 |

TABLE 3-continued
| No. | G | Q | X1 | X2 | X3 | X4 | X5 | Physical constant |
|---|---|---|---|---|---|---|---|---|
| 378 | 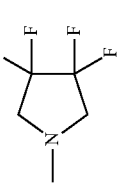 | —CN | —F | —H | —Cl | T041 | —H | 20.4° C. 1.5353 |
| 379 | 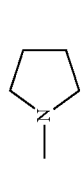 | —CN | —F | —H | —Cl | T041 | —H | 20.4° C. 1.5874 |
| 380 | 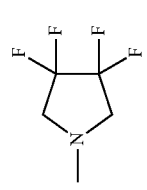 | —CN | —F | —H | —Cl | T042 | —H | 144-148 |
| 381 | 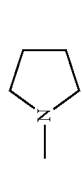 | —CN | —F | —H | —Cl | C001 | —H | 20.4° C. 1.5587 |
| 382 |  | —CN | —F | —H | —Cl | —CHO | —H | 85-88 |
| 383 | 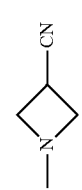 | —CN | —F | —H | —Cl | T003 | —H | 166-168 |
| 384 | 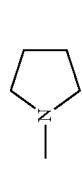 | —CN | F | H | F | T003 | H | 20.5° C. 1.5528 |
| 385 | 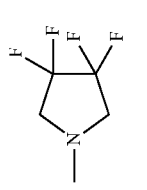 | —CN | F | H | F | T043 | H | 20.7° C. 1.5192 |
| 386 | 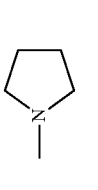 | —CN | F | H | Cl |  | H | 130-132 |

TABLE 3-continued

| No. | G | Q | X1 | X2 | X3 | X4 | X5 | Physical constant |
|-----|---|---|----|----|----|----|-----|-------------------|
| 387 | 3,3,4,4-tetrafluoropyrrolidinyl (N-Me) | —CN | F | H | Br | T003 | H | 81-84 |
| 388 | pyrrolidinyl (N-Me) | —CN | F | H | Cl | X303 | H | 20.6° C. 1.5514 |
| 389 | pyrrolidinyl (N-Me) | —CN | F | H | Cl | T044 | H | 20.5° C. 1.5744 |
| 390 | 3,3,4,4-tetrafluoropyrrolidinyl (N-Me) | —CN | F | H | Cl | T045 | —NO2 | 156-158 |
| 391 | 3,3,4,4-tetrafluoropyrrolidinyl (N-Me) | —CN | F | H | Cl | T045 | —NH2 | 201-204 |
| 392 | 3,3,4,4-tetrafluoropyrrolidinyl (N-Me) | —CN | F | H | Cl | X304 | H | 148-150 |
| 393 | pyrrolidinyl (N-Me) | —CN | F | H | Cl | X304 | H | 20.7° C. 1.5612 |
| 394 | pyrrolidinyl (N-Me) | —CN | F | H | Cl | T046 | H | 40-42 |
| 395 | pyrrolidinyl (N-Me) | —CN | F | H | Cl | T047 | H | 55-57 |

TABLE 3-continued
| No. | G | Q | X1 | X2 | X3 | X4 | X5 | Physical constant |
|---|---|---|---|---|---|---|---|---|
| 396 | 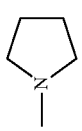 | —CN | F | H | Cl | T048 | H | 20.4° C. 1.5704 |
| 397 | 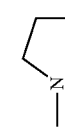 | —CN | F | H | Cl | T049 | H | 55-57 |
| 398 | 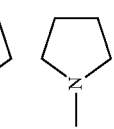 | —CN | F | H | Cl | 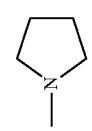 | H | VISCOUS OIL |
| 399 | 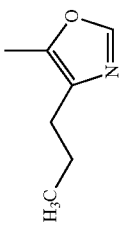 | —CN | F | H | Cl | T050 | H | 114-116 |
| 400 | 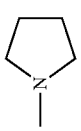 | —CN | F | H | Cl | T051 | H | 123-125 |
| 401 | 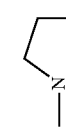 | —CN | F | H | Cl | T052 | H | 20.5° C. 1.5506 |
| 402 | 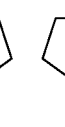 | —CN | F | H | Cl | T053 | H | 20.7° C. 1.5308 |
| 403 | 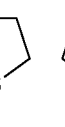 | —CN | F | H | Cl | T054 | H | 94-96 |
| 404 | 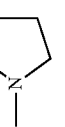 | —CN | F | H | Cl | X305 | H | 55-57 |
| 405 | 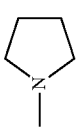 | —CN | F | H | Cl | T055 | H | 20.3° C. 1.5543 |

TABLE 3-continued
| No. | G | Q | X1 | X2 | X3 | X4 | X5 | Physical constant |
|---|---|---|---|---|---|---|---|---|
| 406 | 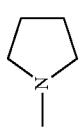 | —CN | F | H | Cl | X306 | H | VISCOUS OIL |
| 407 | 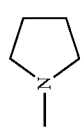 | —CN | F | H | Cl | X307 | H | 62-64 |
| 408 | 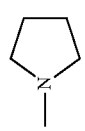 | —CN | F | H | Cl | X308 | H | VISCOUS OIL |
| 409 | 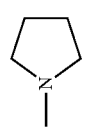 | —CN | F | H | Cl | X309 | H | 64-66 |
| 410 | 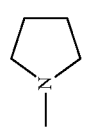 | —CN | F | H | Cl | X310 | H | 59-61 |
| 411 | 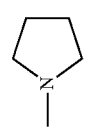 | —CN | F | H | Cl | T056 | H | 20.4° C. 1.5434 |
| 412 | 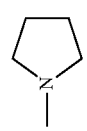 | —CN | F | H | Cl | T057 | H | 80-83 |
| 413 | 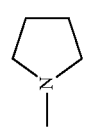 | —CN | F | H | Cl | T058 | H | 60-62 |
| 414 | 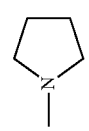 | —CN | F | H | Cl | T059 | H | 104-105 |
| 415 | 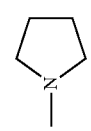 | —CN | F | H | Cl | T060 | H | AMORPHOUS |
| 416 | 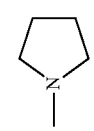 | —CN | F | H | Cl | X311 | H | 113-115 |

TABLE 3-continued
| No. | G | Q | X1 | X2 | X3 | X4 | X5 | Physical constant |
|---|---|---|---|---|---|---|---|---|
| 417 | 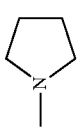 | —CN | F | H | Cl | X312 | H | AMORPHOUS |
| 418 | 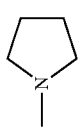 | —CN | F | H | Cl | X313 | H | 99-101 |
| 419 | 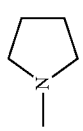 | —CN | F | H | Cl | T061 | H | 119-121 |
| 420 | 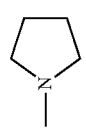 | —CN | F | H | Cl | T062 | H | 123-125 |
| 421 | 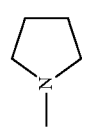 | —CN | F | H | Cl | T063 | H | 20.2° C. 1.5425 |
| 422 | 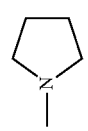 | —CN | F | H | Cl | T064 | H | 93-96 |
| 423 | 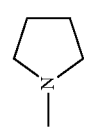 | —CN | F | H | Cl | X314 | H | VISCOUS OIL |
| 424 | 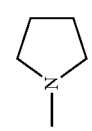 | —CN | F | H | Cl | X315 | H | 103-105 |
| 425 | 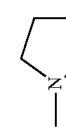 | —CN | F | H | Cl | X316 | H | 88-90 |
| 426 | 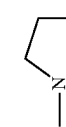 | —CN | F | H | Cl | T065 | H | 115-117 |
| 427 | 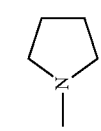 | —CN | | | | 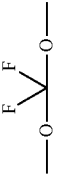 | H | 20.5° C. 1.5338 |

TABLE 3-continued
| No. | G | Q | X1 | X2 | X3 | X4 | X5 | Physical constant |
|---|---|---|---|---|---|---|---|---|
| 428 | 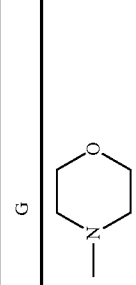 | —CN | F | H |  | | H | 115-117 |
| 429 |  | —CN | F | H | Cl | T066 | H | VISCOUS OIL |
| 430 |  | —CN | F | H | Cl | T003 | H | AMORPHOUS |
| 431 |  | —CN | F | H | Cl | T003 | H | 20.4° C. 1.5502 |
| 432 | 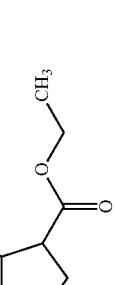 | —CN | F | H | Cl | X317 | H | VISCOUS OIL |
| 433 |  | —CN | F | H | Cl | X318 | H | 79-81 |
| 434 | 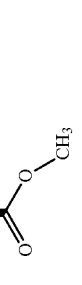 | —CN | F | H | Cl | X319 | H | VISCOUS OIL |
| 435 | 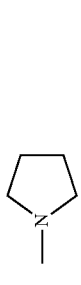 | —CN | F | H | Cl | T067 | H | 94-97 |

TABLE 3-continued
| No. | G | Q | X1 | X2 | X3 | X4 | X5 | Physical constant |
|---|---|---|---|---|---|---|---|---|
| 436 |  | —CN | F | H | Cl | T003 | H | VISCOUS OIL |
| 437 |  | —CN | F | H | Cl | X320 | H | VISCOUS OIL |
| 438 |  | —CN | F | H | Cl | T068 | H | 109-111 |
| 439 |  | —CN | F | H | Cl | T069 | H | 50-52 |
| 440 |  | —CN | F | H | Cl | T070 | H | VISCOUS OIL |
| 441 |  | —CN | F | H | Cl | T070 | H | 99-100 |
| 442 |  | —CN | F | H | Cl | T071 | H | VISCOUS OIL |
| 443 |  | —CN | F | H | Cl | X321 | H | VISCOUS OIL |
| 444 |  | —CN | F | H | Cl | T072 | H | 102-104 |
| 445 |  | —CN | F | H | Cl | T073 | H | 19.9° C. 1.5564 |

TABLE 3-continued
| No. | G | Q | X1 | X2 | X3 | X4 | X5 | Physical constant |
|---|---|---|---|---|---|---|---|---|
| 446 | 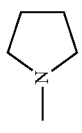 | —CN | F | H |  | F | H | 20.5° C. 1.5142 |
| 447 | 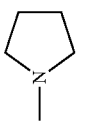 | —CN | F | H | Cl | T074 | H | 62-65 |
| 448 | 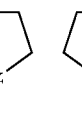 | —CN | F | H | Cl | T075 | H | 66-69 |
| 449 | 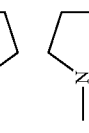 | —CN | F | H | Cl | T076 | H | 97-99 |
| 450 | 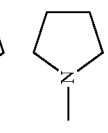 | —CN | F | H | Cl | T077 | H | 20.9° C. 1.5753 |
| 451 | 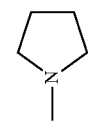 | —CN | F | H | Cl | X322 | H | AMORPHOUS |
| 452 | 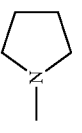 | —CN | F | H | Cl | T078 | H | 135-137 |
| 453 | 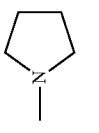 | —CN | F | H | Cl | T079 | H | 20.7° C. 1.4856 |
| 454 | 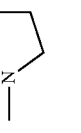 | —CN | F | H | Cl | T080 | H | 20.7° C. 1.5276 |
| 455 |  | —CN | F | H | Cl | X323 | H | VISCOUS OIL |

TABLE 3-continued
| No. | G | Q | X1 | X2 | X3 | X4 | X5 | Physical constant |
|---|---|---|---|---|---|---|---|---|
| 456 | 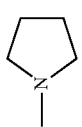 | —CN | F | H | Cl | X324 | H | 111-113 |
| 457 | 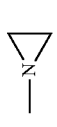 | —CN | F | H | CO2Et | N001 | H | |
| 458 |  | —CH=NOH | Cl | H | SMe | N002 | H | |
| 459 | 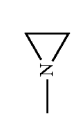 | —CH=NOCH₂Ph | Br | H | Br | N003 | H | |
| 460 |  | NH₂C(=O)– | NEt2 | SPh | H | N007 | H | |
| 461 |  | NMe₂C(=O)– | OMe | H | H | S001 | H | |
| 462 |  | pyrrolidinyl-C(=O)– | Bn | H | Cl | S002 | H | |
| 463 | 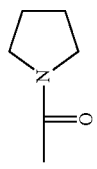 | morpholinyl-C(=O)– | SH | H | NEt2 | S003 | H | |
| 464 | 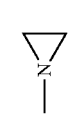 | NH₂C(=S)– | SMe | H | H | S004 | H | |
| 465 | 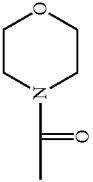 | NMe₂C(=S)– | Me | H | H | S005 | H | |
| 466 |  | pyrrolidinyl-C(=S)– | CH=CH2 | OCF3 | H | S006 | H | |
| 467 | 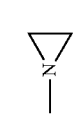 | morpholinyl-C(=S)– | C≡CH | Me | H | S007 | H | |

TABLE 3-continued
| No. | G | Q | X1 | X2 | X3 | X4 | X5 | Physical constant |
|---|---|---|---|---|---|---|---|---|
| 468 | 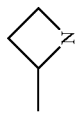 | 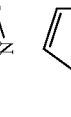 | Ac | NO2 | H | S008 | H | |
| 469 | 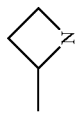 | 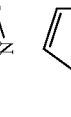 | CO2Et | H | H | S009 | H | |
| 470 | 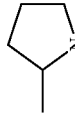 | 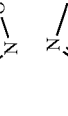 | COPh | H | H | H001 | H | |
| 471 | 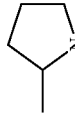 | 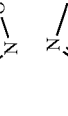 | H | CN | H | H002 | H | |
| 472 | 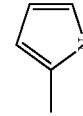 | 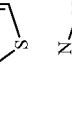 | CONH2 | H | H | H003 | H | |
| 473 | 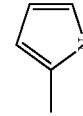 | 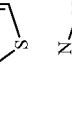 | T001 | CF3 | H | Br | H | |
| 474 | 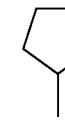 | 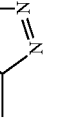 | T002 | OiPr | H | H | H | |
| 475 | 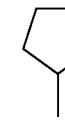 | 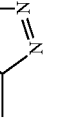 | T003 | OCONH | H | H | H | |
| 476 | 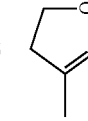 | 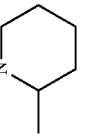 | T004 | Bn | H | H | H | |
| 477 | 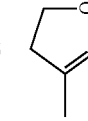 | 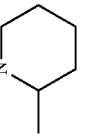 | T005 | NEt2 | H | H | H | |

TABLE 3-continued

| No. | G | Q | X1 | X2 | X3 | X4 | X5 | Physical constant |
|---|---|---|---|---|---|---|---|---|
| 478 | N-triangle | N-N piperidinyl-Me | T006 | OH | H | H | H | |
| 479 | N-triangle | pyrimidinyl-Me | T007 | Br | H | H | H | |
| 480 | N-triangle | pyridazinyl-Me | T008 | Cl | H | H | H | |
| 481 | N-triangle | pyridinyl-Me | T009 | F | H | H | H | |
| 482 | N-triangle | pyrazinyl-Me | Me | T010 | F | H | CO2Et | |
| 483 | N-triangle | pyrazinyl-Me | F | T011 | Cl | H | SMe | |
| 484 | N-square | —CN | Cl | T012 | Br | H | Br | |
| 485 | N-square | —CH=NOH | Br | T013 | CN | H | Me | |
| 486 | N-square | —CH=NOCH$_2$Ph | CN | T014 | NO2 | H | Et | |
| 487 | N-square | —C(=O)NH$_2$ | CF3 | T018 | Bn | H | Cl | |

TABLE 3-continued
| No. | G | Q | X1 | X2 | X3 | X4 | X5 | Physical constant |
|---|---|---|---|---|---|---|---|---|
| 488 | 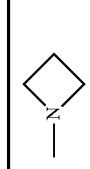 | 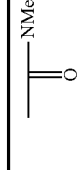 NMe2 | CO2Me | T019 | SH | H | NEt2 | |
| 489 |  | pyrrolidine-C(O)- | F | H004 | SMe | H | H | |
| 490 | 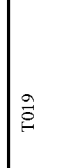 | morpholine-C(O)- | Cl | H005 | Me | H | H | |
| 491 | 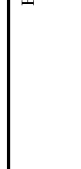 | NH2-C(S)- | H | H006 | CH=CH2 | OCF3 | H | |
| 492 |  | NMe2-C(S)- | H | H007 | ≡ | Me | H | |
| 493 | 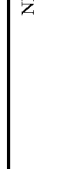 | pyrrolidine-C(S)- | H | X101 | Ac | NO2 | H | |
| 494 | 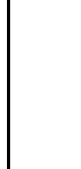 | morpholine-C(S)- | CO2Et | X102 | CO2Et | H | H | |
| 495 |  | azetidine | Et | X103 | COPh | H | H | |
| 496 |  | pyrrolidine | iPr | X104 | H | CN | H | |
| 497 |  | pyrrole | Me | X105 | CONH2 | H | H | |

TABLE 3-continued
| No. | G | Q | X1 | X2 | X3 | X4 | X5 | Physical constant |
|---|---|---|---|---|---|---|---|---|
| 498 | 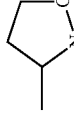 |  | Bn | X106 | Cl | Me | Bn | |
| 499 | 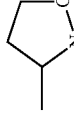 |  | SH | X107 | NEt2 | F | NEt2 | |
| 500 | 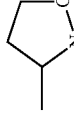 | 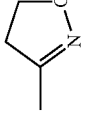 | SMe | X108 | H | Cl | OH | |
| 501 | 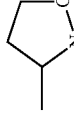 | 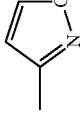 | Me | X109 | H | Br | Br | |
| 502 | 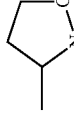 | 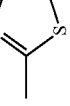 | CH=CH2 | X110 | H | CN | Cl | |
| 503 | 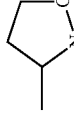 | 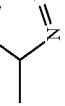 | ≡ | X111 | H | H | F | |
| 504 | 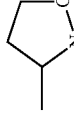 | 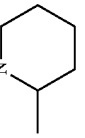 | Ac | X112 | H | Me | SH | |
| 505 | 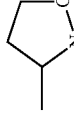 | 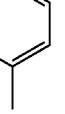 | CO2Et | X113 | H | F | SMe | |
| 506 | 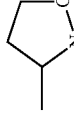 | 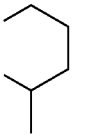 | COPh | X114 | H | CF3 | Me | |
| 507 | 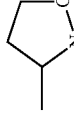 | 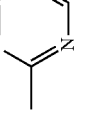 | H | X115 | H | CO2Me | CH=CH2 | |

TABLE 3-continued

| No. | G | Q | X1 | X2 | X3 | X4 | X5 | Physical constant |
|---|---|---|---|---|---|---|---|---|
| 508 | azetidinyl | 3-methylpiperidinyl | CONH2 | X116 | H | F | ≡ | |
| 509 | azetidinyl | 3-methylpyrazinyl | H | Ac | X117 | Cl | H | |
| 510 | azetidinyl | 3-methylpyrazinyl | H | CO2Et | X118 | H | H | |
| 511 | pyrrolidinyl | —CN | Cl | COPh | X119 | H | H | |
| 512 | pyrrolidinyl | —CH=NOH | NEt2 | H | X120 | H | H | |
| 513 | pyrrolidinyl | —CH=NOCH2Ph | H | CONH2 | X121 | CO2Et | H | |
| 514 | pyrrolidinyl | C(O)NH2 | H | H | X125 | Me | Me | |
| 515 | pyrrolidinyl | C(O)NMe2 | H | H | X126 | F | F | |
| 516 | pyrrolidinyl | C(O)-pyrrolidinyl | H | H | X127 | CF3 | Cl | |
| 517 | pyrrolidinyl | C(O)-morpholinyl | H | H | X128 | CO2Me | Br | |

TABLE 3-continued

| No. | G | Q | X1 | X2 | X3 | X4 | X5 | Physical constant |
|---|---|---|---|---|---|---|---|---|
| 518 | pyrrolidine-N | C(=S)NH₂ | H | H | X129 | F | CN | |
| 519 | pyrrolidine-N | C(=S)NMe₂ | H | H | X130 | Cl | H | |
| 520 | pyrrolidine-N | C(=S)-pyrrolidine | H | H | X131 | H | Me | |
| 521 | pyrrolidine-N | C(=S)-morpholine | H | H | X132 | H | F | |
| 522 | pyrrolidine-N | azetidine-Me | H | H | X133 | H | CF3 | |
| 523 | pyrrolidine-N | pyrrolidine-Me | H | H | X134 | CO2Et | CO2Me | |
| 524 | pyrrolidine-N | pyrrole-Me | H | H | X135 | Et | H | |
| 525 | pyrrolidine-N | isoxazolidine-Me | H | H | X136 | iPr | H | |
| 526 | pyrrolidine-N | isoxazoline-Me | H | H | X137 | Me | H | |
| 527 | pyrrolidine-N | isoxazole-Me | H | H | X138 | Me | H | |

TABLE 3-continued
| No. | G | Q | X1 | X2 | X3 | X4 | X5 | Physical constant |
|---|---|---|---|---|---|---|---|---|
| 528 |  |  | H | H | X139 | F | H | |
| 529 | 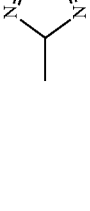 |  | H | H | X140 | CF3 | H | |
| 530 |  |  | H | H | X141 | CO2Me | H | |
| 531 |  |  | Br | F | X142 | H | H | |
| 532 |  |  | H | Cl | X143 | H | H | |
| 533 |  |  | H | Br | X144 | H | H | |
| 534 |  |  | H | CN | X145 | H | H | |
| 535 | 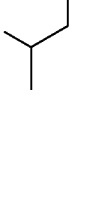 |  | H | NO2 | X146 | H | H | |
| 536 |  |  | H | OH | X147 | H | F | |
| 537 |  |  | H | NEt2 | X148 | H | Cl | |

TABLE 3-continued
| No. | G | Q | X1 | X2 | X3 | X4 | X5 | Physical constant |
|---|---|---|---|---|---|---|---|---|
| 538 | 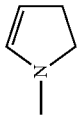 | —CN | H | OMe | H | X201 | Br | |
| 539 | 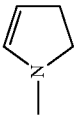 | —CH=NOH | H | Bn | H | X202 | CN | |
| 540 | 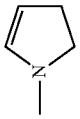 | —CH=NOCH₂Ph | H | SH | H | X203 | OH | |
| 541 | 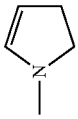 | C(=O)NH₂ | H | ≡ | H | X207 | SH | |
| 542 | 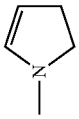 | C(=O)NMe₂ | Me | Ac | H | X208 | F | |
| 543 | 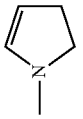 | C(=O)-pyrrolidine | SPh | CO2Et | H | X209 | Cl | |
| 544 | 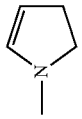 | C(=O)-morpholine | H | COPh | H | X210 | Br | |
| 545 | 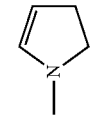 | C(=S)NH₂ | H | H | Me | X211 | CN | |
| 546 | 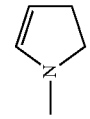 | C(=S)NMe₂ | H | CONH2 | H | X212 | NO2 | |
| 547 | 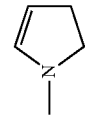 | C(=S)-pyrrolidine | H | H | H | X213 | OH | |

TABLE 3-continued
| No. | G | Q | X1 | X2 | X3 | X4 | X5 | Physical constant |
|---|---|---|---|---|---|---|---|---|
| 548 | 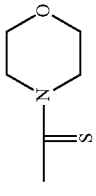 | 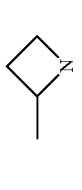 | H | H | H | X214 | NEt2 | |
| 549 | 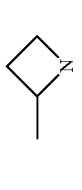 |  | OCF3 | H | H | X215 | OMe | |
| 550 | 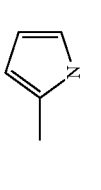 | 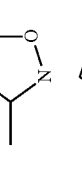 | Me | H | H | X216 | Bn | |
| 551 | 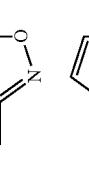 | 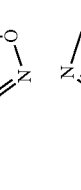 | NO2 | H | H | X217 | SH | |
| 552 | 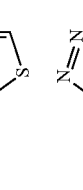 | 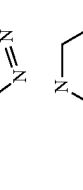 | H | H | H | X218 | SMe | |
| 553 | 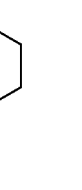 |  | H | H | H | X219 | OMe | |
| 554 |  | | CN | H | H | X220 | Bn | |
| 555 | | | H | H | H | X221 | SH | |
| 556 | | | H | H | H | X222 | SMe | |
| 557 | | | H | H | H | X223 | Me | |

TABLE 3-continued
| No. | G | Q | X1 | X2 | X3 | X4 | X5 | Physical constant |
|---|---|---|---|---|---|---|---|---|
| 558 |  |  | OCF3 | H | H | X224 | CH=CH2 | |
| 559 |  |  | Me | H | H | X225 | ≡ | |
| 560 |  |  | NO2 | H | H | X226 | Ac | |
| 561 |  |  | H | H | H | X227 | CO2Et | |
| 562 |  |  | H | H | H | X228 | COPh | |
| 563 |  |  | CN | H | H | X229 | H | |
| 564 |  |  | NO2 | CONEt2 | H | X230 | H | |
| 565 | | —CN | CONH2 | F | H | CO2Et | X231 | |
| 566 | | —CH=NOH | H | Cl | H | SMe | X232 | |
| 567 | | —CH=NOCH2Ph | H | Br | H | Br | X233 | |

TABLE 3-continued

| No. | G | Q | X1 | X2 | X3 | X4 | X5 | Physical constant |
|---|---|---|---|---|---|---|---|---|
| 568 | pyrrole-N | C(=O)NH2 | H | NEt2 | SPh | H | X237 | |
| 569 | pyrrole-N | C(=O)NMe2 | H | OMe | H | H | X238 | |
| 570 | pyrrole-N | C(=O)-pyrrolidine | H | Bn | H | Cl | X239 | |
| 571 | pyrrole-N | C(=O)-morpholine | H | SH | H | NEt2 | X240 | |
| 572 | pyrrole-N | C(=S)NH2 | H | SMe | H | H | X241 | |
| 573 | pyrrole-N | C(=S)NMe2 | H | Me | H | H | X242 | |
| 574 | pyrrole-N | C(=S)-pyrrolidine | H | CH=CH2 | OCF3 | H | X243 | |
| 575 | pyrrole-N | C(=S)-morpholine | H | C≡CH | Me | H | X244 | |
| 576 | pyrrole-N | azetidine-Me | H | Ac | NO2 | H | X245 | |
| 577 | pyrrole-N | pyrrolidine-Me | H | CO2Et | H | H | X246 | |

TABLE 3-continued
| No. | G | Q | X1 | X2 | X3 | X4 | X5 | Physical constant |
|---|---|---|---|---|---|---|---|---|
| 578 | 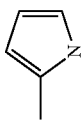 |  | H | COPh | H | H | X247 | |
| 579 | 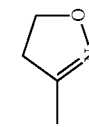 | 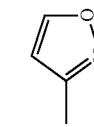 | H | H | CN | H | X248 | |
| 580 | 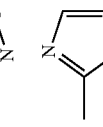 | 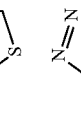 | CONEt2 | CONH2 | H | H | X249 | |
| 581 | 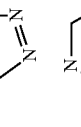 | 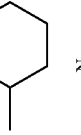 | Me | H | CO2Et | H | X250 | |
| 582 | 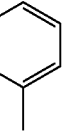 | 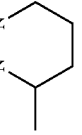 | NO2 | H | SMe | H | X251 | |
| 583 | 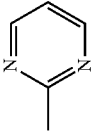 |  | H | H | Br | H | X252 | |
| 584 |  |  | H | H | Me | H | X253 | |
| 585 | | | CN | H | Et | H | X254 | |
| 586 | | | H | Me | Me | H | X255 | |
| 587 | | | CF3 | SPh | H | H | X256 | |

TABLE 3-continued
| No. | G | Q | X1 | X2 | X3 | X4 | X5 | Physical constant |
|---|---|---|---|---|---|---|---|---|
| 588 | 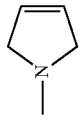 |  | CN | H | H | Me | X257 | |
| 589 | 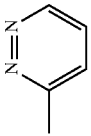 |  | NO2 | H | Cl | H | X258 | |
| 590 |  |  | Br | H | NEt2 | H | X259 | |
| 591 | 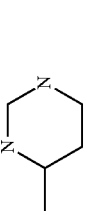 |  | CF3 | H | H | H | X260 | |
| 592 |  | —CN | X261 | H | H | H | Cl | |
| 593 | 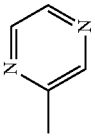 | —CH=NOH | X302 | OCF3 | H | H | CO2Et | |
| 594 |  | —CH=NOCH₂Ph | F | H | CO2Et | N001 | H | |
| 595 | 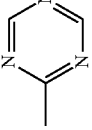 |  | NO2 | H | Et | N005 | H | |
| 596 |  | 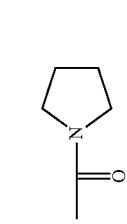 | OH | Me | Me | N006 | H | |
| 597 |  |  | NEt2 | SPh | H | N007 | H | |

TABLE 3-continued
| No. | G | Q | X1 | X2 | X3 | X4 | X5 | Physical constant |
|---|---|---|---|---|---|---|---|---|
| 598 | 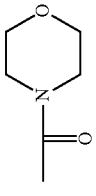 | 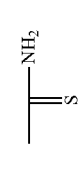 | OMe | H | H | S001 | H | |
| 599 | 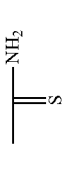 | 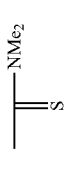 | Bn | H | Cl | S002 | H | |
| 600 | 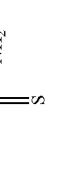 | 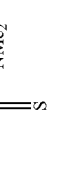 | SH | H | NEt2 | S003 | H | |
| 601 | 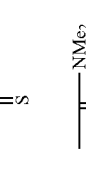 | 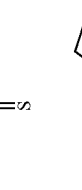 | SMe | H | H | S004 | H | |
| 602 | 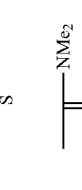 | 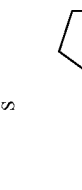 | Me | H | H | S005 | H | |
| 603 | 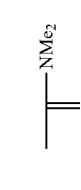 |  | CH=CH2 | OCF3 | H | S006 | H | |
| 604 | 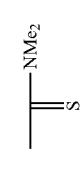 | 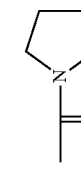 | ≡ | Me | H | S007 | H | |
| 605 | 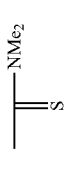 | 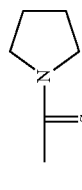 | Ac | NO2 | H | S008 | H | |
| 606 | 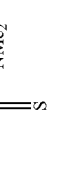 | 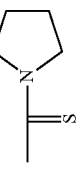 | CO2Et | H | H | S009 | H | |
| 607 | 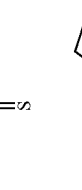 | 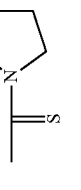 | COPh | H | H | H001 | H | |

TABLE 3-continued

| No. | G | Q | X1 | X2 | X3 | X4 | X5 | Physical constant |
|---|---|---|---|---|---|---|---|---|
| 608 | imidazole | isoxazole | H | CN | H | H002 | H | |
| 609 | imidazole | thiazole | CONH2 | H | H | H003 | H | |
| 610 | imidazole | tetrazole | T001 | CF3 | H | Br | H | |
| 611 | imidazole | piperidine | T002 | OiPr | H | H | H | |
| 612 | imidazole | pyridine | T003 | OCONH | H | H | H | |
| 613 | imidazole | piperidine | T004 | Bn | H | H | H | |
| 614 | imidazole | pyridine | T005 | NEt2 | H | H | H | |
| 615 | imidazole | pyridazine | T006 | OH | H | H | H | |
| 616 | imidazole | piperidine | T007 | Br | H | H | H | |
| 617 | imidazole | pyrazine | T008 | Cl | H | H | H | |

TABLE 3-continued

| No. | G | Q | X1 | X2 | X3 | X4 | X5 | Physical constant |
|---|---|---|---|---|---|---|---|---|
| 618 | N-methylimidazole | 2-methylpyrazine | T009 | F | H | H | H | |
| 619 | N-methylpyrrole | —CN | Me | T010 | F | H | CO2Et | |
| 620 | N-methylpyrrole | —CH=NOH | F | T011 | Cl | H | SMe | |
| 621 | N-methylpyrrole | —CH=NOCH2Ph | Cl | T012 | Br | H | Br | |
| 622 | N-methylpyrrole | C(=O)NH2 | Me | T016 | NEt2 | SPh | H | |
| 623 | N-methylpyrrole | C(=O)NMe2 | F | T017 | OMe | H | H | |
| 624 | N-methylpyrrole | pyrrolidinyl-C(=O) | CF3 | T018 | Bn | H | Cl | |
| 625 | N-methylpyrrole | morpholinyl-C(=O) | CO2Me | T019 | SH | H | NEt2 | |
| 626 | N-methylpyrrole | C(=S)NH2 | F | H004 | SMe | H | H | |
| 627 | N-methylpyrrole | C(=S)NMe2 | Cl | H005 | Me | H | H | |

TABLE 3-continued
| No. | G | Q | X1 | X2 | X3 | X4 | X5 | Physical constant |
|---|---|---|---|---|---|---|---|---|
| 628 |  | 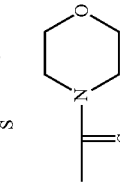 | H | H006 | CH=CH2 | OCF3 | H | |
| 629 | 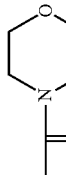 | 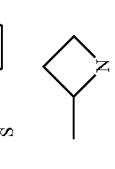 | H | H007 | ≡ | Me | H | |
| 630 | 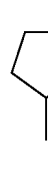 |  | H | X101 | Ac | NO2 | H | |
| 631 | 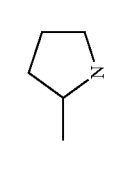 | 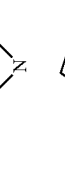 | CO2Et | X102 | CO2Et | H | H | |
| 632 | 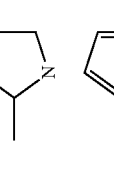 | 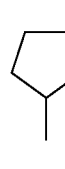 | Et | X103 | COPh | H | H | |
| 633 | 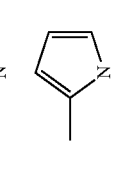 | 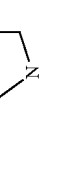 | iPr | X104 | H | CN | H | |
| 634 | 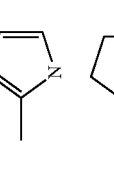 | 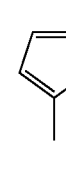 | Me | X105 | CONH2 | H | H | |
| 635 | 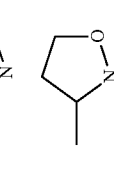 | 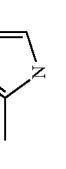 | Bn | X106 | Cl | Me | Bn | |
| 636 | 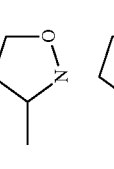 | 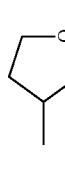 | SH | X107 | NEt2 | F | NEt2 | |
| 637 | 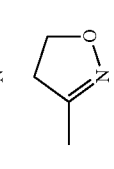 | 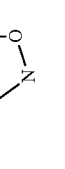 | SMe | X108 | H | Cl | OH | |

TABLE 3-continued
| No. | G | Q | X1 | X2 | X3 | X4 | X5 | Physical constant |
|---|---|---|---|---|---|---|---|---|
| 638 | 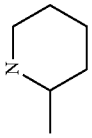 | 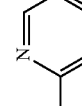 | Me | X109 | H | Br | Br | |
| 639 | 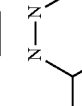 | 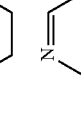 | CH=CH2 | X110 | H | CN | Cl | |
| 640 | 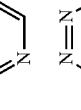 | 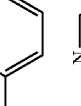 | C≡CH | X111 | H | H | F | |
| 641 |  | 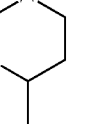 | Ac | X112 | H | Me | SH | |
| 642 | 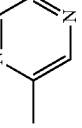 | 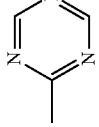 | CO2Et | X113 | H | F | SMe | |
| 643 |  |  | COPh | X114 | H | CF3 | Me | |
| 644 |  |  | H | X115 | H | CO2Me | CH=CH2 | |
| 645 |  |  | CONH2 | X116 | H | F | C≡CH | |
| 646 | | —CN | H | Ac | X117 | Cl | H | |
| 647 | | —CH=NOH | H | CO2Et | X118 | H | H | |

TABLE 3-continued

| No. | G | Q | X1 | X2 | X3 | X4 | X5 | Physical constant |
|---|---|---|---|---|---|---|---|---|
| 648 | pyrazole | —CH=NOCH₂Ph | Cl | COPh | X119 | H | H | |
| 649 | pyrazole | C(=O)NH₂ | H | H | X123 | iPr | H | |
| 650 | pyrazole | C(=O)NMe₂ | H | H | X124 | Me | H | |
| 651 | pyrazole | C(=O)-pyrrolidine | H | H | X125 | Me | Me | |
| 652 | pyrazole | C(=O)-morpholine | H | H | X126 | F | F | |
| 653 | pyrazole | C(=S)NH₂ | H | H | X127 | CF3 | Cl | |
| 654 | pyrazole | C(=S)NMe₂ | H | H | X128 | CO2Me | Br | |
| 655 | pyrazole | C(=S)-pyrrolidine | H | H | X129 | F | CN | |
| 656 | pyrazole | C(=S)-morpholine | H | H | X130 | Cl | H | |
| 657 | pyrazole | azetidine | H | H | X131 | H | Me | |

TABLE 3-continued

| No. | G | Q | X1 | X2 | X3 | X4 | X5 | Physical constant |
|---|---|---|---|---|---|---|---|---|
| 658 | pyrazole | pyrrolidine-Me | H | H | X132 | H | F | |
| 659 | pyrazole | pyrrole-Me | H | H | X133 | H | CF3 | |
| 660 | pyrazole | isoxazoline-Me | H | H | X134 | CO2Et | CO2Me | |
| 661 | pyrazole | isoxazoline-Me | H | H | X135 | Et | H | |
| 662 | pyrazole | isoxazole-Me | H | H | X136 | iPr | H | |
| 663 | pyrazole | thiazole-Me | H | H | X137 | Me | H | |
| 664 | pyrazole | tetrazole-Me | H | H | X138 | Me | H | |
| 665 | pyrazole | piperidine-Me | H | H | X139 | F | H | |
| 666 | pyrazole | pyridine-Me | H | H | X140 | CF3 | H | |
| 667 | pyrazole | hexahydropyridazine-Me | H | H | X141 | CO2Me | H | |

TABLE 3-continued
| No. | G | Q | X1 | X2 | X3 | X4 | X5 | Physical constant |
|---|---|---|---|---|---|---|---|---|
| 668 |  |  | Br | F | X142 | H | H | |
| 669 |  |  | H | Cl | X143 | H | H | |
| 670 | 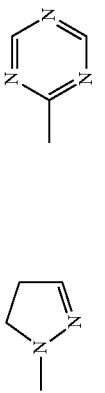 |  | H | Br | X144 | H | H | |
| 671 |  |  | H | CN | X145 | H | H | |
| 672 |  |  | H | NO2 | X146 | H | H | |
| 673 | pyrazole | —CN | H | OH | X147 | H | F | |
| 674 | pyrazole | —CH=NOH | H | NEt2 | X148 | H | Cl | |
| 675 | pyrazole | —CH=NOCH2Ph | H | OMe | H | X201 | Br | |
| 676 | pyrazole | —C(=O)NH2 | H | Me | H | X205 | OMe | |
| 677 | pyrazole | —C(=O)NMe2 | H | CH=CH | H | X206 | Bn | |

TABLE 3-continued
| No. | G | Q | X1 | X2 | X3 | X4 | X5 | Physical constant |
|---|---|---|---|---|---|---|---|---|
| 678 | 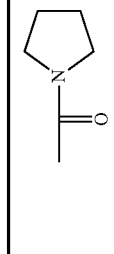 | 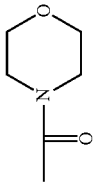 | H | ≡ | H | X207 | SH | |
| 679 |  | 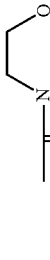 | Me | Ac | H | X208 | F | |
| 680 | 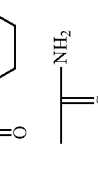 | 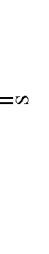 | SPh | CO2Et | H | X209 | Cl | |
| 681 | 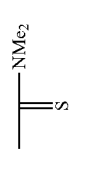 |  | H | COPh | H | X210 | Br | |
| 682 | 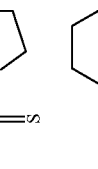 | 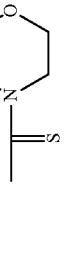 | H | H | Me | X211 | CN | |
| 683 | 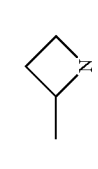 |  | H | CONH2 | H | X212 | NO2 | |
| 684 | 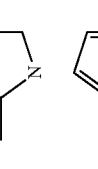 |  | H | H | H | X213 | OH | |
| 685 | 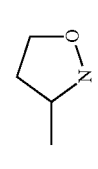 |  | H | H | H | X214 | NEt2 | |
| 686 |  |  | OCF3 | H | H | X215 | OMe | |
| 687 |  | | Me | H | H | X216 | Bn | |

TABLE 3-continued
| No. | G | Q | X1 | X2 | X3 | X4 | X5 | Physical constant |
|---|---|---|---|---|---|---|---|---|
| 688 | 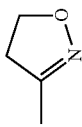 |  | NO2 | H | H | X217 | SH | |
| 689 | 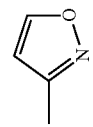 |  | H | H | H | X218 | SMe | |
| 690 | 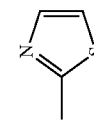 |  | H | H | H | X219 | OMe | |
| 691 | 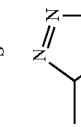 |  | CN | H | H | X220 | Bn | |
| 692 | 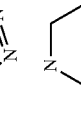 | 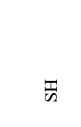 | H | H | H | X221 | SH | |
| 693 | 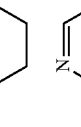 |  | H | H | H | X222 | SMe | |
| 694 | 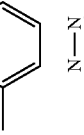 |  | H | H | H | X223 | Me | |
| 695 | 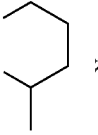 | 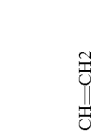 | OCF3 | H | H | X224 | CH=CH2 | |
| 696 | 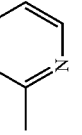 |  | Me | H | H | X225 | ≡ | |
| 697 |  | 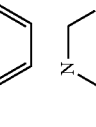 | NO2 | H | H | X226 | Ac | |

TABLE 3-continued
| No. | G | Q | X1 | X2 | X3 | X4 | X5 | Physical constant |
|---|---|---|---|---|---|---|---|---|
| 698 |  |  | H | H | H | X227 | CO2Et | |
| 699 |  |  | H | H | H | X228 | COPh | |
| 700 |  | —CN | CN | H | H | X229 | H | |
| 701 |  | —CH=NOH | NO2 | CONEt2 | H | X230 | H | |
| 702 |  | —CH=NOCH₂Ph | CONH2 | F | H | CO2Et | X231 | |
| 703 |  | 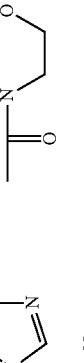 | H | NO2 | H | Et | X235 | |
| 704 |  |  | H | OH | Me | Me | X236 | |
| 705 |  | 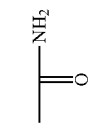 | H | NEt2 | SPh | H | X237 | |
| 706 | 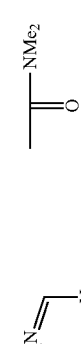 |  | H | OMe | H | H | X238 | |
| 707 | 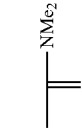 |  | H | Bn | H | Cl | X239 | |

TABLE 3-continued

| No. | G | Q | X1 | X2 | X3 | X4 | X5 | Physical constant |
|---|---|---|---|---|---|---|---|---|
| 708 | imidazolyl | C(=S)NMe2 | H | SH | H | NEt2 | X240 | |
| 709 | imidazolyl | pyrrolidinyl-C(=S)- | H | SMe | H | H | X241 | |
| 710 | imidazolyl | morpholinyl-C(=S)- | H | Me | H | H | X242 | |
| 711 | imidazolyl | azetidinyl | H | CH=CH2 | OCF3 | H | X243 | |
| 712 | imidazolyl | pyrrolidinyl | H | C≡CH | Me | H | X244 | |
| 713 | imidazolyl | pyrrolyl | H | Ac | NO2 | H | X245 | |
| 714 | imidazolyl | isoxazolidinyl | H | CO2Et | H | H | X246 | |
| 715 | imidazolyl | isoxazolinyl | H | COPh | H | H | X247 | |
| 716 | imidazolyl | isoxazolyl | H | H | CN | H | X248 | |
| 717 | imidazolyl | thiazolyl | CONEt2 | CONH2 | H | H | X249 | |

TABLE 3-continued

| No. | G | Q | X1 | X2 | X3 | X4 | X5 | Physical constant |
|---|---|---|---|---|---|---|---|---|
| 718 | imidazole | methyltetrazole | Me | H | CO2Et | H | X250 | |
| 719 | imidazole | 2-methylpiperidine | NO2 | H | SMe | H | X251 | |
| 720 | imidazole | 2-methylpyridine | H | H | Br | H | X252 | |
| 721 | imidazole | 2-methyltetrahydropyridine | H | H | Me | H | X253 | |
| 722 | imidazole | 2-methylpyrimidine | CN | H | Et | H | X254 | |
| 723 | imidazole | 2-methylpyridazine | H | Me | Me | H | X255 | |
| 724 | imidazole | 4-methylpiperidine | CF3 | SPh | H | H | X256 | |
| 725 | imidazole | 5-methylpyrazine | CN | H | H | Me | X257 | |
| 726 | imidazole | 2-methylpyrazine | NO2 | H | Cl | H | X258 | |
| 727 | oxazole | —CN | Br | H | NEt2 | H | X259 | |

TABLE 3-continued
| No. | G | Q | X1 | X2 | X3 | X4 | X5 | Physical constant |
|---|---|---|---|---|---|---|---|---|
| 728 |  | —CH=NOH | CF3 | H | H | H | X260 | |
| 729 |  | —CH=NOCH2Ph | X261 | H | H | H | Cl | |
| 730 |  |  NH2 | Br | H | Br | N003 | H | |
| 731 | 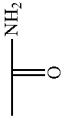 |  NMe2 | CN | H | Me | N004 | H | |
| 732 |  |  | NO2 | H | Et | N005 | H | |
| 733 | 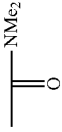 | 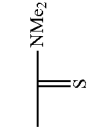 | OH | Me | Me | N006 | H | |
| 734 |  |  NH2 | NEt2 | SPh | H | N007 | H | |
| 735 | 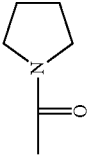 |  NMe2 | OMe | H | H | S001 | H | |
| 736 |  |  | Bn | H | Cl | S002 | H | |
| 737 |  |  | SH | H | NEt2 | S003 | H | |

TABLE 3-continued
| No. | G | Q | X1 | X2 | X3 | X4 | X5 | Physical constant |
|---|---|---|---|---|---|---|---|---|
| 738 | 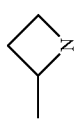 |  | SMe | H | H | S004 | H | |
| 739 | 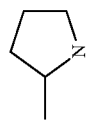 |  | Me | H | H | S005 | H | |
| 740 |  |  | CH=CH2 | OCF3 | H | S006 | H | |
| 741 | 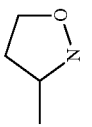 |  | ≡ | H | H | S007 | H | |
| 742 | 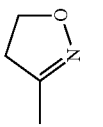 |  | Ac | Me | H | S008 | H | |
| 743 | 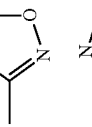 |  | CO2Et | NO2 | H | S009 | H | |
| 744 | 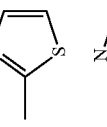 |  | COPh | H | H | H001 | H | |
| 745 | 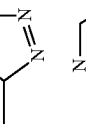 |  | H | CN | H | H002 | H | |
| 746 | 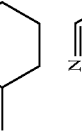 |  | CONH2 | H | H | H003 | H | |
| 747 | 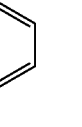 |  | T001 | CF3 | H | Br | H | |

TABLE 3-continued
| No. | G | Q | X1 | X2 | X3 | X4 | X5 | Physical constant |
|---|---|---|---|---|---|---|---|---|
| 748 |  |  | T002 | OiPr | H | H | H | |
| 749 |  |  | T003 | OCONH | H | H | H | |
| 750 |  |  | T004 | Bn | H | H | H | |
| 751 | 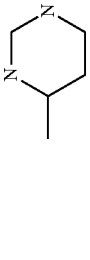 |  | T005 | NEt2 | H | H | H | |
| 752 |  |  | T006 | OH | H | H | H | |
| 753 | 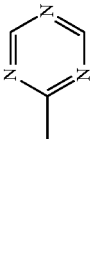 |  | T007 | Br | H | H | H | |
| 754 | 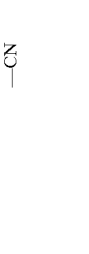 | —CN | T008 | Cl | H | H | H | |
| 755 |  | —CH=NOH | T009 | F | H | H | H | |
| 756 |  | —CH=NOCH₂Ph | Me | T010 | F | H | CO2Et | |
| 757 |  |  | CN | T014 | NO2 | H | Et | |

TABLE 3-continued
| No. | G | Q | X1 | X2 | X3 | X4 | X5 | Physical constant |
|---|---|---|---|---|---|---|---|---|
| 758 |  |  | H | T015 | OH | Me | Me | |
| 759 |  |  | Me | T016 | NEt2 | SPh | H | |
| 760 |  |  | F | T017 | OMe | H | H | |
| 761 |  |  | CF3 | T018 | Bn | H | Cl | |
| 762 |  |  | CO2Me | T019 | SH | H | NEt2 | |
| 763 |  |  | F | H004 | SMe | H | H | |
| 764 |  |  | Cl | H005 | Me | H | H | |
| 765 |  |  | H | H006 | CH=CH2 | OCF3 | H | |
| 766 |  |  | H | H007 | C≡CH | Me | H | |
| 767 |  |  | H | X101 | Ac | NO2 | H | |

TABLE 3-continued

| No. | G | Q | X1 | X2 | X3 | X4 | X5 | Physical constant |
|---|---|---|---|---|---|---|---|---|
| 768 | N-methylpyrazole | 3-methylisoxazolidine | CO2Et | | CO2Et | H | H | |
| 769 | N-methylpyrazole | 3-methyl-4,5-dihydroisoxazole | Et | X102 | COPh | H | H | |
| 770 | N-methylpyrazole | 3-methylisoxazole | iPr | X103 | H | CN | H | |
| 771 | N-methylpyrazole | 2-methylthiazole | Me | X104 | CONH2 | H | H | |
| 772 | N-methylpyrazole | 5-methyl-tetrazole | Bn | X105 | Cl | Me | Bn | |
| 773 | N-methylpyrazole | 2-methylpiperidine | SH | X106 | NEt2 | F | NEt2 | |
| 774 | N-methylpyrazole | 2-methylpyridine | SMe | X107 | H | Cl | OH | |
| 775 | N-methylpyrazole | 3-methylhexahydropyridazine | Me | X108 | H | Br | Br | |
| 776 | N-methylpyrazole | 2-methylpyrimidine | CH=CH2 | X109 | H | CN | Cl | |
| 777 | N-methylpyrazole | 3-methylpyridazine | C≡CH | X110 | H | H | F | |

TABLE 3-continued

| No. | G | Q | X1 | X2 | X3 | X4 | X5 | Physical constant |
|---|---|---|---|---|---|---|---|---|
| 778 | imidazole | methylpiperidine | Ac | X112 | H | Me | SH | |
| 779 | imidazole | methylpyrazine | CO2Et | X113 | H | F | SMe | |
| 780 | imidazole | methylpyrazine | COPh | X114 | H | CF3 | Me | |
| 781 | isoxazolidine | —CN | H | X115 | H | CO2Me | CH=CH2 | |
| 782 | isoxazolidine | —CH=NOH | CONH2 | X116 | H | F | C≡CH | |
| 783 | isoxazolidine | —CH=NOCH2Ph | H | Ac | X117 | Cl | H | |
| 784 | isoxazolidine | C(O)NH2 | H | CONH2 | X121 | CO2Et | H | |
| 785 | isoxazolidine | C(O)NMe2 | H | H | X122 | Et | H | |
| 786 | isoxazolidine | C(O)-pyrrolidine | H | H | X123 | iPr | H | |
| 787 | isoxazolidine | C(O)-morpholine | H | H | X124 | Me | H | |

TABLE 3-continued
| No. | G | Q | X1 | X2 | X3 | X4 | X5 | Physical constant |
|---|---|---|---|---|---|---|---|---|
| 788 | 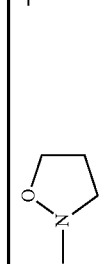 |  | H | H | X125 | Me | Me | |
| 789 |  |  | H | H | X126 | F | F | |
| 790 |  |  | H | H | X127 | CF3 | Cl | |
| 791 |  |  | H | H | X128 | CO2Me | Br | |
| 792 |  |  | H | H | X129 | F | CN | |
| 793 |  |  | H | H | X130 | Cl | H | |
| 794 |  |  | H | H | X131 | H | Me | |
| 795 |  |  | H | H | X132 | H | F | |
| 796 |  |  | H | H | X133 | H | CF3 | |
| 797 |  |  | H | H | X134 | CO2Et | CO2Me | |

TABLE 3-continued
| No. | G | Q | X1 | X2 | X3 | X4 | X5 | Physical constant |
|---|---|---|---|---|---|---|---|---|
| 798 |  |  | H | H | X135 | Et | H | |
| 799 |  |  | H | H | X136 | iPr | H | |
| 800 |  |  | H | H | X137 | Me | H | |
| 801 |  |  | H | H | X138 | Me | H | |
| 802 |  |  | H | H | X139 | F | H | |
| 803 |  |  | H | H | X140 | CF3 | H | |
| 804 |  |  | H | H | X141 | CO2Me | H | |
| 805 |  |  | Br | F | X142 | H | H | |
| 806 |  |  | H | Cl | X143 | H | H | |
| 807 |  |  | H | Br | X144 | H | H | |

TABLE 3-continued
| No. | G | Q | X1 | X2 | X3 | X4 | X5 | Physical constant |
|---|---|---|---|---|---|---|---|---|
| 808 | 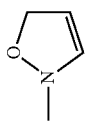 | —CN | H | CN | X145 | H | H | |
| 809 | 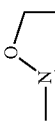 | —CH=NOH | H | NO2 | X146 | H | H | |
| 810 | 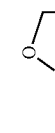 | —CH=NOCH₂Ph | H | OH | X147 | H | F | |
| 811 | 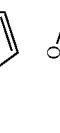 | C(=O)NH₂ | H | SH | H | X203 | OH | |
| 812 | 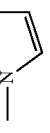 | C(=O)NMe₂ | H | SMe | H | X204 | NEt2 | |
| 813 | 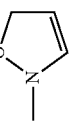 | C(=O)-pyrrolidinyl | H | Me | H | X205 | OMe | |
| 814 | 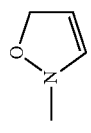 | C(=O)-morpholinyl | H | CH=CH2 | H | X206 | Bn | |
| 815 | 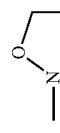 | C(=S)NH₂ | H | C≡CH | H | X207 | SH | |
| 816 | 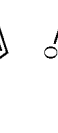 | C(=S)NMe₂ | Me | Ac | H | X208 | F | |
| 817 | 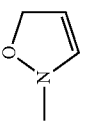 | C(=S)-pyrrolidinyl | SPh | CO2Et | H | X209 | Cl | |

TABLE 3-continued
| No. | G | Q | X1 | X2 | X3 | X4 | X5 | Physical constant |
|---|---|---|---|---|---|---|---|---|
| 818 | 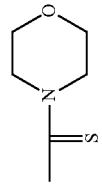 |  | H | COPh | H | X210 | Br | |
| 819 |  | 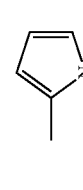 | H | H | Me | X211 | CN | |
| 820 | 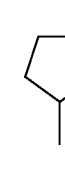 | 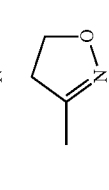 | H | CONH2 | H | X212 | NO2 | |
| 821 | | | H | H | H | X213 | OH | |
| 822 | | | H | H | H | X214 | NEt2 | |
| 823 | | | OCF3 | H | H | X215 | OMe | |
| 824 | | | Me | H | H | X216 | Bn | |
| 825 | | | NO2 | H | H | X217 | SH | |
| 826 | | | H | H | H | X218 | SMe | |
| 827 | | | H | H | H | X219 | OMe | |

TABLE 3-continued

| No. | G | Q | X1 | X2 | X3 | X4 | X5 | Physical constant |
|---|---|---|---|---|---|---|---|---|
| 828 | isoxazole-N | 2-methylpyridine | CN | H | H | X220 | Bn | |
| 829 | isoxazole-N | 3-methyl-tetrahydropyridazine | H | H | H | X221 | SH | |
| 830 | isoxazole-N | 2-methylpyrimidine | H | H | H | X222 | SMe | |
| 831 | isoxazole-N | 2-methylpyridazine | H | H | H | X223 | Me | |
| 832 | isoxazole-N | 4-methyl-tetrahydropyrazine | OCF3 | H | H | X224 | CH=CH2 | |
| 833 | isoxazole-N | 3-methylpyrazine | Me | H | H | X225 | ≡ | |
| 834 | isoxazole-N | 2-methylpyrazine | NO2 | H | H | X226 | Ac | |
| 835 | thiazolidine-N | —CN | H | H | H | X227 | CO2Et | |
| 836 | thiazolidine-N | —CH=NOH | H | H | H | X228 | COPh | |
| 837 | thiazolidine-N | —CH=NOCH2Ph | CN | H | H | X229 | H | |

TABLE 3-continued

| No. | G | Q | X1 | X2 | X3 | X4 | X5 | Physical constant |
|---|---|---|---|---|---|---|---|---|
| 838 | thiazolidinyl | C(O)NH₂ | H | Br | H | Br | X233 | |
| 839 | thiazolidinyl | C(O)NMe₂ | H | CN | H | Me | X234 | |
| 840 | thiazolidinyl | C(O)-pyrrolidinyl | H | NO2 | H | Et | X235 | |
| 841 | thiazolidinyl | C(O)-morpholinyl | H | OH | H | Me | X236 | |
| 842 | thiazolidinyl | C(S)NH₂ | H | NEt2 | SPh | H | X237 | |
| 843 | thiazolidinyl | C(S)NMe₂ | H | OMe | H | H | X238 | |
| 844 | thiazolidinyl | C(S)-pyrrolidinyl | H | Bn | H | Cl | X239 | |
| 845 | thiazolidinyl | C(S)-morpholinyl | H | SH | H | NEt2 | X240 | |
| 846 | thiazolidinyl | azetidinyl | H | SMe | H | H | X241 | |
| 847 | thiazolidinyl | pyrrolidinyl | H | Me | H | H | X242 | |

TABLE 3-continued
| No. | G | Q | X1 | X2 | X3 | X4 | X5 | Physical constant |
|---|---|---|---|---|---|---|---|---|
| 848 | 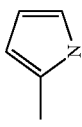 |  | H | CH=CH2 | OCF3 | H | X243 | |
| 849 | 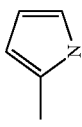 | 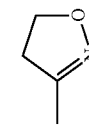 | H | ≡ | Me | H | X244 | |
| 850 | 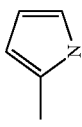 | 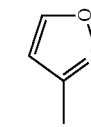 | H | Ac | NO2 | H | X245 | |
| 851 | 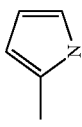 | 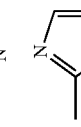 | H | CO2Et | H | H | X246 | |
| 852 | 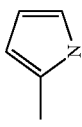 | 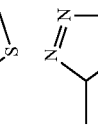 | H | COPh | H | H | X247 | |
| 853 | 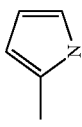 | 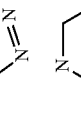 | H | H | CN | H | X248 | |
| 854 | 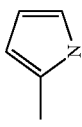 | 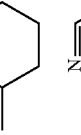 | CONEt2 | CONH2 | H | H | X249 | |
| 855 | 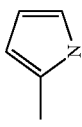 | 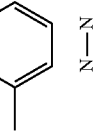 | Me | H | CO2Et | H | X250 | |
| 856 | 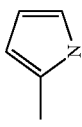 | 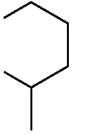 | NO2 | H | SMe | H | X251 | |
| 857 | 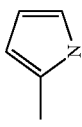 | 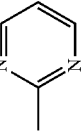 | H | H | Br | H | X252 | |

TABLE 3-continued

| No. | G | Q | X1 | X2 | X3 | X4 | X5 | Physical constant |
|---|---|---|---|---|---|---|---|---|
| 858 | thiazole-N | 2-methylpyridin-6-yl | H | H | Me | H | X253 | |
| 859 | thiazole-N | 2-methylpiperidin-6-yl | CN | H | Et | H | X254 | |
| 860 | thiazole-N | 2-methylpyrazin-6-yl | H | Me | Me | H | X255 | |
| 861 | thiazole-N | 2-methylpyrimidin-6-yl | CF3 | SPh | H | H | X256 | |
| 862 | thiazole-N | —CN | CN | H | H | Me | X257 | |
| 863 | thiazole-N | —CH=NOH | NO2 | H | Cl | H | X258 | |
| 864 | thiazole-N | —CH=NOCH2Ph | Br | H | NEt2 | H | X259 | |
| 865 | thiazole-N | —C(=O)NH2 | F | H | CO2Et | N001 | H | |
| 866 | thiazole-N | —C(=O)NMe2 | Cl | H | SMe | N002 | H | |
| 867 | thiazole-N | —C(=O)-pyrrolidin-1-yl | Br | H | Br | N003 | H | |

TABLE 3-continued
| No. | G | Q | X1 | X2 | X3 | X4 | X5 | Physical constant |
|---|---|---|---|---|---|---|---|---|
| 868 | 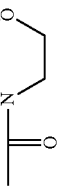 | 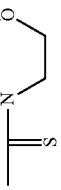 | CN | H | Me | N004 | H | |
| 869 |  |  | NO2 | H | Et | N005 | H | |
| 870 | 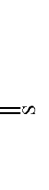 | 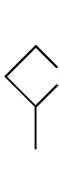 | OH | Me | Me | N006 | H | |
| 871 |  |  | NEt2 | SPh | H | N007 | H | |
| 872 | 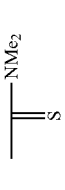 | 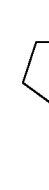 | OMe | H | H | S001 | H | |
| 873 |  |  | Bn | H | Cl | S002 | H | |
| 874 | 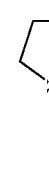 | 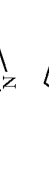 | SH | H | NEt2 | S003 | H | |
| 875 |  |  | SMe | H | H | S004 | H | |
| 876 |  | 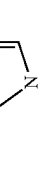 | Me | H | H | S005 | H | |
| 877 |  |  | CH=CH2 | OCF3 | H | S006 | H | |

TABLE 3-continued

| No. | G | Q | X1 | X2 | X3 | X4 | X5 | Physical constant |
|-----|---|---|----|----|----|----|----|-------------------|
| 878 | thiazole | 3-methylisoxazole | ≡ (ethynyl) | Me | H | S007 | H | |
| 879 | thiazole | 2-methylthiazole | Ac | NO2 | H | S008 | H | |
| 880 | thiazole | 5-methyltetrazole | CO2Et | H | H | S009 | H | |
| 881 | thiazole | 2-methylpiperidine | COPh | H | H | H001 | H | |
| 882 | thiazole | 2-methylpyridine | H | CN | H | H002 | H | |
| 883 | thiazole | 3-methylpiperidazine | CONH2 | H | H | H003 | H | |
| 884 | thiazole | 2-methylpyrimidine | T001 | CF3 | H | Br | H | |
| 885 | thiazole | 3-methylpyridazine | T002 | OiPr | H | H | H | |
| 886 | thiazole | 4-methylpiperazine | T003 | OCONH | H | H | H | |
| 887 | thiazole | 3-methylpyrazine | T004 | Bn | H | H | H | |

TABLE 3-continued
| No. | G | Q | X1 | X2 | X3 | X4 | X5 | Physical constant |
|-----|---|---|----|----|----|----|----|-------------------|
| 888 |  | 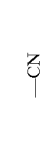 | T005 | NEt2 | H | H | H | |
| 889 |  | —CN | T006 | OH | H | H | H | |
| 890 |  | —CH=NOH | T007 | Br | H | H | H | |
| 891 |  | —CH=NOCH2Ph | T008 | Cl | H | H | H | |
| 892 |  | —NH2 | Cl | T012 | Br | H | Br | |
| 893 |  | —NMe2 | Br | T013 | CN | H | Me | |
| 894 |  |  | CN | T014 | NO2 | H | Et | |
| 895 | | | H | T015 | OH | Me | Me | |
| 896 | | —NH2 | Me | T016 | NEt2 | SPh | H | |
| 897 | | —NMe2 | F | T017 | OMe | H | H | |

TABLE 3-continued
| No. | G | Q | X1 | X2 | X3 | X4 | X5 | Physical constant |
|---|---|---|---|---|---|---|---|---|
| 898 |  | 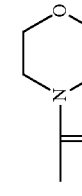 | CF3 | T018 | Bn | H | Cl | |
| 899 | 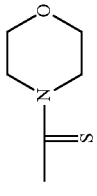 | 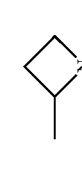 | CO2Me | T019 | SH | H | NEt2 | |
| 900 | 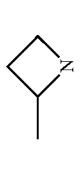 |  | F | H004 | SMe | H | H | |
| 901 | 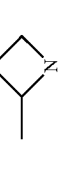 |  | Cl | H005 | Me | H | H | |
| 902 |  | 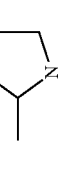 | H | H006 | CH=CH2 | OCF3 | H | |
| 903 | 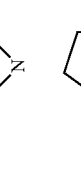 | 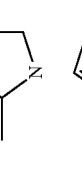 | H | H007 | ≡ | ME | H | |
| 904 | 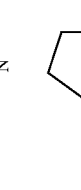 | 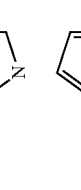 | H | X101 | Ac | NO2 | H | |
| 905 | 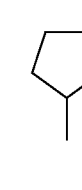 | 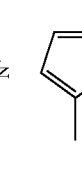 | CO2Et | X102 | CO2Et | H | H | |
| 906 |  | 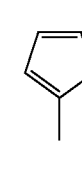 | Et | X103 | COPh | H | H | |
| 907 |  |  | iPr | X104 | H | CN | H | |

TABLE 3-continued

| No. | G | Q | X1 | X2 | X3 | X4 | X5 | Physical constant |
|---|---|---|---|---|---|---|---|---|
| 908 | N-piperidinyl | 2-methylpiperidinyl | Me | X105 | CONH2 | H | H | |
| 909 | N-piperidinyl | 2-methylpyridinyl | Bn | X106 | Cl | Me | Bn | |
| 910 | N-piperidinyl | 3-methyl-pyridazinyl | SH | X107 | NEt2 | F | NEt2 | |
| 911 | N-piperidinyl | 2-methylpyrimidinyl | SMe | X108 | H | Cl | OH | |
| 912 | N-piperidinyl | 3-methylpyridazinyl | Me | X109 | H | Br | Br | |
| 913 | N-piperidinyl | 4-methyl-pyrimidinyl | CH=CH2 | X110 | H | CN | Cl | |
| 914 | N-piperidinyl | 5-methylpyrimidinyl | C≡CH | X111 | H | H | F | |
| 915 | N-piperidinyl | 2-methylpyrazinyl | Ac | X112 | H | Me | SH | |
| 916 | N-pyrimidinyl | —CN | CO2Et | X113 | H | F | SMe | |
| 917 | N-pyrimidinyl | —CH=NOH | COPh | X114 | H | CF3 | Me | |

TABLE 3-continued
| No. | G | Q | X1 | X2 | X3 | X4 | X5 | Physical constant |
|---|---|---|---|---|---|---|---|---|
| 918 | 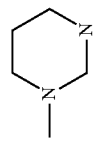 | —CH=NOCH₂Ph | H | X115 | H | CO2Me | CH=CH2 | |
| 919 | 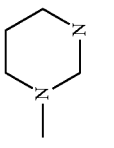 | C(=O)NH₂ | Cl | COPh | X119 | H | H | |
| 920 | 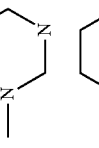 | C(=O)NMe₂ | NEt2 | H | X120 | H | H | |
| 921 | 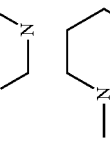 | pyrrolidine-C(=O) | H | CONH2 | X121 | CO2Et | H | |
| 922 | 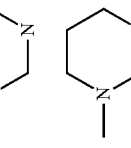 | morpholine-C(=O) | H | H | X122 | Et | H | |
| 923 | 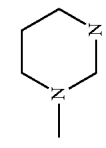 | C(=S)NH₂ | H | H | X123 | iPr | H | |
| 924 | 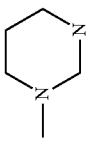 | C(=S)NMe₂ | H | H | X124 | Me | H | |
| 925 | 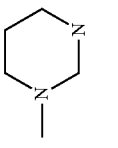 | pyrrolidine-C(=S) | H | H | X125 | Me | Me | |
| 926 |  | morpholine-C(=S) | H | H | X126 | F | F | |

TABLE 3-continued
| No. | G | Q | X1 | X2 | X3 | X4 | X5 | Physical constant |
|---|---|---|---|---|---|---|---|---|
| 927 | 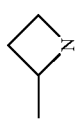 | 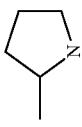 | H | H | X127 | CF3 | Cl | |
| 928 | | | H | H | X128 | CO2Me | Br | |
| 929 | | | H | H | X129 | F | CN | |
| 930 | | | H | H | X130 | Cl | H | |
| 931 | | | H | H | X131 | H | Me | |
| 932 | | | H | H | X132 | H | F | |
| 933 | | | H | H | X133 | H | CF3 | |
| 934 | | | H | H | X134 | CO2Et | CO2Me | |
| 935 | | | H | H | X135 | Et | H | |
| 936 | | | H | H | X136 | iPr | H | |

TABLE 3-continued

| No. | G | Q | X1 | X2 | X3 | X4 | X5 | Physical constant |
|---|---|---|---|---|---|---|---|---|
| 937 | N-methylpiperazinyl | 3-methyl-pyridazinyl | H | H | X137 | Me | H | |
| 938 | N-methylpiperazinyl | 6-methyl-pyrimidinyl | H | H | X138 | Me | H | |
| 939 | N-methylpiperazinyl | 6-methyl-pyridazinyl | H | H | X139 | F | H | |
| 940 | N-methylpiperazinyl | 2-methyl-pyrimidinyl | H | H | X140 | CF3 | H | |
| 941 | N-methylpiperazinyl | 2-methyl-pyrazinyl | Br | H | X141 | CO2Me | H | |
| 942 | N-methylpiperazinyl | 3-methyl-pyrazinyl | H | F | X142 | H | H | |
| 943 | N-methylpiperazinyl | —CN | H | Cl | X143 | H | H | |
| 944 | N-methylpiperazinyl | —CH=NOH | H | Br | X144 | H | H | |
| 945 | N-methylpiperazinyl | —CH=NOCH2Ph | H | CN | X145 | H | H | |
| 946 | N-methylpiperazinyl | —C(=O)NH2 | H | OMe | H | X201 | Br | |

TABLE 3-continued

| No. | G | Q | X1 | X2 | X3 | X4 | X5 | Physical constant |
|---|---|---|---|---|---|---|---|---|
| 947 | piperazine-N-Me | C(=O)-NMe2 | H | Bn | H | X202 | CN | |
| 948 | piperazine-N-Me | C(=O)-pyrrolidine | H | SH | H | X203 | OH | |
| 949 | piperazine-N-Me | C(=O)-morpholine | H | SMe | H | X204 | NEt2 | |
| 950 | piperazine-N-Me | C(=S)-NH2 | H | Me | H | X205 | OMe | |
| 951 | piperazine-N-Me | C(=S)-NMe2 | H | CH=CH2 | H | X206 | Bn | |
| 952 | piperazine-N-Me | C(=S)-pyrrolidine | H | C≡CH | H | X207 | SH | |
| 953 | piperazine-N-Me | C(=S)-morpholine | Me | Ac | H | X208 | F | |
| 954 | piperazine-N-Me | azetidine | SPh | CO2Et | H | X209 | Cl | |
| 955 | piperazine-N-Me | pyrrolidine | H | COPh | H | X210 | Br | |
| 956 | piperazine-N-Me | pyrrole | H | H | Me | X211 | CN | |

TABLE 3-continued

| No. | G | Q | X1 | X2 | X3 | X4 | X5 | Physical constant |
|---|---|---|---|---|---|---|---|---|
| 957 | piperazine | 3-methylisoxazolidine | H | CONH2 | H | X212 | NO2 | |
| 958 | piperazine | 3-methyl-4,5-dihydroisoxazole | H | H | H | X213 | OH | |
| 959 | piperazine | 3-methylisoxazole | H | H | H | X214 | NEt2 | |
| 960 | piperazine | 2-methylthiazole | OCF3 | H | H | X215 | OMe | |
| 961 | piperazine | 5-methyltetrazole | Me | H | H | X216 | Bn | |
| 962 | piperazine | 2-methylpiperidine | NO2 | H | H | X217 | SH | |
| 963 | piperazine | 2-methylpyridine | H | H | H | X218 | SMe | |
| 964 | piperazine | 3-methyltetrahydropyridazine | H | H | H | X219 | OMe | |
| 965 | piperazine | 2-methylpyrimidine | CN | H | H | X220 | Bn | |
| 966 | piperazine | 3-methylpyridazine | H | H | H | X221 | SH | |

TABLE 3-continued

| No. | G | Q | X1 | X2 | X3 | X4 | X5 | Physical constant |
|---|---|---|---|---|---|---|---|---|
| 967 | piperazinyl | 2-methylpiperidinyl (N,N) | H | H | H | X222 | SMe | |
| 968 | piperazinyl | 2-methylpyrazinyl | H | H | H | X223 | Me | |
| 969 | piperazinyl | 2-methylpyrazinyl | OCF3 | H | H | X224 | CH=CH2 | |
| 970 | morpholinyl | —CN | Me | H | H | X225 | C≡CH | |
| 971 | morpholinyl | —CH=NOH | NO2 | H | H | X226 | Ac | |
| 972 | morpholinyl | —CH=NOCH2Ph | H | F | H | X227 | CO2Et | |
| 973 | morpholinyl | C(=O)NH2 | CONH2 | Cl | H | CO2Et | X231 | |
| 974 | morpholinyl | C(=O)NMe2 | H | Br | H | SMe | X232 | |
| 975 | morpholinyl | pyrrolidinyl-C(=O) | H | H | H | Br | X233 | |

TABLE 3-continued

| No. | G | Q | X1 | X2 | X3 | X4 | X5 | Physical constant |
|---|---|---|---|---|---|---|---|---|
| 976 | N-morpholine | N-morpholine-C(=O)- | H | CN | H | Me | X234 | |
| 977 | N-morpholine | -C(=S)-NH2 | H | NO2 | H | Et | X235 | |
| 978 | N-morpholine | -C(=S)-NMe2 | H | OH | Me | Me | X236 | |
| 979 | N-morpholine | N-pyrrolidine-C(=S)- | H | NEt2 | SPh | H | X237 | |
| 980 | N-morpholine | N-morpholine-C(=S)- | H | OMe | H | H | X238 | |
| 981 | N-morpholine | azetidinyl | H | Bn | H | Cl | X239 | |
| 982 | N-morpholine | pyrrolidinyl | H | SH | H | NEt2 | X240 | |
| 983 | N-morpholine | pyrrolyl | H | SMe | H | H | X241 | |
| 984 | N-morpholine | isoxazolinyl | H | Me | H | H | X242 | |
| 985 | N-morpholine | isoxazolinyl | H | CH=CH2 | OCF3 | H | X243 | |

TABLE 3-continued
| No. | G | Q | X1 | X2 | X3 | X4 | X5 | Physical constant |
|---|---|---|---|---|---|---|---|---|
| 986 |  |  | H | ≡ | Me | H | X244 | |
| 987 |  |  | H | Ac | NO2 | H | X245 | |
| 988 |  |  | H | CO2Et | H | H | X246 | |
| 989 |  |  | H | COPh | H | H | X247 | |
| 990 |  |  | H | H | CN | H | X248 | |
| 991 |  |  | CONEt2 | CONH2 | H | H | X249 | |
| 992 |  |  | Me | H | CO2Et | H | X250 | |
| 993 |  |  | NO2 | H | SMe | H | X251 | |
| 994 |  |  | H | H | Br | H | X252 | |
| 995 |  | | H | H | Me | H | X253 | |

TABLE 3-continued
| No. | G | Q | X1 | X2 | X3 | X4 | X5 | Physical constant |
|---|---|---|---|---|---|---|---|---|
| 996 | 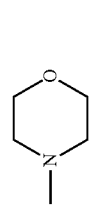 | 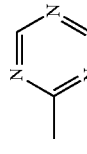 | CN | H | Et | H | X254 | |
| 997 |  | —CN | H | Me | Me | H | X255 | |
| 998 |  | —CH=NOH | CF3 | SPh | H | H | X256 | |
| 999 | 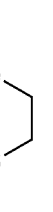 | —CH=NOCH₂Ph | CN | H | H | Me | X257 | |
| 1000 | 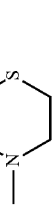 | 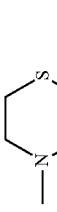 NH₂ | X261 | H | H | H | Cl | |
| 1001 | |  NMe₂ | X302 | OCF3 | H | H | CO2Et | |
| 1002 | |  | F | H | CO2Et | N001 | H | |
| 1003 | |  | Cl | H | SMe | N002 | H | |
| 1004 | | 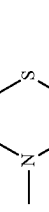 NH₂ | Br | H | Br | N003 | H | |
| 1005 | | NMe₂ | CN | H | Me | N004 | H | |

TABLE 3-continued
| No. | G | Q | X1 | X2 | X3 | X4 | X5 | Physical constant |
|---|---|---|---|---|---|---|---|---|
| 1006 | 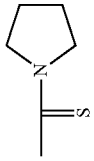 | 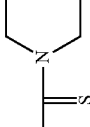 | NO2 | H | Et | N005 | H | |
| 1007 | 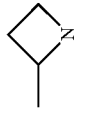 | 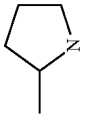 | OH | Me | Me | N006 | H | |
| 1008 | 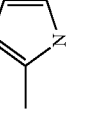 | 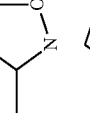 | NEt2 | SPh | H | N007 | H | |
| 1009 | 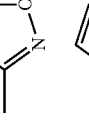 | 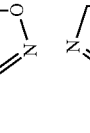 | OMe | H | H | S001 | H | |
| 1010 | 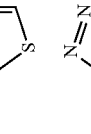 |  | Bn | H | Cl | S002 | H | |
| 1011 |  |  | SH | H | NEt2 | S003 | H | |
| 1012 | 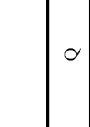 | 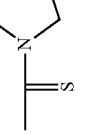 | SMe | H | H | S004 | H | |
| 1013 | 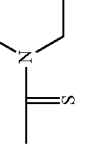 | 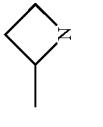 | Me | H | H | S005 | H | |
| 1014 | 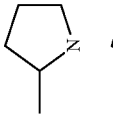 | 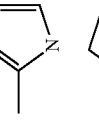 | CH=CH2 | OCF3 | H | S006 | H | |
| 1015 | 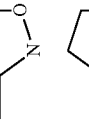 | 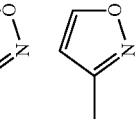 | ≡ | Me | H | S007 | H | |

TABLE 3-continued

| No. | G | Q | X1 | X2 | X3 | X4 | X5 | Physical constant |
|---|---|---|---|---|---|---|---|---|
| 1016 | | | Ac | NO2 | H | S008 | H | |
| 1017 | | | CO2Et | H | H | S009 | H | |
| 1018 | | | COPh | H | H | H001 | H | |
| 1019 | | | H | CN | H | H002 | H | |
| 1020 | | | CONH2 | H | H | H003 | H | |
| 1021 | | | T001 | CF3 | H | Br | H | |
| 1022 | | | T002 | OiPr | H | H | H | |
| 1023 | | | T003 | OCONH | H | H | H | |
| 1024 | | | T004 | Bn | H | H | H | |

TABLE 3-continued

| No. | G | Q | X1 | X2 | X3 | X4 | X5 | Physical constant |
|---|---|---|---|---|---|---|---|---|
| 1025 | azepane-N | —CH=NOH | T005 | NEt2 | H | H | H | |
| 1026 | azepane-N | —CH=NOCH2Ph | T006 | OH | H | H | H | |
| 1027 | azepane-N | C(=O)NH2 | Me | T010 | F | H | CO2Et | |
| 1028 | azepane-N | C(=O)NMe2 | F | T011 | Cl | H | SMe | |
| 1029 | azepane-N | C(=O)-pyrrolidine | Cl | T012 | Br | H | Br | |
| 1030 | azepane-N | C(=O)-morpholine | Br | T013 | CN | H | Me | |
| 1031 | azepane-N | C(=S)NH2 | CN | T014 | NO2 | H | Et | |
| 1032 | azepane-N | C(=S)NMe2 | H | T015 | OH | Me | Me | |

TABLE 3-continued
| No. | G | Q | X1 | X2 | X3 | X4 | X5 | Physical constant |
|---|---|---|---|---|---|---|---|---|
| 1033 |  |  | Me | T016 | NEt2 | SPh | H | |
| 1034 |  | 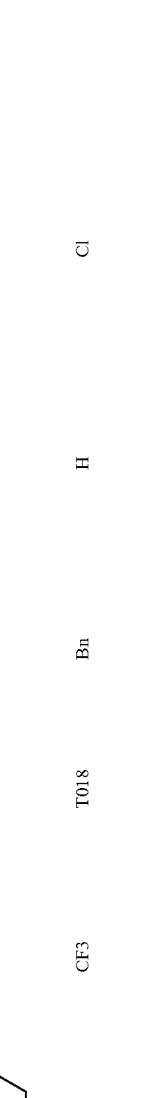 | F | T017 | OMe | H | H | |
| 1035 |  | 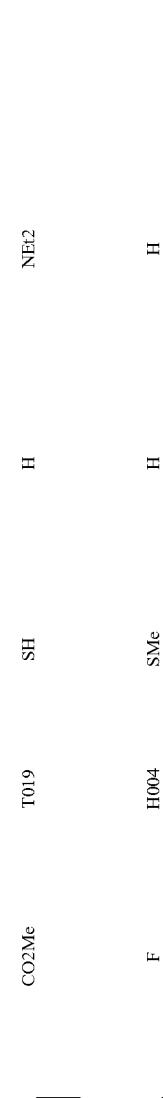 | CF3 | T018 | Bn | H | Cl | |
| 1036 |  | 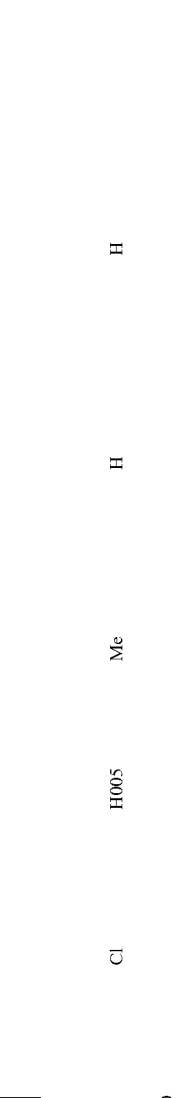 | CO2Me | T019 | SH | H | NEt2 | |
| 1037 |  | 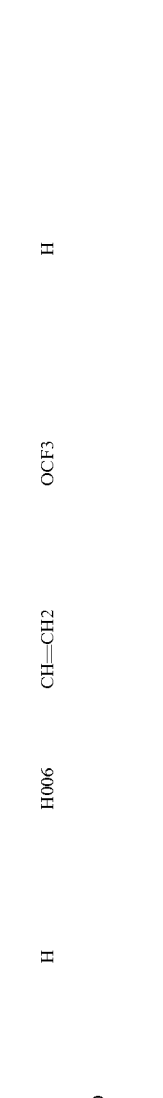 | F | H004 | SMe | H | H | |
| 1038 |  |  | Cl | H005 | Me | H | H | |
| 1039 |  |  | H | H006 | CH=CH2 | OCF3 | H | |
| 1040 | | | H | H007 | ≡ | Me | H | |

TABLE 3-continued
| No. | G | Q | X1 | X2 | X3 | X4 | X5 | Physical constant |
|---|---|---|---|---|---|---|---|---|
| 1041 |  | 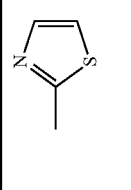 | H | X101 | Ac | NO2 | H | |
| 1042 | 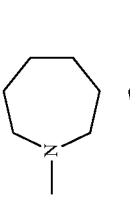 | 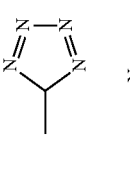 | CO2Et | X102 | CO2Et | H | H | |
| 1043 | 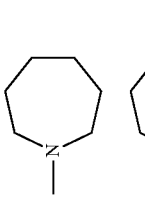 | 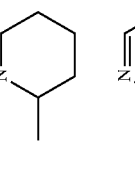 | Et | X103 | COPh | H | H | |
| 1044 | 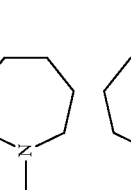 | 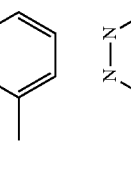 | iPr | X104 | H | CN | H | |
| 1045 | 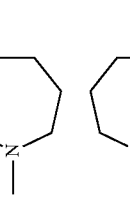 | 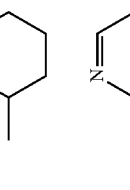 | Me | X105 | CONH2 | H | H | |
| 1046 | 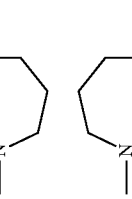 | 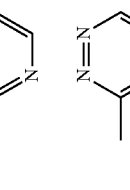 | Bn | X106 | Cl | Me | Bn | |
| 1047 | 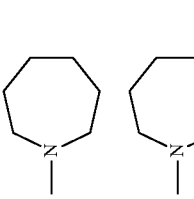 | 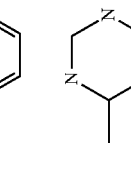 | SH | X107 | NEt2 | F | NEt2 | |
| 1048 | 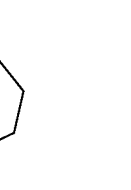 | 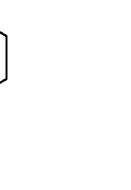 | SMe | X108 | H | Cl | OH | |

TABLE 3-continued
| No. | G | Q | X1 | X2 | X3 | X4 | X5 | Physical constant |
|---|---|---|---|---|---|---|---|---|
| 1049 | 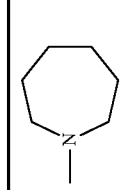 | 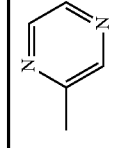 | Me | X109 | H | Br | Br | |
| 1050 | 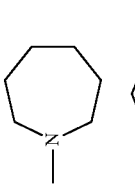 | 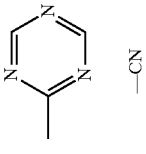 | CH=CH2 | X110 | H | CN | Cl | |
| 1051 | 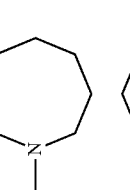 | —CN | ≡ | X111 | H | H | F | |
| 1052 | 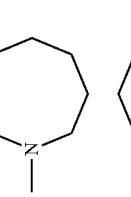 | —CH=NOH | Ac | X112 | H | Me | SH | |
| 1053 | 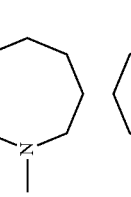 | —CH=NOCH$_2$Ph | CO2Et | X113 | H | F | SMe | |
| 1054 | 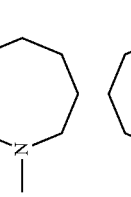 | 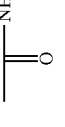 | H | Ac | X117 | Cl | H | |
| 1055 | 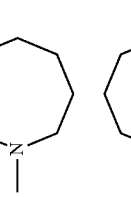 | 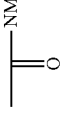 | H | CO2Et | X118 | H | H | |
| 1056 | 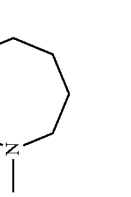 | 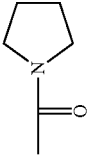 | Cl | COPh | X119 | H | H | |

TABLE 3-continued

| No. | G | Q | X1 | X2 | X3 | X4 | X5 | Physical constant |
|---|---|---|---|---|---|---|---|---|
| 1057 | N-azocane | morpholine-C(=O)- | NEt2 | H | X120 | H | H | |
| 1058 | N-azocane | NH2-C(=S)- | H | CONH2 | X121 | CO2Et | H | |
| 1059 | N-azocane | NMe2-C(=S)- | H | H | X122 | Et | H | |
| 1060 | N-azocane | pyrrolidine-C(=S)- | H | H | X123 | iPr | H | |
| 1061 | N-azocane | morpholine-C(=S)- | H | H | X124 | Me | H | |
| 1062 | N-azocane | azetidine-CH- | H | H | X125 | Me | Me | |
| 1063 | N-azocane | pyrrolidine-CH- | H | H | X126 | F | F | |

TABLE 3-continued
| No. | G | Q | X1 | X2 | X3 | X4 | X5 | Physical constant |
|---|---|---|---|---|---|---|---|---|
| 1064 | 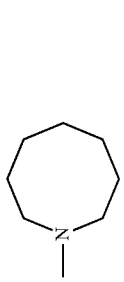 |  | H | H | X127 | CF3 | Cl | |
| 1065 | 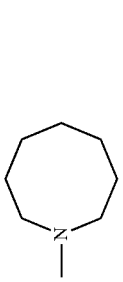 | 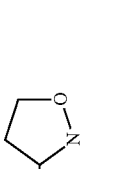 | H | H | X128 | CO2Me | Br | |
| 1066 | 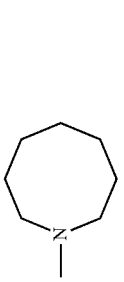 | 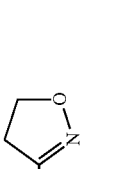 | H | H | X129 | F | CN | |
| 1067 | 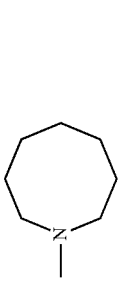 | 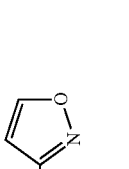 | H | H | X130 | Cl | H | |
| 1068 | 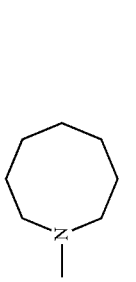 | 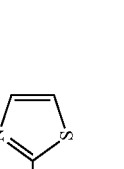 | H | H | X131 | H | Me | |
| 1069 | 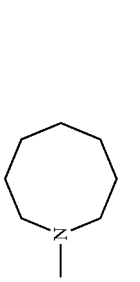 | 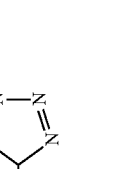 | H | H | X132 | H | F | |
| 1070 | 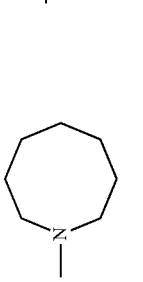 | 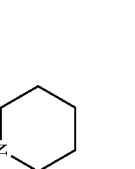 | H | H | X133 | H | CF3 | |

TABLE 3-continued

| No. | G | Q | X1 | X2 | X3 | X4 | X5 | Physical constant |
|---|---|---|---|---|---|---|---|---|
| 1071 | azocane-N-yl | 2-methylpyridin-yl | H | H | X134 | CO2Et | CO2Me | |
| 1072 | azocane-N-yl | 2-methylpiperidin-yl | H | H | X135 | Et | H | |
| 1073 | azocane-N-yl | 2-methylpyrimidin-yl | H | H | X136 | iPr | H | |
| 1074 | azocane-N-yl | 3-methylpyridazin-yl | H | H | X137 | Me | H | |
| 1075 | azocane-N-yl | 4-methylpyrimidin-yl | H | H | X138 | Me | H | |
| 1076 | azocane-N-yl | 3-methylpyrazin-yl | H | H | X139 | F | H | |
| 1077 | azocane-N-yl | 2-methylpyrazin-yl | H | H | X140 | CF3 | H | |
| 1078 | 1,1-dioxothiomorpholin-N-yl | —CN | H | H | X141 | CO2Me | H | |

TABLE 3-continued
| No. | G | Q | X1 | X2 | X3 | X4 | X5 | Physical constant |
|---|---|---|---|---|---|---|---|---|
| 1079 | 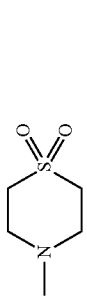 | —CH=NOH | Br | F | X142 | H | H | |
| 1080 | 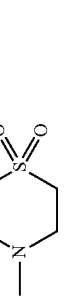 | —CH=NOCH₂Ph | H | Cl | X143 | H | H | |
| 1081 |  | 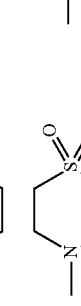 NH₂ | H | OH | X147 | H | F | |
| 1082 | | 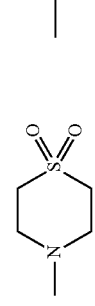 NMe₂ | H | NEt2 | X148 | H | Cl | |
| 1083 | | 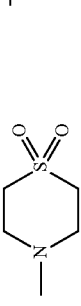 | H | OMe | H | X201 | Br | |
| 1084 | | 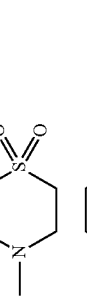 | H | Bn | H | X202 | CN | |
| 1085 | | 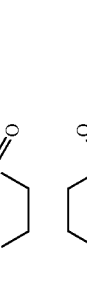 NH₂ | H | SH | H | X203 | OH | |
| 1086 | |  NMe₂ | H | SMe | H | X204 | NEt2 | |
| 1087 | |  | H | Me | H | X205 | OMe | |
| 1088 | | | H | CH=CH2 | H | X206 | Bn | |

TABLE 3-continued
| No. | G | Q | X1 | X2 | X3 | X4 | X5 | Physical constant |
|---|---|---|---|---|---|---|---|---|
| 1089 |  |  | H | ≡ | H | X207 | SH | |
| 1090 | | | Me | Ac | H | X208 | F | |
| 1091 | | | SPh | CO2Et | H | X209 | Cl | |
| 1092 | | | H | COPh | H | X210 | Br | |
| 1093 | | | H | H | Me | X211 | CN | |
| 1094 | | | H | CONH2 | H | X212 | NO2 | |
| 1095 | | | H | H | H | X213 | OH | |
| 1096 | | | H | H | H | X214 | NEt2 | |
| 1097 | | | OCF3 | H | H | X215 | OMe | |
| 1098 | | | Me | H | H | X216 | Bn | |

TABLE 3-continued
| No. | G | Q | X1 | X2 | X3 | X4 | X5 | Physical constant |
|---|---|---|---|---|---|---|---|---|
| 1099 | 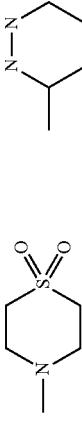 |  | NO2 | H | H | X217 | SH | |
| 1100 |  | 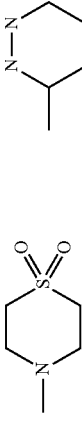 | H | H | H | X218 | SMe | |
| 1101 | 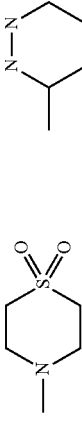 |  | H | H | H | X219 | OMe | |
| 1102 |  | 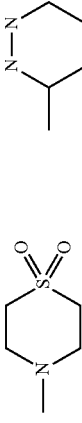 | CN | H | H | X220 | Bn | |
| 1103 | 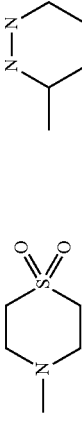 |  | H | H | H | X221 | SH | |
| 1104 |  | 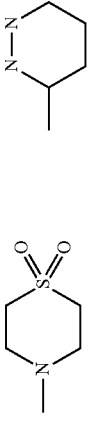 | H | H | H | X222 | SMe | |
| 1105 | 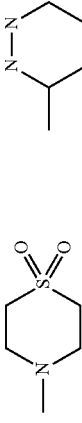 | —CN | H | H | H | X223 | Me | |
| 1106 |  | —CH=NOH | OCF3 | H | H | X224 | CH=CH2 | |
| 1107 | 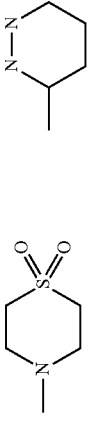 | —CH=NOCH2Ph | Me | H | H | X225 | ≡ | |
| 1108 |  | 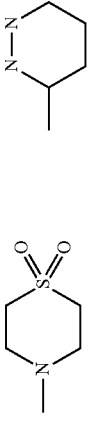 | CN | H | H | X229 | H | |

TABLE 3-continued
| No. | G | Q | X1 | X2 | X3 | X4 | X5 | Physical constant |
|---|---|---|---|---|---|---|---|---|
| 1109 |  |  | NO2 | CONEt2 | H | X230 | H | |
| 1110 |  |  | CONH2 | F | H | CO2Et | X231 | |
| 1111 |  |  | H | Cl | H | SMe | X232 | |
| 1112 |  |  | H | Br | H | Br | X233 | |
| 1113 |  |  | H | CN | H | Me | X234 | |
| 1114 | | | H | NO2 | H | Et | X235 | |
| 1115 | | | H | OH | Me | Me | X236 | |
| 1116 | | | H | NEt2 | SPh | H | X237 | |
| 1117 | | | H | OMe | H | H | X238 | |
| 1118 | | | H | Bn | H | Cl | X239 | |

TABLE 3-continued
| No. | G | Q | X1 | X2 | X3 | X4 | X5 | Physical constant |
|---|---|---|---|---|---|---|---|---|
| 1119 | 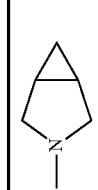 | 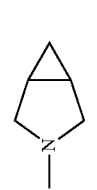 | H | SH | H | NEt2 | X240 | |
| 1120 | 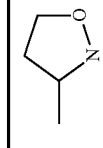 | 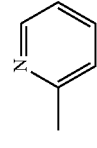 | H | SMe | H | H | X241 | |
| 1121 | 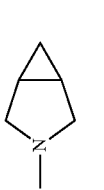 | 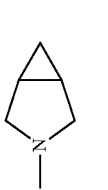 | H | Me | H | H | X242 | |
| 1122 | 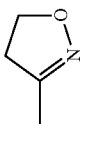 | 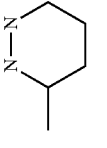 | H | CH=CH2 | OCF3 | H | X243 | |
| 1123 | 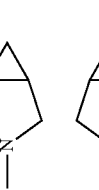 | 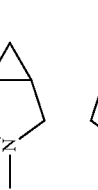 | H | C≡CH | Me | H | X244 | |
| 1124 | 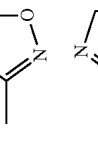 | 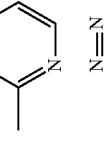 | H | Ac | NO2 | H | X245 | |
| 1125 | 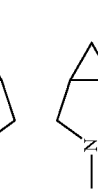 |  | H | CO2Et | H | H | X246 | |
| 1126 | 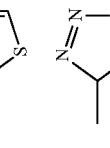 | 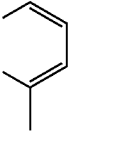 | H | COPh | H | H | X247 | |
| 1127 | 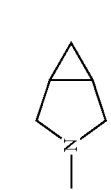 |  | H | H | CN | H | X248 | |
| 1128 | 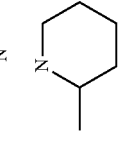 |  | CONEt2 | CONH2 | H | H | X249 | |

TABLE 3-continued

| No. | G | Q | X1 | X2 | X3 | X4 | X5 | Physical constant |
|---|---|---|---|---|---|---|---|---|
| 1129 | (cyclopropane-fused pyrrolidine) | (3-methylpiperidin-1-yl) | Me | H | CO2Et | H | X250 | |
| 1130 | (cyclopropane-fused pyrrolidine) | (3-methylpyrazin-2-yl) | NO2 | H | SMe | H | X251 | |
| 1131 | (cyclopropane-fused pyrrolidine) | (3-methylpyrazin-2-yl) | H | H | Br | H | X252 | |
| 1132 | (epoxide-fused pyrrolidine) | —CN | H | H | Me | H | X253 | |
| 1133 | (epoxide-fused pyrrolidine) | —CH=NOH | CN | H | Et | H | X254 | |
| 1134 | (epoxide-fused pyrrolidine) | —CH=NOCH₂Ph | H | Me | Me | H | X255 | |
| 1135 | (epoxide-fused pyrrolidine) | C(=O)NH₂ | Br | H | NEt2 | H | X259 | |
| 1136 | (epoxide-fused pyrrolidine) | C(=O)NMe₂ | CF3 | H | H | H | X260 | |
| 1137 | (epoxide-fused pyrrolidine) | C(=O)-pyrrolidin-1-yl | X261 | H | H | H | Cl | |
| 1138 | (epoxide-fused pyrrolidine) | C(=O)-morpholin-4-yl | X302 | OCF3 | H | H | CO2Et | |

TABLE 3-continued
| No. | G | Q | X1 | X2 | X3 | X4 | X5 | Physical constant |
|---|---|---|---|---|---|---|---|---|
| 1139 |  |  | F | H | CO2Et | N001 | H | |
| 1140 |  |  | Cl | H | SMe | N002 | H | |
| 1141 |  |  | Br | H | Br | N003 | H | |
| 1142 |  |  | CN | H | Me | N004 | H | |
| 1143 |  |  | NO2 | H | Et | N005 | H | |
| 1144 |  |  | OH | Me | Me | N006 | H | |
| 1145 |  |  | NEt2 | SPh | H | N007 | H | |
| 1146 |  |  | OMe | H | H | S001 | H | |
| 1147 |  |  | Bn | H | Cl | S002 | H | |
| 1148 |  |  | SH | H | NEt2 | S003 | H | |

TABLE 3-continued
| No. | G | Q | X1 | X2 | X3 | X4 | X5 | Physical constant |
|---|---|---|---|---|---|---|---|---|
| 1149 |  |  | SMe | H | H | S004 | H | |
| 1150 |  |  | Me | H | H | S005 | H | |
| 1151 |  |  | CH=CH2 | OCF3 | H | S006 | H | |
| 1152 |  |  | ≡ | Me | H | S007 | H | |
| 1153 |  |  | Ac | NO2 | H | S008 | H | |
| 1154 |  |  | CO2Et | H | H | S009 | H | |
| 1155 |  |  | COPh | H | H | H001 | H | |
| 1156 |  |  | H | CN | H | H002 | H | |
| 1157 |  |  | CONH2 | H | H | H003 | H | |
| 1158 |  |  | T001 | CF3 | H | Br | H | |

TABLE 3-continued
| No. | G | Q | X1 | X2 | X3 | X4 | X5 | Physical constant |
|---|---|---|---|---|---|---|---|---|
| 1159 | 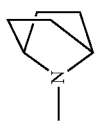 | —CN | T002 | OiPr | H | H | H | |
| 1160 | 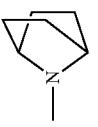 | —CH=NOH | T003 | OCONH | H | H | H | |
| 1161 | 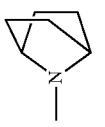 | —CH=NOCH₂Ph | T004 | | H | H | H | |
| 1162 | 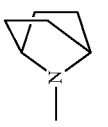 | ⟩—NH₂ (C=O) | T008 | Bn | H | H | H | |
| 1163 | 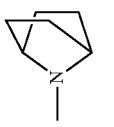 | ⟩—NMe₂ (C=O) | T009 | Cl | H | H | H | |
| 1164 | 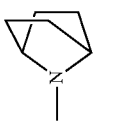 | pyrrolidine-C(=O) | Me | F | F | H | CO2Et | |
| 1165 | 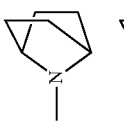 | morpholine-C(=O) | F | T010 | Cl | H | SMe | |
| 1166 | 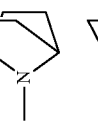 | ⟩—NH₂ (C=S) | Cl | T011 | Br | H | Br | |
| 1167 | 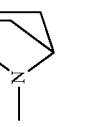 | ⟩—NMe₂ (C=S) | Br | T012 | CN | H | Me | |

TABLE 3-continued

| No. | G | Q | X1 | X2 | X3 | X4 | X5 | Physical constant |
|---|---|---|---|---|---|---|---|---|
| 1168 | | | CN | T014 | NO2 | H | Et | |
| 1169 | | | H | T015 | OH | Me | Me | |
| 1170 | | | Me | T016 | NEt2 | SPh | H | |
| 1171 | | | F | T017 | OMe | H | H | |
| 1172 | | | CF3 | T018 | Bn | H | Cl | |
| 1173 | | | CO2Me | T019 | SH | H | NEt2 | |
| 1174 | | | F | H004 | SMe | H | H | |
| 1175 | | | Cl | H005 | Me | H | H | |
| 1176 | | | H | H006 | CH=CH2 | OCF3 | H | |

TABLE 3-continued
| No. | G | Q | X1 | X2 | X3 | X4 | X5 | Physical constant |
|---|---|---|---|---|---|---|---|---|
| 1177 |  | 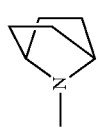 | H | H007 | ≡ | Me | H | |
| 1178 |  |  | H | X101 | Ac | NO2 | H | |
| 1179 | 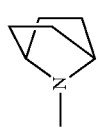 |  | CO2Et | X102 | CO2Et | H | H | |
| 1180 | 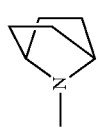 |  | Et | X103 | COPh | H | H | |
| 1181 | 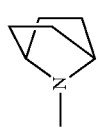 |  | iPr | X104 | H | CN | H | |
| 1182 | 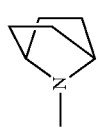 |  | Me | X105 | CONH2 | H | H | |
| 1183 | 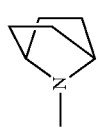 |  | Bn | X106 | Cl | Me | Bn | |
| 1184 | 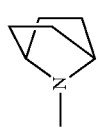 |  | SH | X107 | NEt2 | F | NEt2 | |
| 1185 | 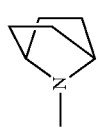 |  | SMe | X108 | H | Cl | OH | |

TABLE 3-continued
| No. | G | Q | X1 | X2 | X3 | X4 | X5 | Physical constant |
|---|---|---|---|---|---|---|---|---|
| 1186 |  | —CN | Me | X109 | H | Br | Br | |
| 1187 |  | —CH=NOH | CH=CH2 | X110 | H | CN | Cl | |
| 1188 |  | —CH=NOCH₂Ph | ≡ | X111 | H | H | F | |
| 1189 |  | —C(=O)NH₂ | H | X115 | H | CO2Me | CH=CH2 | |
| 1190 |  | —C(=O)NMe₂ | CONH2 | X116 | H | F | ≡ | |
| 1191 |  | pyrrolidinyl-C(=O)— | H | Ac | X117 | Cl | H | |
| 1192 |  | morpholinyl-C(=O)— | H | CO2Et | X118 | H | H | |
| 1193 |  | —C(=S)NH₂ | Cl | COPh | X119 | H | H | |
| 1194 |  | —C(=S)NMe₂ | NEt2 | H | X120 | H | H | |

TABLE 3-continued

| No. | G | Q | X1 | X2 | X3 | X4 | X5 | Physical constant |
|---|---|---|---|---|---|---|---|---|
| 1195 | (bicyclic N) | pyrrolidine-C(=S)- | H | CONH2 | X121 | CO2Et | H | |
| 1196 | (bicyclic N) | morpholine-C(=S)- | pyrazine-OMe | H | X122 | Et | H | |
| 1197 | (bicyclic N) | azetidine | H | pyrazine-SMe | X123 | iPr | H | |
| 1198 | (bicyclic N) | pyrrolidine | H | H | X124 | Me | H | |
| 1199 | (bicyclic N) | pyrrole | H | CH=CH-SMe | X125 | Me | Me | |
| 1200 | (bicyclic N) | isoxazolidine | H | H | X126 | F | F | |
| 1201 | (bicyclic N) | isoxazoline | H | H | X127 | CF3 | Cl | |

TABLE 3-continued

| No. | G | Q | X1 | X2 | X3 | X4 | X5 | Physical constant |
|-----|---|---|-----|-----|-----|-----|-----|-------------------|
| 1202 | bicyclic N-ring | 3-methylisoxazole | H | H | X128 | CO2Me | Br | |
| 1203 | bicyclic N-ring | 2-methylthiazole | H | H | X129 | F | CN | |
| 1204 | bicyclic N-ring | 5-methyltetrazole | OPh | H | X130 | Cl | H | |
| 1205 | bicyclic N-ring | 2-methylpiperidine | Pyridin-2-yl | H | X131 | H | Me | |
| 1206 | bicyclic N-ring | 2-methylpyridine | methoxyethynyl | H | X132 | H | F | |
| 1207 | bicyclic N-ring | 3-methyltetrahydropyridazine | methoxyvinyl | H | X133 | H | CF3 | |
| 1208 | bicyclic N-ring | 2-methylpyrimidine | methylthioethynyl | H | X134 | CO2Et | CO2Me | |

TABLE 3-continued

| No. | G | Q | X1 | X2 | X3 | X4 | X5 | Physical constant |
|---|---|---|---|---|---|---|---|---|
| 1209 | (bicyclic N-heterocycle) | (methylpyridazine) | (methoxypyrazine) | H | X135 | Et | H | |
| 1210 | (bicyclic N-heterocycle) | (methylpiperazine) | H | H | X136 | iPr | H | |
| 1211 | (bicyclic N-heterocycle) | (methylpyrazine) | H | H | X137 | Me | SPh | |
| 1212 | (bicyclic N-heterocycle) | (methylpyrimidine) | H | H | X138 | Me | SOPh | |
| 1213 | (bicyclic N-heterocycle) | —CN | H | H | X139 | F | SO2Ph | |
| 1214 | (bicyclic N-heterocycle) | —CH=NOH | H | H | X140 | CF3 | SOMe | |
| 1215 | (bicyclic N-heterocycle) | —CH=NOCH$_2$Ph | H | H | X141 | CO2Me | SO2Et | |
| 1216 | (bicyclic N-heterocycle) | —C(=O)NH$_2$ | H | CN | X145 | H | H | |
| 1217 | (bicyclic N-heterocycle) | —C(=O)NMe$_2$ | H | NO2 | X146 | H | H | |

TABLE 3-continued
| No. | G | Q | X1 | X2 | X3 | X4 | X5 | Physical constant |
|---|---|---|---|---|---|---|---|---|
| 1218 | 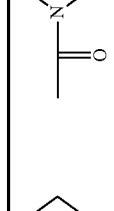 | 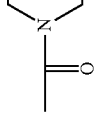 | H | OH | X147 | H | F | |
| 1219 |  |  | H | NEt2 | X148 | H | Cl | |
| 1220 | 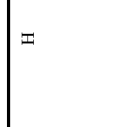 |  | H | OMe | H | X201 | Br | |
| 1221 |  |  | H | Bn | H | X202 | CN | |
| 1222 |  |  | H | SH | H | X203 | OH | |
| 1223 |  |  | H | SMe | H | X204 | NEt2 | |
| 1224 |  |  | H | Me | H | X205 | OMe | |
| 1225 | 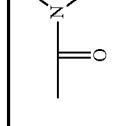 | 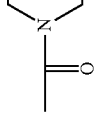 | H | CH=CH2 | H | X206 | Bn | |
| 1226 |  |  | H | ≡ | H | X207 | SH | |
| 1227 |  |  | Me | Ac | H | X208 | F | |

TABLE 3-continued

| No. | G | Q | X1 | X2 | X3 | X4 | X5 | Physical constant |
|---|---|---|---|---|---|---|---|---|
| 1228 | | | SPh | CO2Et | H | X209 | Cl | |
| 1229 | | | H | COPh | H | X210 | Br | |
| 1230 | | | H | H | Me | X211 | CN | |
| 1231 | | | H | CONH2 | H | X212 | NO2 | |
| 1232 | | | SMe | H | H | X213 | OH | |
| 1233 | | | H | SH | H | X214 | NEt2 | |
| 1234 | | | OCF3 | H | H | X215 | OMe | |
| 1235 | | | Me | H | H | X216 | Bn | |
| 1236 | | | NO2 | H | H | X217 | SH | |
| 1237 | | | H | H | CSPh | X218 | SMe | |

TABLE 3-continued
| No. | G | Q | X1 | X2 | X3 | X4 | X5 | Physical constant |
|---|---|---|---|---|---|---|---|---|
| 1238 | 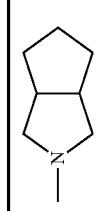 | 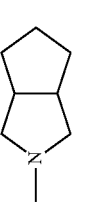 | H | 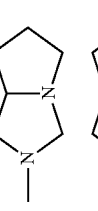 | H | X219 | OMe | |
| 1239 | 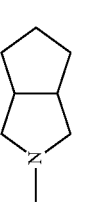 | 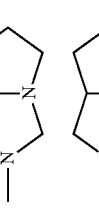 | CN | H | H | X220 | Bn | |
| 1240 | 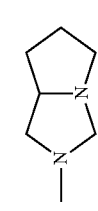 | —CN | H | H | CSCH=CH2 | X221 | SH | |
| 1241 | 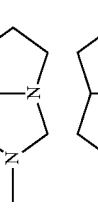 | —CH=NOH | COPh | H | H | X222 | SMe | |
| 1242 | 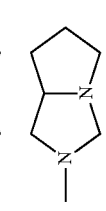 | —CH=NOCH2Ph | H | CSMe | H | X223 | Me | |
| 1243 | 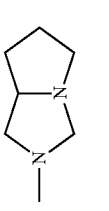 | 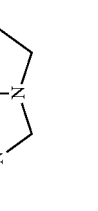 | H | H | H | X227 | CO2Et | |
| 1244 |  | 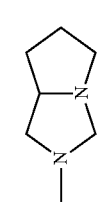 | H | H | H | X228 | COPh | |
| 1245 | 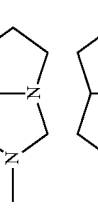 | 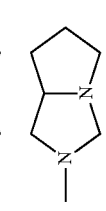 | CN | CONEt2 | H | X229 | H | |
| 1246 | 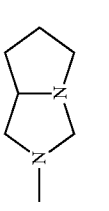 |  | NO2 | F | H | X230 | H | |
| 1247 |  | 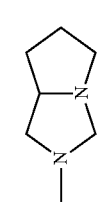 | CONH2 | H | H | CO2Et | X231 | |

TABLE 3-continued

| No. | G | Q | X1 | X2 | X3 | X4 | X5 | Physical constant |
|---|---|---|---|---|---|---|---|---|
| 1248 | [bicyclic N] | C(=S)NMe2 | H | Cl | H | SMe | X232 | |
| 1249 | [bicyclic N] | C(=S)-pyrrolidinyl | H | Br | H | Br | X233 | |
| 1250 | [bicyclic N] | C(=S)-morpholinyl | H | CN | H | Me | X234 | |
| 1251 | [bicyclic N] | azetidinyl | H | NO2 | H | Et | X235 | |
| 1252 | [bicyclic N] | pyrrolidinyl | H | OH | Me | Me | X236 | |
| 1253 | [bicyclic N] | pyrrolyl | H | NEt2 | SPh | H | X237 | |
| 1254 | [bicyclic N] | isoxazolidinyl | H | OMe | H | H | X238 | |
| 1255 | [bicyclic N] | isoxazolinyl | H | Bn | H | Cl | X239 | |
| 1256 | [bicyclic N] | isoxazolyl | H | SH | H | NEt2 | X240 | |
| 1257 | [bicyclic N] | thiazolyl | H | SMe | H | H | X241 | |

TABLE 3-continued
| No. | G | Q | X1 | X2 | X3 | X4 | X5 | Physical constant |
|---|---|---|---|---|---|---|---|---|
| 1258 |  | 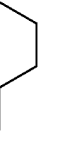 | COCH=CH2 | Me | H | H | X242 | |
| 1259 |  | 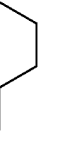 | H | CH=CH2 | OCF3 | H | X243 | |
| 1260 |  | 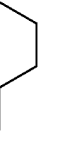 | H | ≡ | Me | H | X244 | |
| 1261 |  |  | H | Ac | NO2 | H | X245 | |
| 1262 |  | 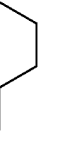 | H | CO2Et | H | H | X246 | |
| 1263 |  | 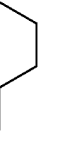 | H | COPh | H | H | X247 | |
| 1264 |  | 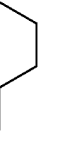 | H | 4-Cl—Ph | CN | H | X248 | |
| 1265 |  | 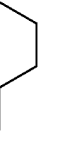 | CONEt2 | Et | H | H | X249 | |
| 1266 |  | 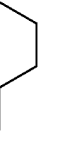 | Me | H | CO2Et | H | X250 | |

In Table 3, compounds with compound numbers 229 and 230 are cis-trans isomers based on the configuration of the 3,5-dimethyl group in the 3,5-dimethyl-piperidine-1-yl group of G in the aforementioned formula (1), and compounds with compound numbers 267 and 268 are cis-trans isomers based on the configuration of the 3,4-difluoro group in the 3,4-difluoropyrrolidine-1-yl group. Moreover, $^1$H-NMR. data on several compounds in Table 3 are shown in Table 4 below. Note that compound numbers in Table 4 correspond to those in Table 3.

TABLE 4

| Compound No. | |
|---|---|
| 12 | $^1$H-NMR (CDCl$_3$, δ ppm): 1.79 (s, 6H), 2.04-2.09 (m, 4H), 2.90-3.15 (m, 6H), 3.61 (br s, 2H), 3.80 (br s, 2H), 7.52 (d, 1H), 7.78 (d, 1H) |
| 40 | $^1$H-NMR (CDCl$_3$, δ ppm): 1.96-2.12 (m, 4H), 2.89 (s, 3H), 3.12 (s, 3H), 3.58 (br s, 2H), 3.76 (br s, 2H), 6.90 (d, 1H), 7.18 (s, 1H) |
| 46 | $^1$H-NMR (CDCl$_3$, δ ppm): 1.36 (s, 9H), 2.02-2.08 (m, 4H), 2.22 (s, 1H), 3.60 (br s, 2H), 3.76 (br s, 2H), 4.04 (d, 1H), 4.71 (d, 1H), 7.00 (d,1H), 7.21 (d, 1H) |
| 57 | $^1$H-NMR (CDCl$_3$, δ ppm): 1.57 (s, 6H), 2.02-2.08 (m, 4H), 3.60 (br s, 2H), 3.71 (br s, 2H), 6.72 (d, 1H), 7.13 (d, 1H) |
| 71 | $^1$H-NMR (CDCl$_3$, δ ppm): 1.24 (t, 3H), 2.02-2.08 (m, 4H), 3.60 (bs, 2H), 3.78 (bs, 2H), 4.22 (q, 2H), 6.14 (s, 1H), 7.25 (d, 1H), 7.41 (m, 3H), 7.57 (d, 2H), 7.70 (d, 1H) |
| 72 | $^1$H-NMR (CDCl$_3$, δ ppm): 1.73 (s, 6H), 2.03-2.08 (m, 4H), 3.60 (br s, 2H), 3.80 (br s, 2H), 7.23 (d, 1H), 7.57 (d, 1H) |
| 78 | $^1$H-NMR (CDCl$_3$, δ ppm): 1.82(s, 6H), 2.04-2.09 (m, 4H), 3.60 (br s, 2H), 3.78 (br s, 2H), 5.49 (br s, 1H), 6.35 (br s, 1H), 7.23 (d, 1H), 7.50 (d, 1H) |
| 80 | $^1$H-NMR (CDCl$_3$, δ ppm): 1.16 (t, 3H), 1.80 (s, 6H), 2.05-2.09 (m, 4H), 3.34 (dq, 2H), 3.60 (bs, 1H), 3.78 (bs, 1H), 6.48 (bt, 1H), 7.23 (d, 1H), 7.49 (d, 1H) |
| 86 | $^1$H-NMR (CDCl$_3$, δ ppm): 1.83 (s, 6H), 2.04-2.08 (m, 4H), 3.59 (br s, 2H), 3.74 (br s, 2H), 4.49 (d, 2H), 6.78 (br t, 1H), 7.18 (d, 1H), 7.26-7.36 (m, 5H), 7.47 (d, 1H) |
| 88 | $^1$H-NMR (CDCl$_3$, δ ppm): 1.91 (s, 6H), 2.05-20.9 (m, 4H), 3.60 (bs, 2H), 3.78 (bs, 2H), 6.65 (s, 1H), 7.23-7.37 (m, 5H), 7.52-7.60 (m, 2H) |
| 89 | $^1$H-NMR (CDCl$_3$, δ ppm): 1.80 (s, 1H), 2.02-2.08 (m, 4H), 3.58 (bs, 2H), 3.74 (bs, 2H), 7.19 (d, 1H), 7.61-7.69 (m, 3H), 7.90 (t, 1H), 8.63 (d, 2H) |
| 90 | $^1$H-NMR (CDCl$_3$, δ ppm): 1.83 (s, 6H), 2.05-2.10 (m, 4H), 3.60 (br s, 2H), 3.73-3.80 (m, 5H), 7.24 (d, 1H), 7.49 (d, 1H), 9.03 (s, 1H) |
| 92 | $^1$H-NMR (CDCl$_3$, δ ppm): 1.73 (s, 6H), 2.05-2.10 (m, 4H), 2.96-3.09 (m, 6H), 3.60 (br s, 2H), 3.78 (br s, 2H), 7.24 (d, 1H), 7.55 (d, 1H) |
| 97 | $^1$H-NMR (CDCl$_3$, δ ppm): 1.74 (s, 6H), 2.05-2.09 (m, 4H), 3.18 (s, 3H), 3.60 (bs, 2H), 3.79 (bs, 2H), 4.36 (s, 2H), 7.25 (d, 1H), 7.55 (d, 1H) |
| 109 | $^1$H-NMR (CDCl$_3$, δ ppm): 1.30 (t, 3H), 1.73 (s, 6H), 2.07(m, 4H), 3.60 (br, 2H), 3.77 (br, 2H), 4.24 (q, 2H), 7.21 (d, 1H), 7.51 (d, 1H), 7.62 (br, 1H), 7.86 (br, 1H) |
| 110 | $^1$H-NMR (CDCl$_3$, δ ppm): 1.37-1.48 (m, 2H), 1.67-1.78 (m, 2H), 1.96-2.11 (m, 4H), 3.59 (br s, 2H), 3.77 (br s, 2H), 4.26 (br s, 1H) 7.23 (d, 1H), 7.61 (d, 1H) |
| 115 | $^1$H-NMR (CDCl$_3$, δ ppm): 1.97 (s, 3H), 2.07 (m, 4H), 3.67 (br, 2H), 3.79 (br, 2H), 7.26 (d, 1H), 7.62 (d, 1H) |
| 116 | $^1$H-NMR (CDCl$_3$, δ ppm): 1.14 (t, 3H), 1.98 (s, 3H), 2.08 (m, 4H), 3.36 (m, 2H), 3.61 (br S, 2H), 3.79 (br s, 2H), 6.04 (br s, 1H), 7.26 (d, 1H), 7.57 (d, 1H) |
| 117 | $^1$H-NMR (CDCl$_3$, δ ppm): 1.99 (s, 3H), 2.08 (m, 4H), 3.05 (br, 6H), 3.61 (br, 2H), 3.79 (br, 2H), 7.28 (d, 1H), 7.60 (d, 1H) |
| 118 | $^1$H-NMR (CDCl$_3$, δ ppm): 1.04 (t, 3H), 1.72 (s, 3H), 1.93-2.22 (m, 6H), 3.60 (br s, 2H), 3.77 (br s, 2H), 5.30 (br s, 1H), 7.22 (d, 1H), 7.56 (d, 1H) |
| 122 | $^1$H-NMR (CDCl$_3$, δ ppm): 0.96 (t, 6H), 1.96-2.33 (m, 8H), 3.60 (br s, 2H), 3.77 (br s, 2H), 5.41 (br s, 1H), 7.22 (d, 1H), 7.58 (d, 1H) |
| 144 | $^1$H-NMR (CDCl$_3$, δ ppm): 2.05 (br, 4H), 2.59 (s, 1H), 3.52 (br, 2H), 3.78 (br, 2H), 4.80 (s, 2H), 7.32 (d, 1H) |

TABLE 4-continued

| Compound No. | |
|---|---|
| 168 | 1H-NMR (CDCl3, δ ppm): 1.52 (s, 6H), 2.05 (m, 4H), 2.96 (s, 2H), 3.58 (br, 2H), 3.72 (br, 2H), 6.94 (d, 1H) |
| 184 | $^1$H-NMR (CDCl$_3$, δ ppm): 2.05-2.09 (m, 4H), 2.56 (t, 1H), 3.60-3.75 (m, 4H), 4.75 (d, 2H), 6.69 (s, 1H), 7.42 (s, 1H) |
| 187 | $^1$H-NMR (CDCl$_3$, δ ppm): 2.02-2.07 (m, 8H), 3.62 (br s, 4H), 3.72 (br s, 4H), 6.57 (s, 1H), 7.45 (s, 1H) |
| 188 | $^1$H-NMR (CDCl$_3$, δ ppm): 1.81-1.87 (m, 4H), 2.03-2.09 (m, 4H). 3.36-3.42 (m, 4H), 3.57 (br s, 2H), 3.80 (br s, 2H), 3.81-3.85 (m, 2H), 4.90-4.92 (m, 1H), 5.20-5.32 (m, 2H), 6.85-5.98 (m, 1H), 6.60 (s, 1H), 7.49 (s, 1H) |
| 192 | $^1$H-NMR (CDCl$_3$, δ ppm): 1.88-1.93 (m, 4H), 3.54 (br s, 4H), 5.10 (s, 2H), 6.50 (d, 1H), 6.95 (d, 1H), 7.24-7.39 (m, 5H), 7.60 (s, 1H) |
| 199 | $^1$H-NMR (CDCl$_3$, δ ppm): 2.00 (br m, 4H), 2.52 (t, 1H), 2.79 (s, 3H), 2.85 (s, 3H), 3.10-3.30 (br m, 1H), 3.50-3.80 (br m, 3H), 4.66 (d, 2H), 6.70 (d, 1H), 7.04 (d, 1H) |
| 201 | $^1$H-NMR (CDCl$_3$, δ ppm): 1.24 (t, 3H), 1.64 (s, 6H), 1.97 (br s, 4H), 2.17 (s, 3H), 3.20-3.73 (br m, 4H), 4.20(q, 2H), 7.05 (d, 1H), 7.26 (d, 1H), 9.62 (br s, 1H) |
| 204 | $^1$H-NMR (CDCl$_3$, δ ppm): 1.24 (t, 3H), 1.66 (s, 6H), 1.75-2.25 (br m, 4H), 3.07 (s, 3H), 3.07-3.85 (br m, 4H), 4.17 (q, 2H), 4.34 (d, 1H), 5.72 (d, 1H), 6.88 (dd, 2H), 6.94 (d, 1H), 7.24 (m, 3H), 7.80 (d, 1H) |
| 205 | $^1$H-NMR (CDCl$_3$, δ ppm): 1.80-2.05 (br m, 8H), 2.52 (t, 1H), 3-3.8 (br m, 8H), 4.67 (d, 2H), 7.00 (d, 1H), 7.03 (d, 1H) |
| 208 | $^1$H-NMR (CDCl$_3$, δ ppm): 1.70-2.05 (m, 4H), 2.35 (d, 3H), 2.50 (t, 1H), 3.37 (br s, 2H), 3.68 (br s, 2H), 4.58 (d, 2H), 5.71 (s, 1H), 6.48 (d, 1H), 6.94 (d, 1H) |
| 209 | $^1$H-NMR (CDCl$_3$, δ ppm): 1.92-2.03 (m, 4H), 2.47 (t, 1H), 3.56 (br s, 4H), 4.53 (d, 2H), 6.44 (d, 1H), 6.93 (d, 1H), 7.38 (d, 1H), 7.82 (d, 1H) |
| 210 | $^1$H-NMR (CDCl$_3$, δ ppm): 1.90-2.07 (br m, 4H), 2.45 (t, 1H), 3.23, 3.74 (br s, 4H), 4.48 (d, 2H), 6.38 (d, 1H), 6.87 (d, 1H), 7.08 (d, 1H), 7.20 (m, 1H), 7.54 (t, 1H), 8.61 (m, 1H) |
| 252 | $^1$H-NMR (CDCl$_3$, δ ppm): 1.60 (s, 9H), 3.73-3.84 (m, 8H), 7.30 (d, 1H), 7.42 (d, 1H) |
| 258 | $^1$H-NMR (CDCl$_3$, δ ppm): 1.16 (t, 3H), 1.80 (s, 6H), 3.35 (m, 2H), 4.18 (br m, 4H), 6.39 (br s, 1H), 7.28 (d, 1H), 7.51 (d, 1H) |
| 264 | $^1$H-NMR (CDCl$_3$, δ ppm): 1.16 (t, 3H), 1.80 (s, 6H), 3.34 (dq, 2H), 3.70-3.83 (m, 8H), 6.47 (bt, 1H), 7.24 (d, 1H), 7.48 (d, 1H) |
| 267 | $^1$H-NMR (CDCl$_3$, δ ppm): 2.57 (t, 1H), 4.08 (br m, 4H), 4.74 (d, 2H), 5.20-5.40 (m, 2H), 6.74 (d, 1H), 7.19 (d, 1H) |
| 268 | $^1$H-NMR (CDCl$_3$, δ ppm): 2.57 (t, 1H), 4.01 (br m, 4H), 4.73 (d, 2H), 5.15-5.37 (m, 2H), 6.72 (d, 1H), 7.19 (d, 1H) |
| 284 | $^1$H-NMR (CDCl$_3$, δ ppm): 2.05 (m, 4H), 3.58 (br, 2H), 3.77 (br, 2H), 3.81 (s, 3H), 6.79 (br, 1H), 7.22 (d, 1H), 7.40 (d, 1H), 7.94 (br, 1H) |
| 285 | $^1$H-NMR (CDCl$_3$, δ ppm): 2.08 (m, 4H), 3.60 (br, 2H), 3.79 (br, 2H), 7.30 (d, 1H), 7.46 (d, 1H), 8.99 (br, 1H) |
| 292 | $^1$H-NMR (CDCl$_3$, δ ppm): 2.07 (m, 4H), 3.15 (s, 6H), 3.60 (br, 2H), 3.78 (br, 2H), 7.30 (d, 1H), 7.79 (d, 1H) |
| 296 | $^1$H-NMR (CDCl$_3$, δ ppm): 2.51 (tt, 1H), 4.28 (t, 4H), 6.86 (d, 1H), 7.19 (dd, 1H), 7.41 (d, 1H) |
| 302 | $^1$H-NMR (CDCl$_3$, δ ppm): 2.26 (t, 1H), 3.96 (d, 2H), 4.12 (m, 4H), 4.42 (br s, 1H), 6.36 (d, 1H), 7.13 (d, 1H) |
| 303 | $^1$H-NMR (CDCl$_3$, δ ppm): 2.04 (m, 4H), 3.58 (br, 2H), 3.76 (br, 2H), 3.82 (s, 3H), 4.06 (m, 2H), 4.85 (m, 1H), 7.21 (d, 1H), 7.30 (br, 1H), 7.42 (d, 1H) |
| 306 | $^1$H-NMR (CDCl3, δ ppm): 2.06 (m, 4H), 2.31 (t, 1H), 3.58 (br, 2H), 3.76 (br, 2H), 4.08 (m, 2H), 4.91 (m, 1H), 5.26 (s, 2H), 7.20 (d, 1H), 7.32 (m, 5H), 7.40 (d, 1H) |
| 311 | $^1$H-NMR (CDCl$_3$, δ ppm): 2.05 (m, 4H), 3.57 (m, 2H), 3.75 (br, 2H), 4.61 (m, 2H), 4.99 (dd, 1H), 5.25 (s, 2H), 7.22 (d, 1H), 7.35 (m, 5H), 7.51 (d, 1H) |
| 314 | $^1$H-NMR (CDCl$_3$, δ ppm): 1.28 (t, 3H), 2.04 (m, 4H), 3.59 (br, 2H), 3.76 (br, 2H), 4.30 (q, 2H), 7.15 (d, 1H), 7.29 (d, 1H), 7.97 (s, 1H) |
| 318 | $^1$H-NMR (CDCl$_3$, δ ppm): 2.06 (m, 4H), 3.58 (br, 2H), 3.76 (br, 2H), 5.40 (s, 2H), 7.27 (d, 1H), 7.38 (m, 5H), 7.73 (d, 1H), 8.33 (s, 1H) |
| 321 | $^1$H-NMR (CDCl$_3$, δ ppm): 1.25 (t, 3H), 2.03 (m, 4H), 3.49 (m, 3H), 3.58 (br, 2H), 3.75 (br, 2H), 4.12 (q, 2H), 6.18 (br, 1H), 7.17 (d, 1H), 7.33 (d, 1H) |

TABLE 4-continued

| Compound No. | |
|---|---|
| 325 | $^1$H-NMR (CDCl$_3$, δ ppm): 2.12-2.22 (m, 2H), 2.56 (t, 1H), 3.63 (br t, 2H), 3.87 (br s, 2H), 4.74 (d, 2H), 6.54 (d, 1H), 7.05 (m, 3H), 7.15 (d, 1H), 7.33 (m, 2H) |
| 326 | $^1$H-NMR (CDCl$_3$, δ ppm): 2.53 (t, 1H), 2.82 (t, 2H), 4.10 (t, 2H), 4.69 (t, 2H), 6.68 (d, 1H), 7.01-7.42 (m, 6H) |
| 334 | $^1$H-NMR (CDCl$_3$, δ ppm): 1.25 (m, 3H), 3.50 (m, 2H), 4.15 (br s, 4H), 6.22 (br s, 1H), 7.22 (d, 1H), 7.38 (d, 1H) |
| 336 | $^1$H-NMR (CDCl$_3$, δ ppm): 1.47 (t, 3H), 4.16 (br, 4H), 4.54 (q, 2H), 7.36 (d, 1H), 7.53 (d, 1H) |
| 337 | $^1$H-NMR (CDCl$_3$, δ ppm): 3.15 (s, 6H), 4.18 (br, 4H), 7.36 (d, 1H), 7.52 (d, 1H) |
| 339 | $^1$H-NMR (CDCl$_3$, δ ppm): 4.08 (br m, 4H), 5.07 (s, 2H), 6.41 (d, 1H), 6.93-7.15 (m, 4H), 7.25-7.32 (m, 6H) |
| 398 | $^1$H-NMR (CDCl$_3$): δ 0.90 (t, 3H), 1.68 (m, 2H), 2.06 (m, 4H), 2.52 (t, 2H), 3.77 (br, 2H), 3.85 (br, 2H), 6.99 (d, 1H), 7.27 (d, 1H), 7.89 (s, 1H) |
| 406 | $^1$H-NMR (CDCl$_3$): δ 1.99 (s, 6H), 2.07 (m, 4H), 3.59 (br, 2H), 3.77 (br, 2H), 7.22 (d, 1H), 7.54 (d, 1H), 8.36 (s, 1H) |
| 408 | $^1$H-NMR (CDCl$_3$): δ 1.91 (s, 6H), 2.06 (m, 4H), 3.59 (br, 2H), 3.77 (br, 2H), 7.21 (d, 1H), 7.24-7.46 (m, 5H), 7.53 (d, 1H) |
| 415 | $^1$H-NMR (CDCl$_3$): δ 1.72 (d, 3H), 2.03 (m, 4H), 3.54 (br, 2H), 3.72 (br, 2H), 5.29 (s, 2H), 5.52 (q, 1H), 6.62 (d, 1H), 6.79 (s, 1H), 6.99-7.02 (m, 3H), 7.10 (d, 1H), 7.26-29 (m, 3H) |
| 417 | $^1$H-NMR (CDCl$_3$): δ 1.75 (s, 6H), 2.08 (m, 4H), 3.16 (s, 3H), 3.60 (br, 2H), 3.78 (br, 2H), 4.05 (q, 2H), 7.24 (d, 1H), 7.55 (d, 1H) |
| 423 | $^1$H-NMR (CDCl$_3$): δ 1.91 (s, 6H), 2.07 (m, 4H), 2.40 (s, 3H), 3.59 (br, 2H), 3.77 (br, 2H), 6.02 (s, 1H), 7.21 (d, 1H), 7.51 (d, 1H) |
| 429 | $^1$H-NMR (CDCl$_3$): δ 1.47 (d, 3H), 1.60 (m, 3H), 2.06 (m, 4H), 3.60 (br, 2H), 3.75 (br, 2H), 5.07 (m, 1H), 6.52 (d, 1H), 7.14 (d, 1H) |
| 430 | $^1$H-NMR (CDCl$_3$): δ 1,18 (t, 3H), 2.57 (t, 1H), 3.34 (q, 1H), 3.66-3.85 (br, 2H), 4.09-4.28 (br, 5H), 4.73 (d, 2H), 6.74 (d, 1H), 7.18 (d, 1H), 7.29 (m, 5H) |
| 432 | $^1$H-NMR (CDCl$_3$): δ 1.92 (s, 6H), 2.06 (m, 4H), 3.59 (br, 2H), 3.76 (br, 2H), 7.19 (d, 1H), 7.52 (d, 1H), 7.70 (s, 1H), 7.83 (s, 1H) |
| 434 | $^1$H-NMR (CDCl$_3$): δ 1.92 (s, 6H), 2.07 (m, 4H), 2.29 (s, 3H), 3.60 (br, 2H), 3.77 (br, 2H), 6.09 (s, 1H), 7.21 (d, 1H), 7.52 (d, 1H) |
| 436 | $^1$H-NMR (CDCl$_3$): δ 2.08-2.43 (m, 4H), 2.56 (t, 1H), 3.76 (s, 3H), 3.60-3.95 (m, 2H), 4.54 (br, 1H), 4.72 (d, 2H), 6.68 (d, 1H), 7.15 (d, 1H) |
| 437 | $^1$H-NMR (CDCl$_3$): δ 1.79 (s, 6H), 2.07 (m, 4H), 3.37 (s, 6H), 3.44 (d, 2H), 3.60 (br, 2H), 3.78 (br, 2H), 4.39 (t, 1H), 6.59 (br, 1H), 7.23 (d, 1H), 7.52 (d, 1H) |
| 440 | $^1$H-NMR (CDCl$_3$): δ 0.37 (m, 2H), 0.63 (m, 2H), 1.28 (m, 1H), 2.05 (m, 4H), 3.58 (br, 2H), 3.74 (br, 2H), 3.84 (d, 2H), 6.56 (d, 1H), 7.15 (d, 1H) |
| 442 | $^1$H-NMR (CDCl$_3$): δ 1.74 (s, 6H), 2.03 (m, 4H), 2.31 (s, 3H), 3.54 (br, 2H), 3.71 (br, 2H), 6.10 (s, 1H), 6.28 (d, 1H), 7.13 (d, 1H) |
| 443 | $^1$H-NMR (CDCl$_3$): δ 1.88 (s, 6H), 2.07 (m, 4H), 3.60 (br, 2H), 3.78 (br, 2H), 7.23 (d, 1H), 7.31 (d, 2H), 7.52 (d, 1H), 8.58 (d, 2H) |
| 451 | $^1$H-NMR (CDCl$_3$): δ 2.03 (m, 6H), 2.07 (m, 4H), 3.60 (br, 2H), 3.78 (br, 2H), 7,23 (d, 1H), 7.45 (dd, 1H), 7.56 (d, 1H), 7.64 (dd, 1H), 9.10 (dd, 1H) |
| 455 | $^1$H-NMR (CDCl$_3$): δ 1.90 (s, 6H), 2.06 (m, 4H), 3.59 (br, 2H), 3.77 (br, 2H), 7.09 (s, 1H), 7.20 (d, 1H), 7.47 (d, 1H), 7.82 (s, 1H) |

[Herbicide]

Although a few examples regarding herbicides of the present invention are shown next, active-ingredient compounds, additives, and proportions added are changeable over a wide range without being limited solely to the present examples. Parts in Examples of formulations show parts by weight.

FORMULATION EXAMPLE 1

Wettable Powder

| | |
|---|---|
| Compound of the present invention | 20 parts |
| White carbon | 20 parts |
| Diatomaceous earth | 52 parts |
| Sodium alkyl sulfate | 8 parts |

The above components were mixed homogenously and ground finely to obtain a wettable powder with 20% of active ingredient.

FORMULATION EXAMPLE 2

Emulsion

| | |
|---|---|
| Compound of the present invention | 5 parts |
| Dimethylformamide | 94 parts |
| polyoxyethylene-sorbitan type surfactant | 1 part |

The above components were mixed and dissolved to obtain an emulsion with 5% of active ingredient.

FORMULATION EXAMPLE 3

Emulsion

| | |
|---|---|
| Compound of the present invention | 20 parts |
| Xylene | 55 parts |
| Dimethylformamide | 15 parts |
| Polyoxyethylene phenyl ether | 10 parts |

The above components were mixed and dissolved to obtain an emulsion with 20% of active ingredient.

FORMULATION EXAMPLE 4

Granules

| | |
|---|---|
| Compound of the present invention | 5 parts |
| Talc | 40 parts |
| Clay | 38 parts |
| Bentonite | 10 parts |
| Sodium alkyl sulfate | 7 parts |

The above components were mixed homogenously and, after being ground finely, granulated to obtain granules with a diameter of 0.5 to 1.0 mm and 5% of active ingredient.

Test Examples regarding the effect of herbicides of the present invention are shown next.

Herbicidal effects were examined following the below examination criteria and are represented by the use of herbicidal index.

Examination Criteria

| Herbicidal rate | Herbicidal index |
|---|---|
| 0% | 0 |
| 20-29% | 2 |
| 40-49% | 4 |
| 60-69% | 6 |
| 80-89% | 8 |
| 100% | 10 |

Additionally, numerical values 1, 3, 5, 7, and 9 respectively show intermediate values between 0 and 2, between 2 and 4, between 4 and 6, between 6 and 8, and between 8 and 10.

$$\text{Herbicidal rate (\%)} = \frac{\{(\text{Fresh weight of shoots in a non-treated plot})\} - \{(\text{Fresh weight of shoots in a treated plot})\}}{(\text{Fresh weight of shoots in a non-treated plot})} \times 100 \quad [\text{Equation 1}]$$

TEST EXAMPLE 1

Upland Farming Foliar Treatment Test

A 200-cm² pot was filled with soil and respective seeds of crabgrass, giant foxtail, velvetleaf, and pigweed were planted in the surface layer thereof, and, after lightly covering with soil, the plants were grown in a greenhouse. When each weed had grown to 5-10 cm in height, a water-dilution of emulsifiable concentrate shown in Formulation Example 2 of each compound under test was applied to foliar parts of weeds by a small atomizer so that the active ingredient would reach a predetermined dose, in an amount equivalent to the application amount of 1000 l/ha. The plants were grown in a greenhouse and 2 weeks after the treatment, herbicidal effects on weeds were examined following the examination criteria.

Results showed that compounds listed below had a herbicidal index of 8 or more with any of the weeds of crabgrass, giant foxtail, velvetleaf, and pigweed at 1000 g/ha. Note that compound numbers correspond to those in Table 3.
Tested Compounds
1-411, 413, 415-418, 420, 422, 431, 433-447, 449-451
Compounds with a Herbicidal Index of 8 or more
1-18, 20-36, 38-59, 61-143, 145-154, 156-160, 163-173, 175, 176, 178-187, 190-198, 200-202, 207, 208, 211-214, 216-221, 224-226, 233, 237-243, 245, 247-251, 253, 256, 258-282, 284-289, 292, 295-303, 305-320, 322-324, 326, 329-342, 344-357, 360-380, 382, 384, 386-389, 393-399, 401-408, 410-411, 413, 415-418, 420, 422-427, 429, 433-447, 449-451.

TEST EXAMPLE 2

Upland Farming Soil Treatment Test

A plastic pot with an area of 70 cm² was filled with field soil and seeds of crabgrass, giant foxtail, velvetleaf, and pigweed were planted thereto and covered with 0.5 cm of soil. A water-dilution of emulsifiable concentrate shown in Formulation Example 2 was applied to the soil surface uniformly so that the active ingredient would reach a predetermined dose. The plants were grown in a greenhouse and 3 weeks after the treatment, herbicidal effects on weeds were examined following the examination criteria.

Results showed that compounds listed below had a herbicidal index of 8 or more with any of the weeds of crabgrass, giant foxtail, velvetleaf, and pigweed at 1000 g/ha. Note that compound numbers correspond to those in Table 3.
Tested Compounds
1-397, 399-411, 416-418, 420, 422-431, 433-435, 437-447, 449-451.
Compounds with a Herbicidal Index of 8 or More
1-17, 19-49, 51-56, 58-142, 145-160, 162-173, 178, 181-185, 189-191, 193, 194, 196-198, 200, 201, 211-214, 217, 218, 220, 221, 224-226, 230, 233, 237-245, 247-252, 254, 258-295, 297-313, 315-317, 319-324, 326, 329-342, 344-357, 360-380, 382, 383-384, 386-390, 392-397, 399-411, 416-418, 420, 422-429, 431, 433-435, 437-441, 443-445, 447, 449-451.

[Industrial Applicability]

According to the present invention, novel amidine compounds which are highly safe and may be used as active ingredients in herbicides that are reliably effective at a lesser dose, and herbicides containing these compounds as active ingredients are provided.

The invention claimed is:
1. Amidine compounds represented by a formula (1')

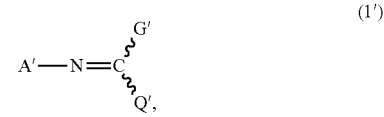

or a salt thereof:
wherein G' represents an optionally substituted pyrrolidine-1-yl group;
Q' represents cyano;
A' is a group represented by a formula (4')

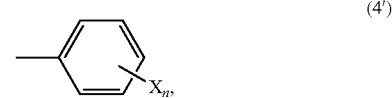

wherein X represents halogen, optionally substituted $C_{1-6}$ alkyl, optionally substituted $C_{2-6}$ alkenyl, optionally substituted $C_{2-6}$ alkynyl, optionally substituted aryl, optionally substituted $C_{1-6}$ alkyl carbonyl, optionally substituted $C_{2-6}$ alkenyl carbonyl, optionally substituted $C_{2-6}$ alkynyl carbonyl, optionally substituted aryl carbonyl, optionally substituted $C_{1-6}$ alkylthiocarbonyl, optionally substituted $C_{2-6}$ alkenylthiocarbonyl, optionally substituted $C_{2-6}$ alkynylthiocarbonyl, optionally substituted arylthiocarbonyl, cyano, substitutent represented by $X^{11}$, optionally substituted amino, nitro, hydroxyl, optionally substituted $C_{1-6}$ alkoxy, optionally substituted $C_{2-6}$ alkenyloxy, optionally substituted $C_{2-6}$ alkynyloxy, optionally substituted aryloxy, optionally substituted heteroyloxy, mercapto, optionally substituted $C_{1-6}$ alkylthio, optionally substituted $C_{2-6}$ alkenylthio, optionally substituted $C_{2-6}$ alkynylthio, optionally substituted arylthio, optionally substituted heteroylthio, optionally substituted alkyl sulfinyl, optionally substituted aryl sulfinyl, optionally alkyl sulfonyl, optionally substituted aryl sulfonyl, or an optionally substituted heterocyclic group; and substitutents which are in positions that are bondable with each other may bond together to form rings;

n' is an integer of 2 to 5 and each X may be the same or different from each other;

$X^{11}$ is a substituent represented by a formula (5)

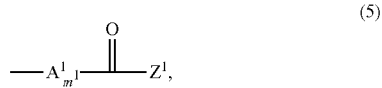

(5)

wherein $m^1$ represents an integer of 0 to 3;

$A^1$ represents an atom selected from carbon, nitrogen, oxygen, and sulfur, and which may be oxidized within a chemically acceptable range and which may be substituted; when $m^1$ is 2 or more, each $A^1$ may be the same or different from each other and combinations of each $A^1$ are within a chemically acceptable range and each $A^1$ may, within a chemically acceptable range of multiplicity, bond to each other; and when $A^1$ is carbon and one or more $A^1$ is substituted by two or more substitutents, the substituents which are in a bondable positional relationship may bond together to form a ring;

$Z^1$ represents a group represented by —$OR^{11}$ or —$NR^{12}R^{13}$;

$R^{11}$ represents hydrogen, optionally substituted $C_{1-6}$ alkyl, optionally substituted $C_{2-6}$ alkenyl, optionally substituted $C_{2-6}$ alkynyl, optionally substituted aryl, an optionally substituted heterocyclic group, or a group represented by $X^{12}$;

$R^{12}$ and $R^{13}$ each independently represents hydrogen, optionally substituted $C_{1-6}$ alkyl, optionally substituted $C_{2-6}$ alkenyl, optionally substituted $C_{2-6}$ alkynyl, optionally substituted aryl, an optionally substituted heterocycle, a group represented by $X^{12}$, hydroxyl, optionally substituted $C_{1-6}$ alkoxy, optionally substituted $C_{2-6}$ alkenyloxy, optionally substituted $C_{2-6}$ alkynyloxy, optionally substituted aryloxy, optionally substituted alkyl sulfinyl, optionally substituted aryl sulfinyl, optionally substituted alkyl sulfonyl, optionally substituted aryl sulfonyl, or optionally substituted amino; and $R^{12}$ and $R^{13}$ may further bond together to form a ring;

$X^{12}$ is a substituent represented by a group (6)

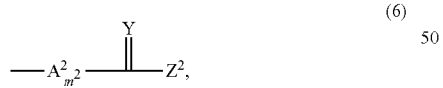

(6)

wherein $m^2$ is an integer of 1 to 3, $A^2$ represents optionally substituted carbon and may be substituted within a chemically acceptable range and when $m^2$ is 2 or more, each $A^2$ may bond to each other within a chemically acceptable range of multiplicity; and when one or more $A^2$ is substituted by two or more substituents, the substituents which are in a bondable positional relationship may bond together to form a ring;

Y represents oxygen or optionally substituted nitrogen;

$Z^2$ is a group represented by —$OR^{21}$ or —$NR^{22}R^{23}$ when Y is oxygen and $Z^2$ represents hydrogen or optionally substituted $C_{1-6}$ alkyl when Y is nitrogen;

$R^{21}$ represents hydrogen, optionally substituted $C_{1-6}$ alkyl, optionally substituted $C_{2-6}$ alkenyl, optionally substituted $C_{2-6}$ alkynyl, optionally substituted aryl, an optionally substituted heterocycle, or a group represented by $X^{13}$;

$R^{22}$ and $R^{23}$ each independently represent hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, a group represented by $X^{13}$, optionally substituted $C_{1-6}$ alkoxy, optionally substituted $C_{2-6}$ alkenyloxy, optionally substituted $C_{2-6}$ alkynyloxy, optionally substituted aryloxy, optionally substituted alkyl sulfinyl, optionally substituted aryl sulfinyl, optionally substituted alkyl sulfonyl, or optionally substituted aryl sulfonyl; and $R^{22}$ and $R^{23}$ may bond together to form a ring when neither is hydrogen;

$X^{13}$ is a substituent represented by a formula (7)

(7)

wherein $m^3$ is an integer of 1 to 3;

$A^3$ represents optionally substituted carbon and may be substituted within a chemically acceptable range, and when $m^3$ is 2 or more, each $A^3$ may bond to each other within a chemically acceptable range of multiplicity; and when one or more $A^3$ is substituted by two or more substituents, the substituents which are in a bondable positional relationship may bond together to form a ring;

$Z^3$ is a group represented by —$OR^{31}$ or —$NR^{32}R^{33}$;

$R^{31}$ represents hydrogen, optionally substituted $C_{1-6}$ alkyl, optionally substituted $C_{2-6}$ alkenyl, optionally substituted $C_{2-6}$ alkynyl, optionally substituted aryl, or an optionally substituted heterocyclic group;

$R^{32}$ and $R^{33}$ each independently represents hydrogen, optionally substituted $C_{1-6}$ alkyl, optionally substituted $C_{2-6}$ alkenyl, optionally substituted $C_{2-6}$ alkynyl, optionally substituted aryl, optionally substituted heterocycle, optionally substituted $C_{1-6}$ alkoxy, optionally substituted $C_{2-6}$ alkenyloxy, optionally substituted $C_{2-6}$ alkynyloxy, optionally substituted aryloxy, optionally substituted alkyl sulfinyl, optionally substituted aryl sulfinyl, optionally substituted alkyl sulfonyl, or optionally substituted aryl sulfonyl; and $R^{32}$ and $R^{33}$ may further bond together to form a ring when neither is hydrogen).

* * * * *

UNITED STATES PATENT AND TRADEMARK OFFICE
CERTIFICATE OF CORRECTION

PATENT NO. : 8,212,050 B2
APPLICATION NO. : 11/989846
DATED : July 3, 2012
INVENTOR(S) : Yasuhiro Miyashita Page 1 of 1

It is certified that error appears in the above-identified patent and that said Letters Patent is hereby corrected as shown below:

In the Claims:

In column 342, line 65 change "optionally alkyl" to --optionally substituted alkyl--

Signed and Sealed this
Eleventh Day of June, 2013

Teresa Stanek Rea
*Acting Director of the United States Patent and Trademark Office*